United States Patent
Bayne et al.

(10) Patent No.: US 11,987,819 B2
(45) Date of Patent: May 21, 2024

(54) METHOD OF INCREASING OMEGA-3 POLYUNSATURATED FATTY ACIDS PRODUCTION IN MICROALGAE

(71) Applicant: DSM IP Assets B.V., Heerlen (NL)

(72) Inventors: Anne-Cecile V. Bayne, Ellicott City, MD (US); Ross E. Zirkle, Mount Airy, MD (US)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 16/300,212

(22) PCT Filed: May 11, 2017

(86) PCT No.: PCT/EP2017/061347
§ 371 (c)(1),
(2) Date: Nov. 9, 2018

(87) PCT Pub. No.: WO2017/194683
PCT Pub. Date: Nov. 16, 2017

(65) Prior Publication Data
US 2019/0144838 A1 May 16, 2019

Related U.S. Application Data

(60) Provisional application No. 62/335,498, filed on May 12, 2016.

(51) Int. Cl.
| | | |
|---|---|---|
| *A01H 5/00* | (2018.01) | |
| *C12N 9/10* | (2006.01) | |
| *C12N 15/00* | (2006.01) | |
| *C12N 15/82* | (2006.01) | |
| *C12P 7/6432* | (2022.01) | |
| *C12P 7/6472* | (2022.01) | |

(52) U.S. Cl.
CPC .............. *C12N 9/1029* (2013.01); *A01H 5/00* (2013.01); *C12N 15/00* (2013.01); *C12N 15/8247* (2013.01); *C12P 7/6432* (2022.01); *C12P 7/6472* (2013.01); *C12Y 203/01085* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 4,743,546 A | 5/1988 | Backman et al. |
| 5,130,242 A | 7/1992 | Barclay |
| 5,380,831 A | 1/1995 | Adang et al. |
| 6,140,486 A | 10/2000 | Facciotti et al. |
| 6,166,302 A | 12/2000 | Merlo et al. |
| 6,566,583 B1 | 5/2003 | Facciotti et al. |
| 6,812,009 B2 | 11/2004 | Gladue et al. |
| 7,001,772 B2 | 2/2006 | Roessler et al. |
| 7,208,590 B2 | 4/2007 | Mukerji et al. |
| 7,211,418 B2 | 5/2007 | Metz et al. |
| 7,217,856 B2 | 5/2007 | Weaver et al. |
| 7,247,461 B2 | 7/2007 | Metz et al. |
| 7,256,022 B2 | 8/2007 | Metz et al. |
| 7,259,006 B2 | 8/2007 | Komazawa et al. |
| 7,348,473 B2 | 3/2008 | Kubik |
| 7,355,100 B2 | 4/2008 | Kubik |
| 7,368,552 B2 | 5/2008 | Mukerji et al. |
| 7,456,340 B2 | 11/2008 | Kubik |
| 8,003,772 B2 | 8/2011 | Weaver et al. |
| 8,637,651 B2 | 1/2014 | Apt et al. |
| 8,859,855 B2 | 10/2014 | Weaver et al. |
| 8,940,884 B2 | 1/2015 | Apt et al. |
| 8,945,875 B2 | 2/2015 | Roessler et al. |
| 2002/0001833 A1 | 1/2002 | Ruecker et al. |
| 2002/0194641 A1 | 12/2002 | Metz et al. |
| 2003/0166207 A1 | 9/2003 | Roessler et al. |
| 2004/0172682 A1 | 9/2004 | Kinney et al. |
| 2004/0235127 A1 | 11/2004 | Metz et al. |
| 2005/0100995 A1 | 5/2005 | Weaver et al. |
| 2007/0244192 A1 | 10/2007 | Metz |
| 2008/0050505 A1 | 2/2008 | Valentin et al. |
| 2010/0266564 A1* | 10/2010 | Apt ................ C12Y 402/01059 424/94.1 |

(Continued)

FOREIGN PATENT DOCUMENTS

| | | |
|---|---|---|
| CN | 102741267 | 10/2012 |
| CN | 102884201 | 1/2013 |

(Continued)

OTHER PUBLICATIONS

Abbadi et al, Biosynthesis of Very-Long-Chain Polyunsaturated Fatty, The Plant Cell, 2004, 2734-2748, 16.
Altschul et al., Basic Local Alignment Search Tool, J. Mol. Biol., 1990, 403-410, 215.
Ausubel et al, Current Protocols in Molecular Biology, John Wiley & Sons, 1995.
Banker & Rhodes, Modern Pharmaceutics, Informa Healthcare USA 4th Ed., 2002.
Bergé et al, Fatty Acids from Lipids of Marine Organisms:, Adv Biochem Engin/Biotechnol, 2005, 49-125, 96.

(Continued)

*Primary Examiner* — Phuong T Bui
(74) *Attorney, Agent, or Firm* — Nixon & Vanderhye, PC

(57) ABSTRACT

The subject disclosure features, in one aspect, a method for producing lipids enriched for EPA, comprising modifying a microalga to increase expression of PFA1, and/or PFA3, and culturing the modified microalga under conditions which allow the expression of PFA1, and/or PFA3, wherein lipids enriched for EPA are produced. Also featured is a recombinant microalga in which PFA1, and/or PFA3, is overexpressed. Such recombinant microalgae have been demonstrated herein to produce very favorable fatty acid lipid profiles (e.g., increased levels of EPA, increased ratio of EPA:DHA, decreased levels of DPA n-6, etc.).

13 Claims, 9 Drawing Sheets

Specification includes a Sequence Listing.

(56) References Cited

U.S. PATENT DOCUMENTS

| | | |
|---|---|---|
| 2010/0326479 A1 | 12/2010 | Brailsford |
| 2011/0295028 A1 | 12/2011 | Cherinko et al. |
| 2013/0150599 A1 | 6/2013 | Walsh et al. |
| 2013/0317140 A1 | 11/2013 | Özyürek et al. |
| 2015/0299676 A1* | 10/2015 | Walsh .................. C12N 9/1288 800/306 |
| 2015/0340122 A1 | 11/2015 | Keestra et al. |

FOREIGN PATENT DOCUMENTS

| | | |
|---|---|---|
| JP | 2007-524377 | 8/2007 |
| JP | 2012-521195 | 9/2012 |
| WO | 1997013402 | 8/2004 |
| WO | WO2004071467 A2 | 8/2004 |
| WO | WO2004087879 A3 | 10/2004 |
| WO | WO2005097982 | 10/2005 |
| WO | WO2006135866 | 12/2006 |
| WO | WO2010108114 A2 | 9/2010 |
| WO | WO2011146524 A1 | 11/2011 |
| WO | WO2013016546 | 1/2013 |
| WO | WO2015081270 | 6/2015 |

OTHER PUBLICATIONS

Black et al, Analysis of a Het—Mutation in *Anabaena* sp. Strain PCC 7120, Journal of Bacteriology, 1994, 2282-2292, 176.
Bumpus et al, Polyunsaturated Fatty-Acid-Like Trans-Enoyl Reductases Utilized in, JACS, 2008, 11614-11616, 130.
Campbell et al, A polyketide-synthase-like gene is involved in the synthesis, Arch Microbiol, 1997, 251-258, 167.
Corpet et al, Multiple Sequence Alignment with Hierarchial Clustering, Nucleic Acids Res., 1988, 10881-90, 16.
Donadio et al, Organization of the enzymatic domains in the multifunctional polyketide synthase involved in erythro—, Gene, 1992, 51-60.
Felgner et al, Lipofection: A highly efficient, lipid-mediated, Proc. Nati. Acad. Sci. USA, 1987, 7413-7417, 84.
Finn et al, The Pfam protein families database: towards a more, Nucleic Acids Research, 2016, D279-D285, 44.
Fraley et al, Expression of bacterial genes in plant cells, Proc. NatL. Acad. Sci. USA, 1983, 4803-4807, 80.
Fromm et al, Stable transformation of maize after gene transfer by electroporation, Nature, 1986, 791-793, 319.
Goodman et al., Goodman & Gilman's The Pharmaceutical Basis of Therapeutics, 2001, McGraw-Hill Companies, Inc.
Gupta et al, Biotechnology Advances, Omega-3 biotechnology: Thraustochytrids as a novel source of omega-3 pils, 2012, 1733-1745, 30.
Hauvermale et al, Lipids, Fatty Acid Production in *Schizochytrium* sp., 2006, 739-747, 41.
Heath et al, A triclosan-resistant bacterial enzym, Microbiology, 2000, 145-146.
Heath et al, Regulation of Fatty Acid, The Journal of Biological Chemistry, 1996, 27795, 271.
Higgins et al., CLUSTAL: A package for performing multiple sequence alignment on a microcomputer, Gene, 1988, 237-244, 73(1).
Higgins et al., Fast and sensitive multiple sequence alignments on a microcomputer, Cabios Communications, 1989, 151-153, 5(2).
Higuchi et al., Pro-drugs as Noval Delivery Systems, ACS Symposum Series, 1975, Book, American Chemical Society.
Huang et al, Profile of Polyunsaturated Fatty Acids Produced by, IJ. Am. Oil. Chem. Soc., 2001, 605-610, 78.
Huang et al., Grouping Newly Isolated Docosahexaenoic Acid-Producing Thraustochytrids Based on Their Polyunsaturated Fatty Acid Profiles and Comparative Analysis of 18S rRNA Genes, Marine Biotechnology, 2003, 450-457, 5.
Huang et al., Parallelization of a local similarity algorithm, CABIOS, 1992, 155-165, 8(2).

J. Sambrook, Molcular Cloning, A Laboratory Manual, 1989, Table of contents, Second.
Jiang et al, The role of Tandem Acyl Carrier Protein Domains in Polyunsaturated Fatty Acid Biosynthesis, JACS, 2008, 6336-6337, 130.
Klein et al, High-velocity microprojectiles for delivering nucleic acids into living cells, nature, 1987, 70, 327.
Lewis, et al., The Biotechnological Potential of Thraustochytrids, School of Agricultural Science, 1999, p. 580-587, vol. 1.
Lippmeier et al., Characterization of Both Polyunsaturated Fatty Acid Biosynthetic Pathways in *Schizochytrium* sp., Lipids, 2009, 621-630, 44.
McOmie, J.F., Protective Groups in Organic Chemistry, Book, 1973, Plenum Press, New York.
Metz et al., Production of Polyunsaturated Fatty Acids by Polyketide Synthasese in Both Prokaryotes and Eukaryotes, Science, 2001, 290-293, 293.
Mofid et al., Structure-Based Mutational Analysis of the 4'-Phosphopantetheinyl Transferases Sfp from Bacillus subtilis: Carrier Protein Recognition and Reaction mechanism, Biochemistry, 2004, 4128-4136, 43.
Mueller et al, Mapping of Early SV40-Specific Functions by, Cell, 1978, 579-585, 15.
Mullis et al, Amplification of a Short DNA Stretch, Science, 1988, 487-491, 239.
Nakano et al, Isolation and characterization o f sfp: a gene that functions in the, Mol Gen Genet, 1992, 313-321, 232.
Napier and Sayanova, The production of very-long-chain PUFA biosynthesis in transgenic, Proceedings of the Nutrition Society, 2005, 387-393, 64.
Needleman et al., A General Method Applicable to the Search for Similarities in the Amino Acid Sequence of Two Proteins, J. Mol. Biol., 1970, 443-453, 48.
Pearson et al, Methods Mol. Biol., 1994, 307-??, 24.
Pearson et al., Improved tools for biological sequence comparison, Proc. Natl. Acad. Sci., 1988, 2444-2448, 85.
Qi et al, Production of very long chain polyunsaturated, Nature Biotechnology, 2004, 739-745, 22.
Remington, The Science and Practice of Pharmacy, 2005, (Book), 21st Edition.
Reuter et al., Crystal structure of the surfactin synthetase-activating enzyme Sfp: a prototype of the 4' phosphopantetheinyl transferase superfamily, The EMBO Journal, 1999, 6823-6831, 18(23).
Robert et al, Metabolic engineering of Arabidopsis to produce nutritionally important, Functional Plant Biology, 2005, 473-479, 32.
Roche, Edward B., Bioreversible Carriers in Drug Design, Theory and Application, 1987, 13-94, Book, American Pharmaceutical Association, Pergamon.
Roche, Helen M., Unsaturated Fatty Acids, Proceedings of the Nutrition Society, 1999, p. 397-401, vol. 58.
Ruiz-Lopez et al, Modifying the lipid content and composition of plant seeds:, Appl Microbiol Biotechnol, 2015, 143-154, 99.
Sambrook J, Molecular Cloning, A Laboratory Manual, 2001, (Book), 3rd Edition, Cold Spring Harbor Laboratory Press, Cold Spring Harbor, New York.
Schena et al, A steroid-inducible gene expression system for plant cells, Proc. Natl. Acad. Sci. USA, 1991, 10421-10425, 88.
Smith et al., Comaprison of Biosequences, Advances in Applied Mathematics, 1981, 482-489, 2.
Tabor et al, A bacteriophage T7 RNA polymerase/promoter system for, Proc. Nati. Acad. Sci. USA, 1985, 1074-1078, 82.
Tatusova et al, Blast 2 Sequences, a new tool for comparing protein and, FMES Microbiology letters, 1999, 247-250, 174.
Thompson et al, CLUSTAL W: improving the sensitivity of progressive, Nucleic Acids Research, 1994, 4673-4680, 22.
Walker et al, Isothermal in vitro amplification of DNA by a restriction, Proc. Nati. Acad. Sci. USA, 1991, 392-396, 89.
Ward et al, Chemical regulation of transgene expression in plants, Plant Molecular Biology, 1993, 361-366, 22.
Cui et al., Cui et al., Regulating effect of β-ketoacyl synthase domain of fatty acid synthase on fatty acyl chain length in de novo fatty acid synthesis. Biochim. Biophys. Acta.1861:149-155 (2016).

(56) References Cited

OTHER PUBLICATIONS

Hayashi et al., "Enhanced production of polyunsaturated fatty acids by enzyme engineering of tandem acyl carrier proteins," Scientific Reports 6: Article No. 35441, doi: 10.1038/srep35441, 10 pages (2016).
Jiang et al., "The Role of Tandem Acyl Carrier Protein Domains in Polyunsaturated Fatty Acid Biosynthesis," J. Am. Chem. Soc. 130: 6336-6337 (2008).
Zirkle & Metz, "PUFA Synthases," AOCS Lipid Library®, available at https://lipidlibrary.aocs.org/chemistry/physics/microbial-lipid/pufa-synthases (2015).
Xu et al., Structural Analysis of Protein-Protein Interactions in Type I Polyketide Synthases, Crit. Rev. Biochem. Mol. Biol. 48(2): 98-122 (2013).
Maier et al., "The Crystal Structure of a Mammalian Fatty Acid Synthase," Science, 321:1315-1322 (2008).

\* cited by examiner

A
25°C
| Sample | N230D | B156-2 |
|---|---|---|
| Fatty Acid | % FAME | % FAME |
| C14:0* | 19.87 | 20.16 |
| C16:0* | 23.00 | 20.87 |
| C16:1* | 15.05 | 19.56 |
| C18:0* | 0.27 | 0.34 |
| C18:1 n-7 | 3.18 | 5.77 |
| C20:4 n-6* | 0.05 | 0.05 |
| C20:4 n-3 | 0.19 | 0.10 |
| C20:5 n-3* | 0.39 | 1.12 |
| C22:5 n-6* | 8.20 | 1.78 |
| C22:6 n-3* | 23.39 | 28.56 |
| Sum FAME (mg/g) | 719.82 | 613.25 |
B
30°C
| Sample | N230D | B156-2 |
|---|---|---|
| Fatty Acid | % FAME | % FAME |
| C14:0* | 16.12 | 15.44 |
| C16:0* | 25.64 | 36.70 |
| C16:1* | 7.22 | 9.54 |
| C18:0* | 0.36 | 0.72 |
| C18:1 n-7 | 2.34 | 3.31 |
| C20:4 n-6* | 0.22 | 0.21 |
| C20:4 n-3 | 0.41 | 0.23 |
| C20:5 n-3* | 0.60 | 1.17 |
| C22:5 n-6* | 13.16 | 3.03 |
| C22:6 n-3* | 32.34 | 28.46 |
| Sum FAME (mg/g) | 720.04 | 709.47 |
FIG. 4

SEQUENCE LISTING

<160> NUMBER OF SEQ ID NOS: 42

<210> SEQ ID NO 1
<211> LENGTH: 7824
<212> TYPE: DNA
<213> ORGANISM: Schizochytrium sp.

<400> SEQUENCE: 1

| | | | | | | |
|---|---|---|---|---|---|---|
| atggatactc | gcatcgcgat | cgtggggatg | tcggcgatcc | tgccgagcgg | ggagaacgtg | 60 |
| cgcgagagct | gggaggcgat | ccgcgatggg | ctggattgcc | tgagcgatct | gccggcggac | 120 |
| cgcgtggacg | tgacggccta | ctacaacccg | agaagacga | ccaaggacaa | gatctactgc | 180 |
| aagcgcggcg | ggttcatccc | ggagtacgac | ttcgacgcgc | gtgagttcgg | gctcaacatg | 240 |
| ttccagatgg | aggactcgga | cgccaaccag | acgatctcgc | tgctcaaggt | gaaggaggcg | 300 |
| ctgacggacg | ccaacatccc | ggcgttctcg | agcggtaaga | gaacatcgg | ctgcgtgctg | 360 |
| ggcatcggcg | gcggccagaa | ggcgagccac | gagttctact | cgcggctcaa | ctacgtggtc | 420 |
| gtggacaagg | tgctgcgcaa | gatgggcctg | ccggaggaag | acgtggcggc | ggcggtggac | 480 |
| aagtacaagg | cgagtttccc | cgagtggcgc | ctcgactctt | tccccgggtt | cctgggcaac | 540 |
| gtcacggcgg | ggcgctgctg | caataccttc | aacatggagg | gcatgaactg | cgtcgtggac | 600 |
| gcggcctgcg | cgtcgtcgct | gatcgcggtc | aaagtggcga | tcgaggagct | gctctacggc | 660 |
| gactgcgatg | cgatgatcgc | gggtgccacc | tgcacggaca | actcgatcgg | gatgtacatg | 720 |
| gccttctcca | agacgcccgt | gttttccacg | gacccgagcg | tcaaggcgta | cgacgccgcc | 780 |
| accaaaggca | tgctcatcgg | cgagggctcg | gcgatgctcg | tgctgaagcg | ctacgcggac | 840 |
| gccgtgcgcg | acggcgacac | cgtgcacgcc | gtcatcaagg | ggtgcgcgtc | ctcgagcgac | 900 |
| ggcaaggcgg | cgggcatcta | cacgccgaca | atctcgggcc | aggaggaggc | cctgcgccgc | 960 |
| gcctacgccc | gcgccaatgt | cgaccccgcc | actgtgacgc | tggtggaggg | ccacggcacg | 1020 |
| ggtacgccgg | tgggcgacaa | gatcgagctg | acggcgctga | gcaacctctt | ctccaaggcg | 1080 |
| ttttctgcca | acggtggcgg | cgcggaggaa | gcagagcagg | tggcggtggg | cagcatcaag | 1140 |
| tcgcagatcg | ggcacctcaa | ggcggtggcc | gggctggccg | ggctggtcaa | ggtggtgctg | 1200 |
| gcgctcaagc | acaagacgct | gccgcagacg | atcaacgtcg | acaagccgcc | gtcgctggtg | 1260 |
| gacgggaccc | cgatccagca | gtcgccgctg | tacgtcaaca | cgatgaaccg | ccctggttc | 1320 |
| acgcccgtag | gggtgccgcg | ccgcgccggc | gtgtcgtcgt | ttgggtttgg | cggtgccaac | 1380 |
| taccacgccg | tgctggagga | gtttgagccc | gagcacgaga | gcgcgtaccg | gtacaacaac | 1440 |
| ctgccgcagg | tggcgctgct | gcacgcgggg | gacgtcgcga | ccttggcggc | gacggttcgc | 1500 |
| gccaagctgg | cgctggccac | cgccgagcag | gaagaggcgc | gtgtggtgaa | gaacgcggac | 1560 |
| tacatcgcgt | accaccggtt | cctggacgag | tgcaagttgc | gcggcgctgt | gccgcaggcg | 1620 |
| cacgcgcggg | tgggactgct | cgtacgggac | ctgagctcgc | tcatcgccgt | gctcgaggcc | 1680 |
| gctgccgcca | agctcgcggg | cgaagagagc | gcgacggagt | ggacggtcag | cgttgctacg | 1740 |
| ggcgaggcgg | ccttccgcgt | gcgcggtgtg | gctacggagg | ccaacgtggc | ggcgctgttc | 1800 |
| tcgggccagg | gcgcgcagta | cacgcacatg | ttcagcgacg | tggcgatgaa | ctggcccccg | 1860 |
| ttccgcgaga | gcgtcgccgc | catgaccgc | gcccagcgcg | agcgcttcgg | gcggcctgcc | 1920 |
| aagcgcgtga | gcagcgtgct | gtacccgcgc | aagccgtacg | gcgacgaacc | gcggcaggac | 1980 |
| cacaaggaga | tctcgcaaac | gcgctactcg | cagcccgcaa | cgctcgcgtg | ctcggtcggc | 2040 |
| gcctttgaca | tcttcaaagc | ggcgggactg | gcgccgagct | ttgcggcggg | ccactcgctg | 2100 |

```
ggcgagtttg cggcgctcta cgcggccggg tcgctcgatc gcgacgccgt cttcgacctg    2160
gtctgcgcgc gcgccaaggc catgagcgac ttcacggccc aggccagcag cagcggtggc    2220
gccatggcgg ccgtgattgg cgccaaggcg gaccagctct cgctgggtgg cgcgcccgac    2280
gtgtggctcg ccaacagcaa ctcgccctcg cagaccgtga tcacgggaac cgccgaagca    2340
gtggctgcgg cctctgacaa gttgcgctgc agcggcaact tccgcgtcgt gcctctggcc    2400
tgcgaggcgg ccttccactc gccgcacatg cgcggcgcgg agcagacgtt tgcgtcggcg    2460
ctcgcgcagg cgcccgtgtc ggcaccggcg gctgctcggt tctactctaa cgtgacgggg    2520
ggcgccgcgg taacctcgcc cgcggacgtc aaaacgaacc tgggcaagca catgacgagc    2580
cctgtgcagt tcgtgcagca ggtgcgagcc atgcacgcgg cgggcgcgcg tgtgtttgtg    2640
gagtttgggc ccaagcaggt cctgtcgcgc ctcgtcaagg agacccttgg cgaggccggc    2700
gacgtggtca cggtcgccgt caacccagac tcggccaagg acagcgacac gcagctgcgc    2760
caggcggcgc tcacgttggc ggtcgccggc gtgccgctca aggactttga ccgctggcag    2820
ctgccggatg ccacgcgcct cgagcctgtc aagaagaaga agaccacgtt gcggctctcg    2880
gcagccacct acgtctccgc caagacgttg cgccagcgcg aggccgtgct caacgacggc    2940
tacactgtca gtggtgccac ggcggtagtc aaggaagtgg acacggccaa cgaggagcgt    3000
ctcgtccgcc aagcccagga tctccagcgc cagctcgcgg aggcctcgac ggcagcccag    3060
gcggcgcagt ccaaggtcgc ggagctcgag cgcacgatcc aggacttgga gcgcaaggtg    3120
cagcagcagc agcaagagaa gggtgagaac tcagacagca acgctgccgc cgaagtgctg    3180
cggcgccaca aggagctgct ccagcgcatg ctgcaggact gtgacgagca ggcagtgccc    3240
gtagccacgg tggttccgac acctacgtcc tccccgacgc ctacatcctc acccgtatcc    3300
ggcaacagca agagcactcg tggcagtgct gatctgcaag cgctgctggc caaggcggag    3360
actgtggtga tggctgtgct ggctgccaag actggctacg aggccgacat ggttgaggcg    3420
gacatggacc tggaggccga gctcggcatc gactcgatca agcgcgtgga gatccttttcc   3480 gaggtgcagg gccagctggg cgtcgaggcc aaggacgtgg atgcgctgag ccgcacgcgc    3540
acggtcggtg aggttgtgga cgccatgaag gcggagatcg tggctgcctc tggtggtagt    3600
gctcctgcgg ttccttcggc gcccgctgct tctgcagctc cgactcccgc tgcttcgact    3660
gcgccttctg ctgatctgca agcgctgctg tccaaggcgg agactgtggt gatggctgtg    3720
ctggcggcca agactggcta cgaggccgac atggtcgagg cggacatgga cctggaggcc    3780
gagctcggca tcgactcgat caagcgcgtg agatcctct cggaggtgca gggccagctg    3840
ggcgtcgagg ccaaggacgt ggatgcgctg agccgcacgc gcacggtcgg tgaggttgtg    3900
gatgccatga aggcggaaat cgtggctgcc tctgctggta gtgctcctgc tcctgctgtt    3960
ccttcggcgc ccgctgcttc tgcagctccg actcccgctg cttcgactgc gccttctgct    4020
gatctgcaag cgctgctgtc caaggcggag acggtggtga tggctgtgct ggcggccaag    4080
actggctacg aggccgacat ggtcgaggcg gacatggacc tggaggccga gctcggcatc    4140
gactcgatca agcgcgtgga gatcctctcg gaggtgcagg gccagctggg cgtcgaggcc    4200
aaggacgtgg atgcgctgag ccgcacgcgc acggtcggtg aggttgtgga tgccatgaag    4260
gcggaaatcg tggctgcctc tggtggtagt gctcctgctc tgcggttcc ttcggcgccc    4320 gctgcttctg cagctccgac tcccgcggct gcgacagcgc cttctgctga tctgcaagcg    4380
ctgctggcca aggcggagac tgtggtgatg gctgtgctgg cggccaagac tggctacgag    4440
```

```
gccgacatgg tcgaggcgga catggacctg gaggccgagc tcggcatcga ctcgatcaag    4500
cgcgtggaga tcctttccga ggtgcagggc cagctgggcg tcgaggccaa ggacgtagat    4560
gcgctgagcc gcacgcgcac ggtcggtgag gttgtggatg ccatgaaggc ggagatcgtg    4620
gctgcctctg ctggtagtgc tcctgctcct gctgttcctt cggcgcccgc tgcttctgca    4680
gctccgactc ccgctgcttc gactgcgcct tctgctgatc tgcaagcgct gctgtccaag    4740
gcggagactg tggtgatggc tgtgctggcg gccaagactg gctacgaggc cgacatggtc    4800
gaggcggaca tggacctgga ggccgagctc ggcatcgact cgatcaagcg cgtggagatc    4860
ctctcggagg tgcagggcca gctgggcgtc gaggccaagg acgtggatgc gctgagccgc    4920
acgcgcacgg tcggtgaggt tgtggatgcc atgaaggcgg aaatcgtggc tgcctctggt    4980
ggtagtgctc ctgctgctgc tgttccttcg gcgcccgctg cttctgcagc tccgactcct    5040
gcgactgcgc cttctgctga tctgcaagcg ctgctgtcca aggcggagac tgtggtgatg    5100
gctgtgctgg cggccaagac tggctacgag gccgacatgg tcgaggcgga catggacctg    5160
gaggccgagc tcggcatcga ctcgatcaag cgcgtggaga tcctttccga ggtgcagggc    5220
cagctgggcg tcgaggccaa ggacgtagat gcgctgagcc gcacgcgcac ggtcggtgaa    5280
gtggtggacg ccatgaaggc ggagatcgtg gctgcctctg gtggtagtgc tcctgctgct    5340
ccttcggcgc ccgcgcttct tccaacgctg tttggttccg agtgcgagga cctgtctctg    5400
acctttcccg tgataacgac cctgccgctt cctgcagagc ttgtgctggc cgagggcggc    5460
gctcgccctg tagtcgtggt ggatgatgga tctgcactca cctcgtcgct ggtgtcctcg    5520
ctcggcgatc gtgcggtgct gctgcaggtg cagtcttcct ctgcctgctc gccgcgctcg    5580
accacgcaca agttggtgac cgtagcagac cgctctgaag cggcgctaca ggcggcgctc    5640
acgtccgtcg aggcgcagtt cggcaaggtg ggtggctttg tgttccagtt cggcgacgac    5700
gacgtgcaag cgcagctcgg ctgggcgctg ctcgcggcca agcacctcaa aacttcgctg    5760
tcagaacaga tcgagggcgg tcgcaccttt ttcgtggccg tcgcgcggct cgacggccag    5820
ctggggctct ccggcaagtc gacgaccgct accgttgatc tctcccgcgc gcagcagggc    5880
agcgtgttcg gcctgtgcaa gacactcgac ctggagtggc ccgctgtctt ctgccgcgga    5940
atcgacctgg ccgccgacct cgacgccgca caggccgcgc ggtgcctgct gggcgagctg    6000
tcagaccccg acgtggccgt gcgcgagtct ggttactccg cctcgggcca cgctgcacg    6060
acaactacga agtcgctgac tacgggcaag ccgcaccagc cgatctcctc gtcggacctc    6120
tttctggtgt cggcggcgc gcgcggcatc accccgctgt gcgtgcgcga gctggcgcag    6180
cgcgtgggcg gcggcacgta cgtgctcatc ggccgctcgg agctgccccac gacggagcct    6240
gcctgggcgg tcggcgtgga gtctggcaag ccgctggaga aggccgcgct ggcgttcctg    6300
aaggcggagt ttgcagcggg ccgcggggcc aagccgacgc cgatgctgca caagaagctc    6360
gtgggcgccg tggtcggagc gcgcgaggtg cgagcctcgc tcgccgagat cactgcacag    6420
ggcgccacgg ctgtgtacga gtcgtgcgac gtgagctctg ccgccaaggt gcgtgagatg    6480
gtagagcgcg tgcagcagca gggcgggcgg cgcgtgtcgg gcgtgttcca cgcgtcgggc    6540
gtgctgcgcg acaagctcgt ggagaacaag tcgctggcgg acttcagcgc cgtgtacgac    6600
accaaggtgg gcggcctcat caacctgctg gcctgcgtgg acctggcgca gctgcgtcac    6660
ctcgtgctct tcagctcgct cgcgggcttc cacggcaacg tcgggcagtc ggactacgca    6720
atggccaacg aggcgctcaa caagctgcg gcgcacctgt cggcggtgca cccgcagctg    6780
tgcgcgcgct cgatctgctt cggaccgtgg gacggcggca tggtgacccc cgcgctcaag    6840
```

-continued

```
gccaacttca tccgcatggg catccagatc atcccgcgcc aaggcggcgc gcagaccgtc    6900
gccaacatgc tcgtcagtag ctcccccggt cagctgctcg tgggcaactg gggcgtgcca    6960
cccgtcgtgc cgagtgccac cgagcacacc gtgctgcaga cgctccgcca gagcgacaac    7020
cccttcctcg actcgcacgt gatccagggc cgccgcgtgc tgcccatgac cctggccgtg    7080
ggctacatgg cgcaccaggc gcagagcatc tacgcgggcc accagctgtg gccgtcgag    7140
gacgcccagc tcttcaaggg catcgccatc gacaatggcg ccgacgtgcc cgtgcgcgtg    7200
gagctgtcgc gccgcaagga ggagcaggag gacgccggca aggtcaaggt caaggtgcag    7260
gtgctgctca atcgcaggt caacggcaag tcggtgcccg cgtacaaggc gaccgtcgtg    7320
ctgtcccctg cgccgcgccc agcgtcatc acgcgtgact cgacctcac cccggacccg    7380
gcctgcacgg agcacgacct ctacgacggc aagacgctct ccacggcaa ggccttccag    7440
ggcatcgagc aggtgctctc ggcgacgccc aagcagctca ccgccaagtg ccgcaatttg    7500
ccctcacgc ccgagcagcg cggccagttc gtcgttaacc tcagccagca ggacccgttc    7560
caggcggaca ttgcgttcca ggcgatgctc gtctgggcgc gcatgctgcg ccaatcggcg    7620
gccctgccca caactgcga gcgcttcgac ttttacaagc cgatggcccc gggcgccacc    7680
tactacacgt cggtcaagct ggcctcggcc tcacccttgg tggactctgt gtgcaagtgc    7740
accgtggcga tgcacgatga gcaaggtgag gtgtactttt ctgctcgtgc cagcgtcgtc    7800
ctcaacaaga ccctcacgta ctaa                                           7824
```

<210> SEQ ID NO 2
<211> LENGTH: 2607
<212> TYPE: PRT
<213> ORGANISM: Schizochytrium sp.

<400> SEQUENCE: 2

```
Met Asp Thr Arg Ile Ala Ile Val Gly Met Ser Ala Ile Leu Pro Ser
1               5                   10                  15

Gly Glu Asn Val Arg Glu Ser Trp Glu Ala Ile Arg Asp Gly Leu Asp
            20                  25                  30

Cys Leu Ser Asp Leu Pro Ala Asp Arg Val Asp Val Thr Ala Tyr Tyr
        35                  40                  45

Asn Pro Glu Lys Thr Thr Lys Asp Lys Ile Tyr Cys Lys Arg Gly Gly
    50                  55                  60

Phe Ile Pro Glu Tyr Asp Phe Asp Ala Arg Glu Phe Gly Leu Asn Met
65                  70                  75                  80

Phe Gln Met Glu Asp Ser Asp Ala Asn Gln Thr Ile Ser Leu Leu Lys
                85                  90                  95

Val Lys Glu Ala Leu Thr Asp Ala Asn Ile Pro Ala Phe Ser Ser Gly
            100                 105                 110

Lys Lys Asn Ile Gly Cys Val Leu Gly Ile Gly Gly Gly Gln Lys Ala
        115                 120                 125

Ser His Glu Phe Tyr Ser Arg Leu Asn Tyr Val Val Asp Lys Val
    130                 135                 140

Leu Arg Lys Met Gly Leu Pro Glu Glu Asp Val Ala Ala Val Asp
145                 150                 155                 160

Lys Tyr Lys Ala Ser Phe Pro Glu Trp Arg Leu Asp Ser Phe Pro Gly
                165                 170                 175

Phe Leu Gly Asn Val Thr Ala Gly Arg Cys Cys Asn Thr Phe Asn Met
            180                 185                 190
```

-continued

```
Glu Gly Met Asn Cys Val Val Asp Ala Ala Cys Ala Ser Ser Leu Ile
            195                 200                 205

Ala Val Lys Val Ala Ile Glu Glu Leu Leu Tyr Gly Asp Cys Asp Ala
    210                 215                 220

Met Ile Ala Gly Ala Thr Cys Thr Asp Asn Ser Ile Gly Met Tyr Met
225                 230                 235                 240

Ala Phe Ser Lys Thr Pro Val Phe Ser Thr Asp Pro Ser Val Lys Ala
                245                 250                 255

Tyr Asp Ala Ala Thr Lys Gly Met Leu Ile Gly Glu Gly Ser Ala Met
            260                 265                 270

Leu Val Leu Lys Arg Tyr Ala Asp Ala Val Arg Asp Gly Asp Thr Val
    275                 280                 285

His Ala Val Ile Lys Gly Cys Ala Ser Ser Ser Asp Gly Lys Ala Ala
290                 295                 300

Gly Ile Tyr Thr Pro Thr Ile Ser Gly Gln Glu Glu Ala Leu Arg Arg
305                 310                 315                 320

Ala Tyr Ala Arg Ala Asn Val Asp Pro Ala Thr Val Thr Leu Val Glu
                325                 330                 335

Gly His Gly Thr Gly Thr Pro Val Gly Asp Lys Ile Glu Leu Thr Ala
            340                 345                 350

Leu Ser Asn Leu Phe Ser Lys Ala Phe Ser Ala Asn Gly Gly Gly Ala
    355                 360                 365

Glu Glu Ala Glu Gln Val Ala Val Gly Ser Ile Lys Ser Gln Ile Gly
370                 375                 380

His Leu Lys Ala Val Ala Gly Leu Ala Gly Leu Val Lys Val Val Leu
385                 390                 395                 400

Ala Leu Lys His Lys Thr Leu Pro Gln Thr Ile Asn Val Asp Lys Pro
                405                 410                 415

Pro Ser Leu Val Asp Gly Thr Pro Ile Gln Gln Ser Pro Leu Tyr Val
            420                 425                 430

Asn Thr Met Asn Arg Pro Trp Phe Thr Pro Val Gly Val Pro Arg Arg
    435                 440                 445

Ala Gly Val Ser Ser Phe Gly Phe Gly Gly Ala Asn Tyr His Ala Val
450                 455                 460

Leu Glu Glu Phe Glu Pro Glu His Glu Ser Ala Tyr Arg Tyr Asn Asn
465                 470                 475                 480

Leu Pro Gln Val Ala Leu Leu His Ala Gly Asp Val Ala Thr Leu Ala
                485                 490                 495

Ala Thr Val Arg Ala Lys Leu Ala Leu Ala Thr Ala Glu Gln Glu Glu
            500                 505                 510

Ala Arg Val Val Lys Asn Ala Asp Tyr Ile Ala Tyr His Arg Phe Leu
    515                 520                 525

Asp Glu Cys Lys Leu Arg Gly Ala Val Pro Gln Ala His Ala Arg Val
530                 535                 540

Gly Leu Leu Val Arg Asp Leu Ser Ser Leu Ile Ala Val Leu Glu Ala
545                 550                 555                 560

Ala Ala Ala Lys Leu Ala Gly Glu Ser Ala Thr Glu Trp Thr Val
                565                 570                 575

Ser Val Ala Thr Gly Glu Ala Ala Phe Arg Val Arg Gly Val Ala Thr
            580                 585                 590

Glu Ala Asn Val Ala Ala Leu Phe Ser Gly Gln Gly Ala Gln Tyr Thr
    595                 600                 605

His Met Phe Ser Asp Val Ala Met Asn Trp Pro Pro Phe Arg Glu Ser
```

-continued

```
            610                 615                 620
Val Ala Ala Met Asp Arg Ala Gln Arg Glu Arg Phe Gly Arg Pro Ala
625                 630                 635                 640

Lys Arg Val Ser Ser Val Leu Tyr Pro Arg Pro Tyr Gly Asp Glu
                645                 650                 655

Pro Arg Gln Asp His Lys Glu Ile Ser Gln Thr Arg Tyr Ser Gln Pro
                660                 665                 670

Ala Thr Leu Ala Cys Ser Val Gly Ala Phe Asp Ile Phe Lys Ala Ala
                675                 680                 685

Gly Leu Ala Pro Ser Phe Ala Ala Gly His Ser Leu Gly Glu Phe Ala
            690                 695                 700

Ala Leu Tyr Ala Ala Gly Ser Leu Asp Arg Asp Ala Val Phe Asp Leu
705                 710                 715                 720

Val Cys Ala Arg Ala Lys Ala Met Ser Asp Phe Thr Ala Gln Ala Ser
                725                 730                 735

Ser Ser Gly Gly Ala Met Ala Ala Val Ile Gly Ala Lys Ala Asp Gln
            740                 745                 750

Leu Ser Leu Gly Gly Ala Pro Asp Val Trp Leu Ala Asn Ser Asn Ser
        755                 760                 765

Pro Ser Gln Thr Val Ile Thr Gly Thr Ala Glu Ala Val Ala Ala Ala
770                 775                 780

Ser Asp Lys Leu Arg Cys Ser Gly Asn Phe Arg Val Val Pro Leu Ala
785                 790                 795                 800

Cys Glu Ala Ala Phe His Ser Pro His Met Arg Gly Ala Glu Gln Thr
                805                 810                 815

Phe Ala Ser Ala Leu Ala Gln Ala Pro Val Ser Ala Pro Ala Ala Ala
                820                 825                 830

Arg Phe Tyr Ser Asn Val Thr Gly Gly Ala Ala Val Thr Ser Pro Ala
        835                 840                 845

Asp Val Lys Thr Asn Leu Gly Lys His Met Thr Ser Pro Val Gln Phe
850                 855                 860

Val Gln Gln Val Arg Ala Met His Ala Gly Ala Arg Val Phe Val
865                 870                 875                 880

Glu Phe Gly Pro Lys Gln Val Leu Ser Arg Leu Val Lys Glu Thr Leu
                885                 890                 895

Gly Glu Ala Gly Asp Val Thr Val Ala Val Asn Pro Asp Ser Ala
            900                 905                 910

Lys Asp Ser Asp Thr Gln Leu Arg Gln Ala Ala Leu Thr Leu Ala Val
        915                 920                 925

Ala Gly Val Pro Leu Lys Asp Phe Asp Arg Trp Gln Leu Pro Asp Ala
930                 935                 940

Thr Arg Leu Glu Pro Val Lys Lys Lys Thr Thr Leu Arg Leu Ser
945                 950                 955                 960

Ala Ala Thr Tyr Val Ser Ala Lys Thr Leu Arg Gln Arg Glu Ala Val
                965                 970                 975

Leu Asn Asp Gly Tyr Thr Val Ser Gly Ala Thr Ala Val Val Lys Glu
            980                 985                 990

Val Asp Thr Ala Asn Glu Glu Arg Leu Val Arg Gln Ala Gln Asp Leu
        995                 1000                1005

Gln Arg Gln Leu Ala Glu Ala Ser Thr Ala Ala Gln Ala Ala Gln
    1010                1015                1020

Ser Lys Val Ala Glu Leu Glu Arg Thr Ile Gln Asp Leu Glu Arg
    1025                1030                1035
```

```
Lys Val Gln Gln Gln Gln Glu Lys Gly Glu Asn Ser Asp Ser
    1040            1045            1050

Asn Ala Ala Ala Glu Val Leu Arg Arg His Lys Glu Leu Leu Gln
    1055            1060            1065

Arg Met Leu Gln Asp Cys Asp Glu Gln Ala Val Pro Val Ala Thr
    1070            1075            1080

Val Val Pro Thr Pro Thr Ser Ser Pro Thr Pro Thr Ser Ser Pro
    1085            1090            1095

Val Ser Gly Asn Ser Lys Ser Thr Arg Gly Ser Ala Asp Leu Gln
    1100            1105            1110

Ala Leu Leu Ala Lys Ala Glu Thr Val Val Met Ala Val Leu Ala
    1115            1120            1125

Ala Lys Thr Gly Tyr Glu Ala Asp Met Val Glu Ala Asp Met Asp
    1130            1135            1140

Leu Glu Ala Glu Leu Gly Ile Asp Ser Ile Lys Arg Val Glu Ile
    1145            1150            1155

Leu Ser Glu Val Gln Gly Gln Leu Gly Val Glu Ala Lys Asp Val
    1160            1165            1170

Asp Ala Leu Ser Arg Thr Arg Thr Val Gly Glu Val Val Asp Ala
    1175            1180            1185

Met Lys Ala Glu Ile Val Ala Ala Ser Gly Gly Ser Ala Pro Ala
    1190            1195            1200

Val Pro Ser Ala Pro Ala Ala Ser Ala Ala Pro Thr Pro Ala Ala
    1205            1210            1215

Ser Thr Ala Pro Ser Ala Asp Leu Gln Ala Leu Leu Ser Lys Ala
    1220            1225            1230

Glu Thr Val Val Met Ala Val Leu Ala Ala Lys Thr Gly Tyr Glu
    1235            1240            1245

Ala Asp Met Val Glu Ala Asp Met Asp Leu Glu Ala Glu Leu Gly
    1250            1255            1260

Ile Asp Ser Ile Lys Arg Val Glu Ile Leu Ser Glu Val Gln Gly
    1265            1270            1275

Gln Leu Gly Val Glu Ala Lys Asp Val Asp Ala Leu Ser Arg Thr
    1280            1285            1290

Arg Thr Val Gly Glu Val Val Asp Ala Met Lys Ala Glu Ile Val
    1295            1300            1305

Ala Ala Ser Ala Gly Ser Ala Pro Ala Pro Ala Val Pro Ser Ala
    1310            1315            1320

Pro Ala Ala Ser Ala Ala Pro Thr Pro Ala Ala Ser Thr Ala Pro
    1325            1330            1335

Ser Ala Asp Leu Gln Ala Leu Leu Ser Lys Ala Glu Thr Val Val
    1340            1345            1350

Met Ala Val Leu Ala Ala Lys Thr Gly Tyr Glu Ala Asp Met Val
    1355            1360            1365

Glu Ala Asp Met Asp Leu Glu Ala Glu Leu Gly Ile Asp Ser Ile
    1370            1375            1380

Lys Arg Val Glu Ile Leu Ser Glu Val Gln Gly Gln Leu Gly Val
    1385            1390            1395

Glu Ala Lys Asp Val Asp Ala Leu Ser Arg Thr Arg Thr Val Gly
    1400            1405            1410

Glu Val Val Asp Ala Met Lys Ala Glu Ile Val Ala Ala Ser Gly
    1415            1420            1425
```

```
Gly Ser Ala Pro Ala Pro Ala Val Pro Ser Ala Pro Ala Ala Ser
    1430                1435            1440

Ala Ala Pro Thr Pro Ala Ala Ala Thr Ala Pro Ser Ala Asp Leu
    1445                1450            1455

Gln Ala Leu Leu Ala Lys Ala Glu Thr Val Val Met Ala Val Leu
    1460                1465            1470

Ala Ala Lys Thr Gly Tyr Glu Ala Asp Met Val Glu Ala Asp Met
    1475                1480            1485

Asp Leu Glu Ala Glu Leu Gly Ile Asp Ser Ile Lys Arg Val Glu
    1490                1495            1500

Ile Leu Ser Glu Val Gln Gly Gln Leu Gly Val Glu Ala Lys Asp
    1505                1510            1515

Val Asp Ala Leu Ser Arg Thr Arg Thr Val Gly Glu Val Val Asp
    1520                1525            1530

Ala Met Lys Ala Glu Ile Val Ala Ala Ser Ala Gly Ser Ala Pro
    1535                1540            1545

Ala Pro Ala Val Pro Ser Ala Pro Ala Ala Ser Ala Ala Pro Thr
    1550                1555            1560

Pro Ala Ala Ser Thr Ala Pro Ser Ala Asp Leu Gln Ala Leu Leu
    1565                1570            1575

Ser Lys Ala Glu Thr Val Val Met Ala Val Leu Ala Ala Lys Thr
    1580                1585            1590

Gly Tyr Glu Ala Asp Met Val Glu Ala Asp Met Asp Leu Glu Ala
    1595                1600            1605

Glu Leu Gly Ile Asp Ser Ile Lys Arg Val Glu Ile Leu Ser Glu
    1610                1615            1620

Val Gln Gly Gln Leu Gly Val Glu Ala Lys Asp Val Asp Ala Leu
    1625                1630            1635

Ser Arg Thr Arg Thr Val Gly Glu Val Val Asp Ala Met Lys Ala
    1640                1645            1650

Glu Ile Val Ala Ala Ser Gly Gly Ser Ala Pro Ala Ala Ala Val
    1655                1660            1665

Pro Ser Ala Pro Ala Ala Ser Ala Ala Pro Thr Pro Ala Thr Ala
    1670                1675            1680

Pro Ser Ala Asp Leu Gln Ala Leu Leu Ser Lys Ala Glu Thr Val
    1685                1690            1695

Val Met Ala Val Leu Ala Ala Lys Thr Gly Tyr Glu Ala Asp Met
    1700                1705            1710

Val Glu Ala Asp Met Asp Leu Glu Ala Glu Leu Gly Ile Asp Ser
    1715                1720            1725

Ile Lys Arg Val Glu Ile Leu Ser Glu Val Gln Gly Gln Leu Gly
    1730                1735            1740

Val Glu Ala Lys Asp Val Asp Ala Leu Ser Arg Thr Arg Thr Val
    1745                1750            1755

Gly Glu Val Val Asp Ala Met Lys Ala Glu Ile Val Ala Ala Ser
    1760                1765            1770

Gly Gly Ser Ala Pro Ala Ala Pro Ser Ala Pro Ala Leu Leu Pro
    1775                1780            1785

Thr Leu Phe Gly Ser Glu Cys Glu Asp Leu Ser Leu Thr Phe Pro
    1790                1795            1800

Val Ile Thr Thr Leu Pro Leu Pro Ala Glu Leu Val Leu Ala Glu
    1805                1810            1815

Gly Gly Ala Arg Pro Val Val Val Val Asp Asp Gly Ser Ala Leu
```

```
                1820                1825                1830
Thr Ser  Ser Leu Val Ser  Ser  Leu Gly Asp Arg  Ala  Val Leu Leu
    1835                1840                1845
Gln Val  Gln Ser Ser Ser  Ala  Cys Ser Pro Arg  Ser  Thr Thr His
    1850                1855                1860
Lys Leu  Val Thr Val Ala  Asp  Arg Ser Glu Ala  Ala  Leu Gln Ala
    1865                1870                1875
Ala Leu  Thr Ser Val Glu  Ala  Gln Phe Gly Lys  Val  Gly Gly Phe
    1880                1885                1890
Val Phe  Gln Phe Gly Asp  Asp  Val Gln Ala Gln  Leu  Gly Trp
    1895                1900                1905
Ala Leu  Leu Ala Ala Lys  His  Leu Lys Thr Ser  Leu  Ser Glu Gln
    1910                1915                1920
Ile Glu  Gly Gly Arg Thr  Phe  Phe Val Ala Val  Ala  Arg Leu Asp
    1925                1930                1935
Gly Gln  Leu Gly Leu Ser  Gly  Lys Ser Thr Thr  Ala  Thr Val Asp
    1940                1945                1950
Leu Ser  Arg Ala Gln Gln  Gly  Ser Val Phe Gly  Leu  Cys Lys Thr
    1955                1960                1965
Leu Asp  Leu Glu Trp Pro  Ala  Val Phe Cys Arg  Gly  Ile Asp Leu
    1970                1975                1980
Ala Ala  Asp Leu Asp Ala  Ala  Gln Ala Ala Arg  Cys  Leu Leu Gly
    1985                1990                1995
Glu Leu  Ser Asp Pro Asp  Val  Ala Val Arg Glu  Ser  Gly Tyr Ser
    2000                2005                2010
Ala Ser  Gly Gln Arg Cys  Thr  Thr Thr Thr Lys  Ser  Leu Thr Thr
    2015                2020                2025
Gly Lys  Pro His Gln Pro  Ile  Ser Ser Ser Asp  Leu  Phe Leu Val
    2030                2035                2040
Ser Gly  Gly Ala Arg Gly  Ile  Thr Pro Leu Cys  Val  Arg Glu Leu
    2045                2050                2055
Ala Gln  Arg Val Gly Gly  Gly  Thr Tyr Val Leu  Ile  Gly Arg Ser
    2060                2065                2070
Glu Leu  Pro Thr Thr Glu  Pro  Ala Trp Ala Val  Gly  Val Glu Ser
    2075                2080                2085
Gly Lys  Pro Leu Glu Lys  Ala  Ala Leu Ala Phe  Leu  Lys Ala Glu
    2090                2095                2100
Phe Ala  Ala Gly Arg Gly  Ala  Lys Pro Thr Pro  Met  Leu His Lys
    2105                2110                2115
Lys Leu  Val Gly Ala Val  Val  Gly Ala Arg Glu  Val  Arg Ala Ser
    2120                2125                2130
Leu Ala  Glu Ile Thr Ala  Gln  Gly Ala Thr Ala  Val  Tyr Glu Ser
    2135                2140                2145
Cys Asp  Val Ser Ser Ala  Ala  Lys Val Arg Glu  Met  Val Glu Arg
    2150                2155                2160
Val Gln  Gln Gln Gly Gly  Arg  Arg Val Ser Gly  Val  Phe His Ala
    2165                2170                2175
Ser Gly  Val Leu Arg Asp  Lys  Leu Val Glu Asn  Lys  Ser Leu Ala
    2180                2185                2190
Asp Phe  Ser Ala Val Tyr  Asp  Thr Lys Val Gly  Leu  Ile Asn
    2195                2200                2205
Leu Leu  Ala Cys Val Asp  Leu  Ala Gln Leu Arg  His  Leu Val Leu
    2210                2215                2220
```

```
Phe Ser Ser Leu Ala Gly Phe His Gly Asn Val Gly Gln Ser Asp
2225                2230                2235

Tyr Ala Met Ala Asn Glu Ala Leu Asn Lys Leu Ala Ala His Leu
2240                2245                2250

Ser Ala Val His Pro Gln Leu Cys Ala Arg Ser Ile Cys Phe Gly
2255                2260                2265

Pro Trp Asp Gly Gly Met Val Thr Pro Ala Leu Lys Ala Asn Phe
2270                2275                2280

Ile Arg Met Gly Ile Gln Ile Ile Pro Arg Gln Gly Gly Ala Gln
2285                2290                2295

Thr Val Ala Asn Met Leu Val Ser Ser Ser Pro Gly Gln Leu Leu
2300                2305                2310

Val Gly Asn Trp Gly Val Pro Pro Val Val Pro Ser Ala Thr Glu
2315                2320                2325

His Thr Val Leu Gln Thr Leu Arg Gln Ser Asp Asn Pro Phe Leu
2330                2335                2340

Asp Ser His Val Ile Gln Gly Arg Arg Val Leu Pro Met Thr Leu
2345                2350                2355

Ala Val Gly Tyr Met Ala His Gln Ala Gln Ser Ile Tyr Ala Gly
2360                2365                2370

His Gln Leu Trp Ala Val Glu Asp Ala Gln Leu Phe Lys Gly Ile
2375                2380                2385

Ala Ile Asp Asn Gly Ala Asp Val Pro Val Arg Val Glu Leu Ser
2390                2395                2400

Arg Arg Lys Glu Glu Gln Glu Asp Ala Gly Lys Val Lys Val Lys
2405                2410                2415

Val Gln Val Leu Leu Lys Ser Gln Val Asn Gly Lys Ser Val Pro
2420                2425                2430

Ala Tyr Lys Ala Thr Val Val Leu Ser Pro Ala Pro Arg Pro Ser
2435                2440                2445

Val Ile Thr Arg Asp Phe Asp Leu Thr Pro Asp Pro Ala Cys Thr
2450                2455                2460

Glu His Asp Leu Tyr Asp Gly Lys Thr Leu Phe His Gly Lys Ala
2465                2470                2475

Phe Gln Gly Ile Glu Gln Val Leu Ser Ala Thr Pro Lys Gln Leu
2480                2485                2490

Thr Ala Lys Cys Arg Asn Leu Pro Leu Thr Pro Glu Gln Arg Gly
2495                2500                2505

Gln Phe Val Val Asn Leu Ser Gln Gln Asp Pro Phe Gln Ala Asp
2510                2515                2520

Ile Ala Phe Gln Ala Met Leu Val Trp Ala Arg Met Leu Arg Gln
2525                2530                2535

Ser Ala Ala Leu Pro Asn Asn Cys Glu Arg Phe Asp Phe Tyr Lys
2540                2545                2550

Pro Met Ala Pro Gly Ala Thr Tyr Tyr Thr Ser Val Lys Leu Ala
2555                2560                2565

Ser Ala Ser Pro Leu Val Asp Ser Val Cys Lys Cys Thr Val Ala
2570                2575                2580

Met His Asp Glu Gln Gly Glu Val Tyr Phe Ser Ala Arg Ala Ser
2585                2590                2595

Val Val Leu Asn Lys Thr Leu Thr Tyr
2600                2605
```

<210> SEQ ID NO 3
<211> LENGTH: 5778
<212> TYPE: DNA
<213> ORGANISM: Schizochytrium sp.

<400> SEQUENCE: 3

| | | | | | | |
|---|---|---|---|---|---|---|
| atgccgtgcg | ataacattgc | ggtcgtgggc | atggcggtgc | agtatgccgg | atgcaagaac | 60 |
| caggacgagt | tctgggatac | gctgatgcgt | aaggagatca | actcgagccc | gatctcggcg | 120 |
| gagcgcctcg | gtacgcgcta | ccgcgacctc | cacttccacc | cgcagcgcag | caagtacgcc | 180 |
| gacaccttct | gcaacgatcg | ctacggctgc | gtcgatgcca | gcgtcgacaa | cgagcacgac | 240 |
| ctcctcgccg | acctggcccg | gcgcgccctg | ctcgacgccg | gaattaacct | cgacgacgcc | 300 |
| agcaccaccg | ccaacctacg | cgacttcggc | atcgtgagcg | gctgcctgtc | gttccccatg | 360 |
| gacaatctgc | agggcgagct | gctcaatctg | taccaagtgc | atgtggagaa | ccgcgtgggc | 420 |
| gcccagcgct | tccgcgactc | cgcccctgg | tcggagcgcc | cgcgcgctgt | ctcgcccgag | 480 |
| gccagcgacc | cgcgcgtgta | ctccgacccg | gcgtccttcg | tggccaacca | gctcggcctg | 540 |
| gggcccgtgc | gctacagcct | cgatgcagcc | tgcgcgtcgg | cgctgtactg | cctcaagctg | 600 |
| gcgtccgacc | acttgctctc | gcgcagcgcg | gacgtgatgc | tgtgcggcgc | cacatgcttt | 660 |
| ccggacccgt | tcttcattct | ctcggggttc | tccaccttcc | aggcgatgcc | gctgggcgga | 720 |
| ccggacgata | acccactgtc | cgtgccgctg | cggcagggca | gccagggcct | gacgcccgga | 780 |
| gagggcggcg | ccatcatggt | gctgaagcgc | ctcgaggacg | ccgtgcgcga | cggcgaccgc | 840 |
| atctacggca | ccttgctcgg | cacgagtctg | agcaacgccg | ggtgcggcct | gccgctgagc | 900 |
| ccgcacctgc | cgagcgagaa | gtcgtgcatg | gaggacctgt | acacgagcgt | cggcatcgac | 960 |
| ccaagcgagg | tgcagtacgt | ggagtgccac | gccacgggca | ctccgcaggg | cgacgtcgtg | 1020 |
| gaggtagagg | cgctgcgcca | ctgctttcga | ggtaacacgg | accaccgcc | gcgcatgggc | 1080 |
| tccaccaagg | gcaactttgg | ccacactctc | gtggcggccg | ggttcgcagg | catggccaag | 1140 |
| gtgctgctgt | cgatgcagca | cggcacgatc | ccgcccacgc | ccggtgtcga | ccgctccaac | 1200 |
| tgcatcgacc | cgctcgtcgt | ggacgaggcc | atcccttggc | cgtactcgtc | ggcgcaggcg | 1260 |
| cgggcaggca | aaccaggcga | tgagctcaag | tgcgcctcgc | tctccgcctt | tggctttggt | 1320 |
| ggaaccaacg | cgcactgtgt | cttccgtgag | caccgccaaa | ttgctgctac | tgcgacagcc | 1380 |
| tcgccggtgc | ttcccgaggt | gactcctgga | ccgattgcca | tcatcgggat | ggacgcgacg | 1440 |
| tttggtaccc | tcaagggcct | ggacgcgttt | gagcaggcca | tctacaaggg | cacggacggc | 1500 |
| gccagcgacc | tgccgagcaa | gcgctggcgg | ttcctgggcg | ccgacacgga | cttcttgacc | 1560 |
| gccatgggcc | tcgacgccgt | gccgcgcggg | tgctacgtgc | gcgacgtgga | cgtggactac | 1620 |
| aagcggctgc | ggtcgccgat | gatccctgag | gacgtcctgc | gcccgcaaca | gctgctggcg | 1680 |
| gtggctacga | tggaccgcgc | gctgcaggac | gctggaatgg | cgacgggagg | caaggtggcg | 1740 |
| gtgctggtgg | ggctcggcac | ggacaccgag | ctgtaccggc | accgcgcgcg | cgtgacactc | 1800 |
| aaggagcggc | tcgacccggc | cgcgttctcg | cccgagcagg | tgcaggagat | gatggactac | 1860 |
| atcaacgact | gcggcacctc | gacgtcgtac | acgtcgtaca | tcggcaacct | cgtgccacg | 1920 |
| cgcgtgtcct | cgcagtgggg | ctttacgggc | ccgtccttca | ccgtcaccga | aggcgcaaac | 1980 |
| tcggtctacc | gctgcctcga | gctgggcaag | ttcctgctcg | acacgcacca | ggtgacgcc | 2040 |
| gtcgtggtgg | ccggcgtcga | cctctgtgcc | accgccgaga | acctttacct | caaggcgcgc | 2100 |
| cgctccgcca | tcagccgaca | ggaccaccct | cgcgccaact | tgaggccag | cgccgacggg | 2160 |

```
tactttgccg gcgagggcag cggcgccctg gtcctcaagc gccaggccga cgttggctca    2220
gacgacaagg tctacgccag tgtcgcgggc ctcacgtgcg ccgcgcagcc cgctgaagcc    2280
gtgtcgccgc tactactcca agtccacaac gacgacaacg agaagagggt ggtggagatg    2340
gtggagctcg ccgccgactc gggtcgccat gcgccgcact tggccaactc gccgctgagc    2400
gccgagtcgc agctggagca agtgtccaag ttgctcgcgc accaggtgcc gggctcggtg    2460
gccatcggca gcgtgcgcgc caacgtggga gacgtcgggt acgcctcggg cgccgcgagc    2520
ctcatcaaga cggcgctgtg cctccacaac cgctacctcc cggccaaccc gcagtgggag    2580
cggccggtgg cgccggtctc cgaggcgctg tttacttgcc cgcgctcgcg tgcctggctg    2640
aagaacccgg gcgagtcgcg actggcggct gtcgccagtg cctccgagag cgggtcctgc    2700
tttggcgtgc tcctcacaga cgagtacgcc actcatgaga gcagcaaccg cctctcgctg    2760
gatgacgccg cccccaagct catcgcgatc cgtggcgaca ccgttgacga tatcatggcc    2820
aaggtcaacg ccgagctggc gctcctccga gcgcacgccg aaaccgggtc tgctactgac    2880
gacgacccag ctgctgctgt cgcttttcact gctcatcgct tgcgcttttt gcggctcgta    2940
ggggagacgg tggctagtca cggtgccacg gcgaccttgt gtttggccct gctgacaacg    3000
ccggagaagc tggagaagga gttggagctg gcagccaagg gtgtaccgcg aagcgccaag    3060
gccgggcgca actggatgtc gccatcgggc agcgcctttg cgccgacacc tgtgaccagc    3120
gaccgcgtcg cgttcatgta cggcgagggc cgcagcccct actacggcgt cgggctcgac    3180
ctgcaccgcc tgtggccggc tttgcacgag cgcatcaacg acaagaccgc ggcgctgtgg    3240
gagaacggcg actcgtggct catgccgcgc gcggtggatg ccgactcgca gcgcgccgtg    3300
cagacggcct ttgacgcgga ccagatcgag atgttccgca cgggcatctt cgtgtccatc    3360
tgcctcaccg actacgcgcg cgacgtgctc ggggtgcagc ccaaggcgtg cttcggcctc    3420
agcctcggcg agatctccat gctctttgcg ctgtcgcgac gcaactgcgg cctgtcggac    3480
cagctcacgc agcgcctacg cacctcgccg gtgtggtcga cacagctggc ggtggagttc    3540
caggccttgc gcaagctatg gaacgtgccg gcggacgccc ccgtggagtc cttctggcag    3600
ggctacttgg ttcgcgccag ccgcgccgaa atcgagaagg cgatcgggcc cgacaaccgc    3660
ttcgtgcgcc tgctgatcgt caacgactcg agcagcgcgc tgatcgccgg caaacctgcc    3720
gagtgtctgc gcgtgctgga gcgcctgggc gggcggttgc cgccgatgcc cgtcaagcaa    3780
ggcatgattg ggcactgccc cgaagtggcg ccctacacgc cgggcatcgc gcacatccac    3840
gagattttgg agattccgga cagccccgtc aagatgtaca cctcggtcac caacgccgag    3900
ctgcgcgggg gcagcaacag cagcatcacc gagttcgtgc agaagttgta cacgcgcatc    3960
gccgactttc cgggcatcgt cgacaaggtc agccgtgacg gccacgatgt cttcgtcgag    4020
gtggggccga acaacatgcg ctccgccgcg gtcagtgaca ttcttggcaa ggctgccacc    4080
ccgcatgtct ccgtggcgct ggaccgcccc agtgagtcgg cgtggacgca gaccctcaag    4140
tcgctggcgc tgctgaccgc ccaccgcgtg cccctgcaca acccgactct gtttgcggac    4200
ctgtaccacc ccacgttcct gacggctatc gactctgcga tgcaggagcc cccgcccaag    4260
cccaaccgct tccttcgcag cgtagaggtc aacgggtact tttgccccga cggcatcagc    4320
aagcaggttg ctgctgcaag tgccaaaccc tcgacgcatt gcatggttcg tttgcaccca    4380
gccaaggcag ttgtggttgc tgctgctggt gctgtggttg ctgattcgac gcccgtggtc    4440
aaggccaagc agacgtcgtc gtcgttgttg gttggggatg acgcctttct gcgctgctac    4500
```

-continued

```
gacgtggact ggccgctcta catgggcgcc atggcggaag gcatctcgtc ggtagacctg      4560
gtggtcgctg ccgccgaggc ccgcatgctg catcattcg  gagcggcccg cttgcctatg      4620
gaccaggtgg aactccagat ccgtgagatc cagcaacgca cctccaacgc ctttgctgtc      4680
aacctgatgc cgggtcctga cgaggccgcg acggtggacg cgctgctgcg cacgggcgtc      4740
tcaatcgtcg aggcatcggg ctacaccggc gcgctctctg cagacctggt gcgctaccgt      4800
gtcacgggtc tgcgacgaac tagttgcggt gcttctgtgt cggcgactca ccgtgtggtc      4860
gccaaggtgt cgcgcaccga ggtggccgag cactttctgc cccggcgcc  ggccgccgta      4920 ctagaggctt tggtcgccgc caaacagatt acgcccgagc aggccgcgct ggccagccgc      4980
gtcgccatgg ccgacgacgt cgcggtggag ccgactcgg  gcgggcacac cgacaaccga      5040
ccgatccacg tgctgctgcc gctcgtggtg gcgcagcgca accgctgcg  ccacctggtg      5100 gacacgccag tgcgcgtcgg cgccggcggc gggatcgcct gtccgcgcgc cgcgctgctc      5160
gccttttccc tgggcgccgc ctttgtggtc accgggtccg tcaaccaact ggcccgcgag      5220
gctggcacca gcgacgcggt ccgactactg ctggcgacgg ccacctactc ggacgtggcc      5280
atggcgccgg gcggcgtcca ggtgctcaag aagcagacca tgttcgccgc gcgggccacg      5340
atgctcgccc agctgcaggc caagttcggc tcctttgacg ccgtgccgga ccgcagctg       5400 cgcaagctcg agcgctccgt gttcaagcag tccgtggcgg acgtgtgggc tgctgcacgc      5460
gaaaagtttg tgtcgacgc  taccgctgca agtccgcagg agaggatggc gctctgtgtg      5520
cgctggtaca tgtcgcagtc gtcgcgatgg gctaccgagg cgacgtccgc gcgcaaggcg      5580
gactaccaga tctggtgcgg ccccgccatc ggcagcttca acgacttcgt tcgcggcacc      5640
aagctggacg cgaccgctgg caccggcgag tttccgcgcg tcgtggacat caaccagcac      5700
atcctcctcg gagcctcgca ctaccgccgc gtgcagcaac aacaacagga cgacgacgta      5760
gaatacatca tcgtataa                                                   5778
```

<210> SEQ ID NO 4
<211> LENGTH: 1925
<212> TYPE: PRT
<213> ORGANISM: Schizochytrium sp.

<400> SEQUENCE: 4

```
Met Pro Cys Asp Asn Ile Ala Val Val Gly Met Ala Val Gln Tyr Ala
1               5                   10                  15

Gly Cys Lys Asn Gln Asp Glu Phe Trp Asp Thr Leu Met Arg Lys Glu
            20                  25                  30

Ile Asn Ser Ser Pro Ile Ser Ala Glu Arg Leu Gly Thr Arg Tyr Arg
        35                  40                  45

Asp Leu His Phe His Pro Gln Arg Ser Lys Tyr Ala Asp Thr Phe Cys
    50                  55                  60

Asn Asp Arg Tyr Gly Cys Val Asp Ala Ser Val Asp Asn Glu His Asp
65                  70                  75                  80

Leu Leu Ala Asp Leu Ala Arg Arg Ala Leu Asp Ala Gly Ile Asn
            85                  90                  95

Leu Asp Asp Ala Ser Thr Thr Ala Asn Leu Arg Asp Phe Gly Ile Val
            100                 105                 110

Ser Gly Cys Leu Ser Phe Pro Met Asp Asn Leu Gln Gly Glu Leu Leu
        115                 120                 125

Asn Leu Tyr Gln Val His Val Glu Asn Arg Val Gly Ala Gln Arg Phe
    130                 135                 140
```

```
Arg Asp Ser Arg Pro Trp Ser Glu Arg Pro Arg Ala Val Ser Pro Glu
145                 150                 155                 160

Ala Ser Asp Pro Arg Val Tyr Ser Asp Pro Ala Ser Phe Val Ala Asn
            165                 170                 175

Gln Leu Gly Leu Gly Pro Val Arg Tyr Ser Leu Asp Ala Ala Cys Ala
        180                 185                 190

Ser Ala Leu Tyr Cys Leu Lys Leu Ala Ser Asp His Leu Leu Ser Arg
    195                 200                 205

Ser Ala Asp Val Met Leu Cys Gly Ala Thr Cys Phe Pro Asp Pro Phe
    210                 215                 220

Phe Ile Leu Ser Gly Phe Ser Thr Phe Gln Ala Met Pro Leu Gly Gly
225                 230                 235                 240

Pro Asp Asp Asn Pro Leu Ser Val Pro Leu Arg Gln Gly Ser Gln Gly
            245                 250                 255

Leu Thr Pro Gly Glu Gly Gly Ala Ile Met Val Leu Lys Arg Leu Glu
            260                 265                 270

Asp Ala Val Arg Asp Gly Asp Arg Ile Tyr Gly Thr Leu Leu Gly Thr
            275                 280                 285

Ser Leu Ser Asn Ala Gly Cys Gly Leu Pro Leu Ser Pro His Leu Pro
    290                 295                 300

Ser Glu Lys Ser Cys Met Glu Asp Leu Tyr Thr Ser Val Gly Ile Asp
305                 310                 315                 320

Pro Ser Glu Val Gln Tyr Val Glu Cys His Ala Thr Gly Thr Pro Gln
                325                 330                 335

Gly Asp Val Val Glu Val Glu Ala Leu Arg His Cys Phe Arg Gly Asn
            340                 345                 350

Thr Asp His Pro Pro Arg Met Gly Ser Thr Lys Gly Asn Phe Gly His
            355                 360                 365

Thr Leu Val Ala Ala Gly Phe Ala Gly Met Ala Lys Val Leu Leu Ser
        370                 375                 380

Met Gln His Gly Thr Ile Pro Pro Thr Pro Gly Val Asp Arg Ser Asn
385                 390                 395                 400

Cys Ile Asp Pro Leu Val Val Asp Glu Ala Ile Pro Trp Pro Tyr Ser
            405                 410                 415

Ser Ala Gln Ala Arg Ala Gly Lys Pro Gly Asp Glu Leu Lys Cys Ala
            420                 425                 430

Ser Leu Ser Ala Phe Gly Phe Gly Gly Thr Asn Ala His Cys Val Phe
        435                 440                 445

Arg Glu His Arg Gln Ile Ala Thr Ala Thr Ala Ser Pro Val Leu
    450                 455                 460

Pro Glu Val Thr Pro Gly Pro Ile Ala Ile Gly Met Asp Ala Thr
465                 470                 475                 480

Phe Gly Thr Leu Lys Gly Leu Asp Ala Phe Glu Gln Ala Ile Tyr Lys
            485                 490                 495

Gly Thr Asp Gly Ala Ser Asp Leu Pro Ser Lys Arg Trp Arg Phe Leu
        500                 505                 510

Gly Ala Asp Thr Asp Phe Leu Thr Ala Met Gly Leu Asp Ala Val Pro
        515                 520                 525

Arg Gly Cys Tyr Val Arg Asp Val Asp Val Asp Tyr Lys Arg Leu Arg
        530                 535                 540

Ser Pro Met Ile Pro Glu Asp Val Leu Arg Pro Gln Gln Leu Leu Ala
545                 550                 555                 560

Val Ala Thr Met Asp Arg Ala Leu Gln Asp Ala Gly Met Ala Thr Gly
```

```
            565                 570                 575
Gly Lys Val Ala Val Leu Val Gly Leu Gly Thr Asp Thr Glu Leu Tyr
            580                 585                 590

Arg His Arg Ala Arg Val Thr Leu Lys Glu Arg Leu Asp Pro Ala Ala
            595                 600                 605

Phe Ser Pro Glu Gln Val Gln Glu Met Met Asp Tyr Ile Asn Asp Cys
            610                 615                 620

Gly Thr Ser Thr Ser Tyr Thr Ser Tyr Ile Gly Asn Leu Val Ala Thr
625                 630                 635                 640

Arg Val Ser Ser Gln Trp Gly Phe Thr Gly Pro Ser Phe Thr Val Thr
                    645                 650                 655

Glu Gly Ala Asn Ser Val Tyr Arg Cys Leu Glu Leu Gly Lys Phe Leu
                    660                 665                 670

Leu Asp Thr His Gln Val Asp Ala Val Val Ala Gly Val Asp Leu
            675                 680                 685

Cys Ala Thr Ala Glu Asn Leu Tyr Leu Lys Ala Arg Arg Ser Ala Ile
            690                 695                 700

Ser Arg Gln Asp His Pro Arg Ala Asn Phe Glu Ala Ser Ala Asp Gly
705                 710                 715                 720

Tyr Phe Ala Gly Glu Gly Ser Gly Ala Leu Val Leu Lys Arg Gln Ala
                    725                 730                 735

Asp Val Gly Ser Asp Lys Val Tyr Ala Ser Val Ala Gly Leu Thr
            740                 745                 750

Cys Ala Ala Gln Pro Ala Glu Ala Val Ser Pro Leu Leu Gln Val
            755                 760                 765

His Asn Asp Asp Asn Glu Lys Arg Val Val Glu Met Val Glu Leu Ala
770                 775                 780

Ala Asp Ser Gly Arg His Ala Pro His Leu Ala Asn Ser Pro Leu Ser
785                 790                 795                 800

Ala Glu Ser Gln Leu Glu Gln Val Ser Lys Leu Leu Ala His Gln Val
            805                 810                 815

Pro Gly Ser Val Ala Ile Gly Ser Val Arg Ala Asn Val Gly Asp Val
            820                 825                 830

Gly Tyr Ala Ser Gly Ala Ala Ser Leu Ile Lys Thr Ala Leu Cys Leu
            835                 840                 845

His Asn Arg Tyr Leu Pro Ala Asn Pro Gln Trp Glu Arg Pro Val Ala
            850                 855                 860

Pro Val Ser Glu Ala Leu Phe Thr Cys Pro Arg Ser Arg Ala Trp Leu
865                 870                 875                 880

Lys Asn Pro Gly Glu Ser Arg Leu Ala Ala Val Ala Ser Ala Ser Glu
                    885                 890                 895

Ser Gly Ser Cys Phe Gly Val Leu Leu Thr Asp Glu Tyr Ala Thr His
            900                 905                 910

Glu Ser Ser Asn Arg Leu Ser Leu Asp Asp Ala Ala Pro Lys Leu Ile
            915                 920                 925

Ala Ile Arg Gly Asp Thr Val Asp Ile Met Ala Lys Val Asn Ala
930                 935                 940

Glu Leu Ala Leu Leu Arg Ala His Ala Glu Thr Gly Ser Ala Thr Asp
945                 950                 955                 960

Asp Asp Pro Ala Ala Val Ala Phe Thr Ala His Arg Leu Arg Phe
            965                 970                 975

Leu Arg Leu Val Gly Glu Thr Val Ala Ser His Gly Ala Thr Ala Thr
            980                 985                 990
```

```
Leu Cys Leu Ala Leu Leu Thr Thr  Pro Glu Lys Leu Glu  Lys Glu Leu
        995                 1000                1005

Glu Leu Ala Ala Lys Gly Val Pro Arg Ser Ala Lys  Ala Gly Arg
    1010            1015                1020

Asn Trp Met Ser Pro Ser Gly  Ser Ala Phe Ala Pro  Thr Pro Val
    1025                1030                1035

Thr Ser Asp Arg Val Ala Phe  Met Tyr Gly Glu Gly  Arg Ser Pro
    1040                1045                1050

Tyr Tyr Gly Val Gly Leu Asp  Leu His Arg Leu Trp  Pro Ala Leu
    1055                1060                1065

His Glu Arg Ile Asn Asp Lys  Thr Ala Ala Leu Trp  Glu Asn Gly
    1070                1075                1080

Asp Ser Trp Leu Met Pro Arg  Ala Val Asp Ala Asp  Ser Gln Arg
    1085                1090                1095

Ala Val Gln Thr Ala Phe Asp  Ala Asp Gln Ile Glu  Met Phe Arg
    1100                1105                1110

Thr Gly Ile Phe Val Ser Ile  Cys Leu Thr Asp Tyr  Ala Arg Asp
    1115                1120                1125

Val Leu Gly Val Gln Pro Lys  Ala Cys Phe Gly Leu  Ser Leu Gly
    1130                1135                1140

Glu Ile Ser Met Leu Phe Ala  Leu Ser Arg Arg Asn  Cys Gly Leu
    1145                1150                1155

Ser Asp Gln Leu Thr Gln Arg  Leu Arg Thr Ser Pro  Val Trp Ser
    1160                1165                1170

Thr Gln Leu Ala Val Glu Phe  Gln Ala Leu Arg Lys  Leu Trp Asn
    1175                1180                1185

Val Pro Ala Asp Ala Pro Val  Glu Ser Phe Trp Gln  Gly Tyr Leu
    1190                1195                1200

Val Arg Ala Ser Arg Ala Glu  Ile Glu Lys Ala Ile  Gly Pro Asp
    1205                1210                1215

Asn Arg Phe Val Arg Leu Leu  Ile Val Asn Asp Ser  Ser Ser Ala
    1220                1225                1230

Leu Ile Ala Gly Lys Pro Ala  Glu Cys Leu Arg Val  Leu Glu Arg
    1235                1240                1245

Leu Gly Gly Arg Leu Pro Pro  Met Pro Val Lys Gln  Gly Met Ile
    1250                1255                1260

Gly His Cys Pro Glu Val Ala  Pro Tyr Thr Pro Gly  Ile Ala His
    1265                1270                1275

Ile His Glu Ile Leu Glu Ile  Pro Asp Ser Pro Val  Lys Met Tyr
    1280                1285                1290

Thr Ser Val Thr Asn Ala Glu  Leu Arg Gly Gly Ser  Asn Ser Ser
    1295                1300                1305

Ile Thr Glu Phe Val Gln Lys  Leu Tyr Thr Arg Ile  Ala Asp Phe
    1310                1315                1320

Pro Gly Ile Val Asp Lys Val  Ser Arg Asp Gly His  Asp Val Phe
    1325                1330                1335

Val Glu Val Gly Pro Asn Asn  Met Arg Ser Ala Ala  Val Ser Asp
    1340                1345                1350

Ile Leu Gly Lys Ala Ala Thr  Pro His Val Ser Val  Ala Leu Asp
    1355                1360                1365

Arg Pro Ser Glu Ser Ala Trp  Thr Gln Thr Leu Lys  Ser Leu Ala
    1370                1375                1380
```

```
Leu Leu Thr Ala His Arg Val Pro Leu His Asn Pro Thr Leu Phe
    1385                1390                1395

Ala Asp Leu Tyr His Pro Thr Phe Leu Thr Ala Ile Asp Ser Ala
    1400                1405                1410

Met Gln Glu Pro Pro Lys Pro Asn Arg Phe Leu Arg Ser Val
    1415                1420                1425

Glu Val Asn Gly Tyr Phe Cys Pro Asp Gly Ile Ser Lys Gln Val
    1430                1435                1440

Ala Ala Ala Ser Ala Lys Pro Ser Thr His Cys Met Val Arg Leu
    1445                1450                1455

His Pro Ala Lys Ala Val Val Ala Ala Ala Gly Ala Val Val
    1460                1465                1470

Ala Asp Ser Thr Pro Val Val Lys Ala Lys Gln Thr Ser Ser Ser
    1475                1480                1485

Leu Leu Val Gly Asp Asp Ala Phe Leu Arg Cys Tyr Asp Val Asp
    1490                1495                1500

Trp Pro Leu Tyr Met Gly Ala Met Ala Glu Gly Ile Ser Ser Val
    1505                1510                1515

Asp Leu Val Val Ala Ala Glu Ala Arg Met Leu Ala Ser Phe
    1520                1525                1530

Gly Ala Ala Arg Leu Pro Met Asp Gln Val Glu Leu Gln Ile Arg
    1535                1540                1545

Glu Ile Gln Gln Arg Thr Ser Asn Ala Phe Ala Val Asn Leu Met
    1550                1555                1560

Pro Gly Pro Asp Glu Ala Ala Thr Val Asp Ala Leu Leu Arg Thr
    1565                1570                1575

Gly Val Ser Ile Val Glu Ala Ser Gly Tyr Thr Gly Ala Leu Ser
    1580                1585                1590

Ala Asp Leu Val Arg Tyr Arg Val Thr Gly Leu Arg Arg Thr Ser
    1595                1600                1605

Cys Gly Ala Ser Val Ser Ala Thr His Arg Val Val Ala Lys Val
    1610                1615                1620

Ser Arg Thr Glu Val Ala Glu His Phe Leu Arg Pro Ala Pro Ala
    1625                1630                1635

Ala Val Leu Glu Ala Leu Val Ala Ala Lys Gln Ile Thr Pro Glu
    1640                1645                1650

Gln Ala Ala Leu Ala Ser Arg Val Ala Met Ala Asp Asp Val Ala
    1655                1660                1665

Val Glu Ala Asp Ser Gly Gly His Thr Asp Asn Arg Pro Ile His
    1670                1675                1680

Val Leu Leu Pro Leu Val Val Ala Gln Arg Asn Arg Trp Arg His
    1685                1690                1695

Leu Val Asp Thr Pro Val Arg Val Gly Ala Gly Gly Ile Ala
    1700                1705                1710

Cys Pro Arg Ala Ala Leu Leu Ala Phe Ser Leu Gly Ala Ala Phe
    1715                1720                1725

Val Val Thr Gly Ser Val Asn Gln Leu Ala Arg Glu Ala Gly Thr
    1730                1735                1740

Ser Asp Ala Val Arg Leu Leu Leu Ala Thr Ala Thr Tyr Ser Asp
    1745                1750                1755

Val Ala Met Ala Pro Gly Gly Val Gln Val Leu Lys Lys Gln Thr
    1760                1765                1770

Met Phe Ala Ala Arg Ala Thr Met Leu Ala Gln Leu Gln Ala Lys
```

|  | 1775 |  |  | 1780 |  |  |  | 1785 |  |  |
|---|---|---|---|---|---|---|---|---|---|---|

Phe Gly Ser Phe Asp Ala Val Pro Glu Pro Gln Leu Arg Lys Leu
      1790                  1795                 1800

Glu Arg Ser Val Phe Lys Gln Ser Val Ala Asp Val Trp Ala Ala
    1805                  1810                 1815

Ala Arg Glu Lys Phe Gly Val Asp Ala Thr Ala Ala Ser Pro Gln
    1820                  1825                 1830

Glu Arg Met Ala Leu Cys Val Arg Trp Tyr Met Ser Gln Ser Ser
    1835                  1840                 1845

Arg Trp Ala Thr Glu Ala Thr Ser Ala Arg Lys Ala Asp Tyr Gln
    1850                  1855                 1860

Ile Trp Cys Gly Pro Ala Ile Gly Ser Phe Asn Asp Phe Val Arg
    1865                  1870                 1875

Gly Thr Lys Leu Asp Ala Thr Ala Gly Thr Gly Glu Phe Pro Arg
    1880                  1885                 1890

Val Val Asp Ile Asn Gln His Ile Leu Leu Gly Ala Ser His Tyr
    1895                  1900                 1905

Arg Arg Val Gln Gln Gln Gln Asp Asp Asp Val Glu Tyr Ile
    1910                  1915                 1920

Ile Val
    1925

```
<210> SEQ ID NO 5
<211> LENGTH: 4308
<212> TYPE: DNA
<213> ORGANISM: Schizochytrium sp.

<400> SEQUENCE: 5
atgacatcat cgaagaagac tcccgtgtgg gagatgagca aggaggagct gctggacggc        60
aagacggtgg tcttcgacta caacgagctg ctcgaattcg ccgagggcga cgtgggccaa       120
gtgttcggac ccgagttcga catcatcgac aagtaccggc gtcgcgtgcg gctgccggcg       180
cgcgagtacc tgctcgtgtc gcgcgtgacg ctgatggacg ccgaggtgaa caacttccgc       240
gtcgggtcgc gcatggtgac cgagtacgac gtgcccgtga acggggagct gtcggagggc       300
ggggacgtgc cgtgggcggt gctggtggag tcggggcagt gcgacctgat gctcatctcg       360
tacatgggca tcgacttcca gtgcaagggc gaccgcgtgt accgcctgct caacacatcg       420
ctcaccttct tcggggtggc gcacgagggc gagacgctgg tgtacgacat ccgcgtcacg       480
gggttcgcca agggcgcggg cggggagatc tcgatgttct tcttcgagta cgactgcttc       540
gtggacggcc gcctgctgat cgagatgcgc gacgggtgcg ccgggttctt cacggacgcc       600
gagctggccg ccggcaaggg cgtgcttaag accaaggcgg agctggcggc gcgcgcgcag       660
atccagaagc aggacatcgc gcccttttgcg ccggcgccgt gctcgcacaa gacctcgctg       720
gacgcgcgcg agatgcggct gctcgtggac cgccagtggg cgcgcgtctt cggcagcggc       780
atggcgggca tcgactacaa gttgtgcgct cgcaagatgc tcatgatcga ccgcgtcacg       840
cacctcgacc cgcgcggcgg cgcgcacggc ctcgggctgc tgatcgggga aaggtgctg       900 gagcgcgacc actggtactt ccctgccac tttgtgcgcg acgaggtgat ggccgggtcg       960
ctggtcagcg acgctgctc gcagctcctc aaggtgtaca tgctgtggct cggcctgcac      1020
acgaccgtgg gcgcgttcga ctttcgtccc gtgagcgggc acgccaacaa ggtgcggtgc      1080
cgcgggcaga tctcaccgca aagggcaag ctcgtgtacg tgatggagat caggaaatg      1140 ggctttgacg cgaagacggg cgatccgttt gcgatcgcgg acgtggacat catcgacgtc      1200
```

```
aacttcgagg agggacaggc gtttgcggga gtggaagacc tgcacagcta cggccagggc    1260
gacctccgca agaagatcgt cgtcgacttc aagggcatcg cgctctccct gcagaagcgg    1320
aaggagcagc agaaggaaag catgaccgtg actacgacga cgacgacgac gagccgggtg    1380
attgcgccgc ccagcgggtg cctcaagggc gacccgacgg cgccgacgag cgtgacgtgg    1440
cacccgatgg cggagggcaa cggcgggccc ggaccgacgc cgtcgttctc gccgtccgcg    1500
tacccgccgc gggcggtgtg cttctcgccg ttccccaaca acccgcttga caacgaccac    1560
acgccgggcc agatgccgtt gacctggttc aacatgtccg aattcatgtg cggcaaagtg    1620
tccaactgcc tgggccccga gtttgcgcgc ttcgacgcga gcaagacgag ccgcagcccg    1680
gcctttgacc tggcgctcgt gacgcgggtg acgagcgtgg cggacatgga gcacgggccg    1740
ttctacaacg tggacgtcaa cccgggccag ggcacgatgt gggcgagtt cgactgtccc    1800 gcggacgcgt ggttcttcgg cgcctcgagc cgcgacgacc acatgccgta ctcgatcctg    1860
atggagatcg cgctgcagac gtcgggcgtc ctcacctcgg tgctcaaggc gccgctgacg    1920
atggacaagg acgacatcct cttccgcaac ctcgacgcag cgccgagct cgtgggcgac    1980 gccatgccgg acgtgcgcgg caagacgatc cgcaacttca ccaagtgcac aggctacagc    2040
atgctcggca agatgggcat ccaccgcttc acctttgagc tcagcgtcga cggcgccgtc    2100
ttctacaagg gcagcacctc gtttggctgg ttcgtcccg aggtcttcga gtcgcagacc    2160
ggtctcgaca acggcaagcc gcgcctgcct tggtaccgcg agaacaacgt cgccgtcgac    2220
acgctctccg cgcccgcctc cgcttcctcc gcgcaaggtc agctgcagct gcagcgacgc    2280
gggtcgcagg cgcagttcct ggacacaatc cacctggcgg gcagcggcgc cggcgtgcac    2340
ggccagggct acgcgcacgg ggagaaggcc gtgaacaagc aagattggtt cttctcgtgc    2400
cacttctggt tcgaccccgt gatgcccggg tccctgggca tcgagtcgat gttccagctc    2460
gtcgaggcgt ggtgcgtgaa gcagggactc gcggcgcggc acggcatcgc tcacccagtg    2520
ttcgcgcacg cgcccggggc cacgagctgg aagtaccgcg ggcagctaac ccccaagaac    2580
gaccgcatgg acagcgaggt gcacatcaag tcggtggcgg ccttctcctc ctgggtcgac    2640
gtcgtcgcgg acgggttcct cttcgtcgac ggcctccgcg tctactcggc agacaacctc    2700
cgcgtccgca tccagaccgg cgccggccac gttgaagagc aagaggttgc tgccaaggcc    2760
acaaccaaga acagcagtat tgctgatgtg acgtggcgg acctgcaagc gctcaagcag    2820
gcgttgctga cgctggagcg accgctgcag ctggacgcgg ggagcgaggt gcccgcctgc    2880
gcggtgagcg acctgggcga taggggcttc atggagacgt acggggtggt ggcgccgctg    2940
tacagcgggg cgatggccaa gggcatcgcg tcggcggacc tggtgatcgc gatgggccag    3000
cgcaagatgc tggggtcgtt tggcgcggc gggctcccga tgcacgtcgt gcgcgcgggg    3060
attgagaaga tccaggcagc gctgccagcg gggccatacg cggtcaacct gattcactcg    3120 cctttttgacg ccaacctgga gaagggcaac gtggacctct tcctggagaa gggcgtgcgc    3180
gtcgtggagg cgtcggcctt catggagctc acgccccagg tggtgcgcta ccgcgcgacg    3240
ggcctctctc gcgacgcgcg cggcggctcc gtgcgcacgg cccacaagat catcggcaag    3300
gtcagccgca ccgagctggc cgagatgttt atccggcccg cgccgcaagc cattctcgac    3360
aagcttgtgg cgtccggcga gatcaccccc gagcaggcgg cgctggcgct cgaggtgccc    3420
atggcggacg acatcgccgt cgaggccgat cggcggggc acaccgacaa ccgcccatc    3480 cacgtcatcc tgcccctcat cctcagcctg cgcaaccgcc tccagcgcga gctcaagtac    3540
```

-continued

| | |
|---|---|
| cctgcgcgac accgcgtgcg cgtcggcgcc ggggcggca tcgggtgccc gcaagcggct | 3600 |
| ctgggcgcct tccacatggg cgccgcgttt gtggtgacgg gcacggtcaa ccagctgagc | 3660 |
| cggcaggccg ggacatgcga caatgtgcgg cggcagctgt cgcgcgcgac gtactcggac | 3720 |
| atcacgatgg cgccggcggc ggacatgttc gagcagggcg tcgagctgca ggtgctcaag | 3780 |
| aagggcacga tgtttccctc gcgcgccaag aagctgttcg agctgtttca caagtacgac | 3840 |
| tcgttcgagg cgatgccggc ggacgagctg gcgcgcgtcg agaagcgcat cttcagcaag | 3900 |
| tcactcgccg aggtgtgggc cgagaccaag gacttctaca tcacgcggct caacaacccg | 3960 |
| gagaagatcc gcaaggcgga gaacgaggac cccaagctca gatgtcact ctgcttccgc | 4020 |
| tggtacctcg ggctcagctc gttctgggcc aacaacggca tcgcggaccg cacgatggac | 4080 |
| taccagatct ggtgcggccc tgccatcggc gccttcaacg acttcatcgc cgactcgtac | 4140 |
| ctcgacgtgg ccgtctcggg cgagttcccc gacgtcgtgc agatcaacct gcagatcctg | 4200 |
| tcgggcgcag cctacctcca gcgcctcctc tccgtcaagc tcgcaccgcg gatcgacgtc | 4260 |
| gacaccgagg acgacctctt cacctaccgc cccgaccacg cactctaa | 4308 |

<210> SEQ ID NO 6
<211> LENGTH: 1435
<212> TYPE: PRT
<213> ORGANISM: Schizochytrium sp.

<400> SEQUENCE: 6

Met Thr Ser Ser Lys Lys Thr Pro Val Trp Glu Met Ser Lys Glu Glu
1               5                   10                  15

Leu Leu Asp Gly Lys Thr Val Val Phe Asp Tyr Asn Glu Leu Leu Glu
            20                  25                  30

Phe Ala Glu Gly Asp Val Gly Gln Val Phe Gly Pro Glu Phe Asp Ile
        35                  40                  45

Ile Asp Lys Tyr Arg Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

Gly Val Ala His Glu Gly Glu Thr Leu Val Tyr Asp Ile Arg Val Thr
145                 150                 155                 160

Gly Phe Ala Lys Gly Ala Gly Gly Glu Ile Ser Met Phe Phe Phe Glu
                165                 170                 175

Tyr Asp Cys Phe Val Asp Gly Arg Leu Leu Ile Glu Met Arg Asp Gly
            180                 185                 190

Cys Ala Gly Phe Phe Thr Asp Ala Glu Leu Ala Ala Gly Lys Gly Val
        195                 200                 205

Leu Lys Thr Lys Ala Glu Leu Ala Ala Arg Ala Gln Ile Gln Lys Gln
    210                 215                 220

Asp Ile Ala Pro Phe Ala Pro Ala Pro Cys Ser His Lys Thr Ser Leu
225                 230                 235                 240

```
Asp Ala Arg Glu Met Arg Leu Leu Val Asp Arg Gln Trp Ala Arg Val
                245                 250                 255
Phe Gly Ser Gly Met Ala Gly Ile Asp Tyr Lys Leu Cys Ala Arg Lys
            260                 265                 270
Met Leu Met Ile Asp Arg Val Thr His Leu Asp Pro Arg Gly Gly Ala
        275                 280                 285
His Gly Leu Gly Leu Leu Ile Gly Glu Lys Val Leu Glu Arg Asp His
    290                 295                 300
Trp Tyr Phe Pro Cys His Phe Val Arg Asp Glu Val Met Ala Gly Ser
305                 310                 315                 320
Leu Val Ser Asp Gly Cys Ser Gln Leu Leu Lys Val Tyr Met Leu Trp
                325                 330                 335
Leu Gly Leu His Thr Val Gly Ala Phe Asp Phe Arg Pro Val Ser
            340                 345                 350
Gly His Ala Asn Lys Val Arg Cys Arg Gly Gln Ile Ser Pro His Lys
        355                 360                 365
Gly Lys Leu Val Tyr Val Met Glu Ile Lys Glu Met Gly Phe Asp Ala
    370                 375                 380
Lys Thr Gly Asp Pro Phe Ala Ile Ala Asp Val Asp Ile Ile Asp Val
385                 390                 395                 400
Asn Phe Glu Glu Gly Gln Ala Phe Ala Gly Val Glu Asp Leu His Ser
                405                 410                 415
Tyr Gly Gln Gly Asp Leu Arg Lys Lys Ile Val Val Asp Phe Lys Gly
            420                 425                 430
Ile Ala Leu Ser Leu Gln Lys Arg Lys Glu Gln Gln Lys Glu Ser Met
        435                 440                 445
Thr Val Thr Thr Thr Thr Thr Thr Ser Arg Val Ile Ala Pro Pro
    450                 455                 460
Ser Gly Cys Leu Lys Gly Asp Pro Thr Ala Pro Thr Ser Val Thr Trp
465                 470                 475                 480
His Pro Met Ala Glu Gly Asn Gly Gly Pro Gly Pro Thr Pro Ser Phe
                485                 490                 495
Ser Pro Ser Ala Tyr Pro Pro Arg Ala Val Cys Phe Ser Pro Phe Pro
            500                 505                 510
Asn Asn Pro Leu Asp Asn Asp His Thr Pro Gly Gln Met Pro Leu Thr
        515                 520                 525
Trp Phe Asn Met Ser Glu Phe Met Cys Gly Lys Val Ser Asn Cys Leu
    530                 535                 540
Gly Pro Glu Phe Ala Arg Phe Asp Ala Ser Lys Thr Ser Arg Ser Pro
545                 550                 555                 560
Ala Phe Asp Leu Ala Leu Val Thr Arg Val Thr Ser Val Ala Asp Met
                565                 570                 575
Glu His Gly Pro Phe Tyr Asn Val Asp Val Asn Pro Gly Gln Gly Thr
            580                 585                 590
Met Val Gly Glu Phe Asp Cys Pro Ala Asp Ala Trp Phe Phe Gly Ala
        595                 600                 605
Ser Ser Arg Asp Asp His Met Pro Tyr Ser Ile Leu Met Glu Ile Ala
    610                 615                 620
Leu Gln Thr Ser Gly Val Leu Thr Ser Val Leu Lys Ala Pro Leu Thr
625                 630                 635                 640
Met Asp Lys Asp Asp Ile Leu Phe Arg Asn Leu Asp Ala Asp Ala Glu
                645                 650                 655
Leu Val Gly Asp Ala Met Pro Asp Val Arg Gly Lys Thr Ile Arg Asn
```

```
            660                 665                 670
Phe Thr Lys Cys Thr Gly Tyr Ser Met Leu Gly Lys Met Gly Ile His
        675                 680                 685
Arg Phe Thr Phe Glu Leu Ser Val Asp Gly Ala Val Phe Tyr Lys Gly
        690                 695                 700
Ser Thr Ser Phe Gly Trp Phe Val Pro Glu Val Phe Glu Ser Gln Thr
705                 710                 715                 720
Gly Leu Asp Asn Gly Lys Pro Arg Leu Pro Trp Tyr Arg Glu Asn Asn
                725                 730                 735
Val Ala Val Asp Thr Leu Ser Ala Pro Ala Ser Ser Ala Gln
                740                 745                 750
Gly Gln Leu Gln Leu Gln Arg Arg Gly Ser Gln Ala Gln Phe Leu Asp
        755                 760                 765
Thr Ile His Leu Ala Gly Ser Gly Ala Gly Val His Gly Gln Gly Tyr
        770                 775                 780
Ala His Gly Glu Lys Ala Val Asn Lys Gln Asp Trp Phe Phe Ser Cys
785                 790                 795                 800
His Phe Trp Phe Asp Pro Val Met Pro Gly Ser Leu Gly Ile Glu Ser
                805                 810                 815
Met Phe Gln Leu Val Glu Ala Trp Cys Val Lys Gln Gly Leu Ala Ala
                820                 825                 830
Arg His Gly Ile Ala His Pro Val Phe Ala His Ala Pro Gly Ala Thr
        835                 840                 845
Ser Trp Lys Tyr Arg Gly Gln Leu Thr Pro Lys Asn Asp Arg Met Asp
        850                 855                 860
Ser Glu Val His Ile Lys Ser Val Ala Ala Phe Ser Ser Trp Val Asp
865                 870                 875                 880
Val Val Ala Asp Gly Phe Leu Phe Val Asp Gly Leu Arg Val Tyr Ser
                885                 890                 895
Ala Asp Asn Leu Arg Val Arg Ile Gln Thr Gly Ala Gly His Val Glu
                900                 905                 910
Glu Gln Glu Val Ala Ala Lys Ala Thr Thr Lys Asn Ser Ser Ile Ala
        915                 920                 925
Asp Val Asp Val Ala Asp Leu Gln Ala Leu Lys Gln Ala Leu Leu Thr
        930                 935                 940
Leu Glu Arg Pro Leu Gln Leu Asp Ala Gly Ser Glu Val Pro Ala Cys
945                 950                 955                 960
Ala Val Ser Asp Leu Gly Asp Arg Gly Phe Met Glu Thr Tyr Gly Val
                965                 970                 975
Val Ala Pro Leu Tyr Ser Gly Ala Met Ala Lys Gly Ile Ala Ser Ala
                980                 985                 990
Asp Leu Val Ile Ala Met Gly Gln Arg Lys Met Leu Gly Ser Phe Gly
        995                 1000                1005
Ala Gly Gly Leu Pro Met His Val Val Arg Ala Gly Ile Glu Lys
        1010                1015                1020
Ile Gln Ala Ala Leu Pro Ala Gly Pro Tyr Ala Val Asn Leu Ile
        1025                1030                1035
His Ser Pro Phe Asp Ala Asn Leu Glu Lys Gly Asn Val Asp Leu
        1040                1045                1050
Phe Leu Glu Lys Gly Val Arg Val Val Glu Ala Ser Ala Phe Met
        1055                1060                1065
Glu Leu Thr Pro Gln Val Val Arg Tyr Arg Ala Thr Gly Leu Ser
        1070                1075                1080
```

Arg Asp Ala Arg Gly Gly Ser Val Arg Thr Ala His Lys Ile Ile
1085                1090                1095

Gly Lys Val Ser Arg Thr Glu Leu Ala Glu Met Phe Ile Arg Pro
1100                1105                1110

Ala Pro Gln Ala Ile Leu Asp Lys Leu Val Ala Ser Gly Glu Ile
1115                1120                1125

Thr Pro Glu Gln Ala Ala Leu Ala Leu Glu Val Pro Met Ala Asp
1130                1135                1140

Asp Ile Ala Val Glu Ala Asp Ser Gly Gly His Thr Asp Asn Arg
1145                1150                1155

Pro Ile His Val Ile Leu Pro Leu Ile Leu Ser Leu Arg Asn Arg
1160                1165                1170

Leu Gln Arg Glu Leu Lys Tyr Pro Ala Arg His Arg Val Arg Val
1175                1180                1185

Gly Ala Gly Gly Gly Ile Gly Cys Pro Gln Ala Ala Leu Gly Ala
1190                1195                1200

Phe His Met Gly Ala Ala Phe Val Val Thr Gly Thr Val Asn Gln
1205                1210                1215

Leu Ser Arg Gln Ala Gly Thr Cys Asp Asn Val Arg Arg Gln Leu
1220                1225                1230

Ser Arg Ala Thr Tyr Ser Asp Ile Thr Met Ala Pro Ala Ala Asp
1235                1240                1245

Met Phe Glu Gln Gly Val Glu Leu Gln Val Leu Lys Lys Gly Thr
1250                1255                1260

Met Phe Pro Ser Arg Ala Lys Lys Leu Phe Glu Leu Phe His Lys
1265                1270                1275

Tyr Asp Ser Phe Glu Ala Met Pro Ala Asp Glu Leu Ala Arg Val
1280                1285                1290

Glu Lys Arg Ile Phe Ser Lys Ser Leu Ala Glu Val Trp Ala Glu
1295                1300                1305

Thr Lys Asp Phe Tyr Ile Thr Arg Leu Asn Asn Pro Glu Lys Ile
1310                1315                1320

Arg Lys Ala Glu Asn Glu Asp Pro Lys Leu Lys Met Ser Leu Cys
1325                1330                1335

Phe Arg Trp Tyr Leu Gly Leu Ser Ser Phe Trp Ala Asn Asn Gly
1340                1345                1350

Ile Ala Asp Arg Thr Met Asp Tyr Gln Ile Trp Cys Gly Pro Ala
1355                1360                1365

Ile Gly Ala Phe Asn Asp Phe Ile Ala Asp Ser Tyr Leu Asp Val
1370                1375                1380

Ala Val Ser Gly Glu Phe Pro Asp Val Val Gln Ile Asn Leu Gln
1385                1390                1395

Ile Leu Ser Gly Ala Ala Tyr Leu Gln Arg Leu Leu Ser Val Lys
1400                1405                1410

Leu Ala Pro Arg Ile Asp Val Asp Thr Glu Asp Asp Leu Phe Thr
1415                1420                1425

Tyr Arg Pro Asp His Ala Leu
1430                1435

<210> SEQ ID NO 7
<211> LENGTH: 1395
<212> TYPE: DNA
<213> ORGANISM: Schizochytrium sp.

<400> SEQUENCE: 7

```
actcgcatcg cgatcgtggg gatgtcggcg atcctgccga gcggggagaa cgtgcgcgag    60
agctgggagg cgatccgcga tgggctggat tgcctgagcg atctgccggc ggaccgcgtg   120
gacgtgacgg cctactacaa cccggagaag acgaccaagg acaagatcta ctgcaagcgc   180
ggcgggttca tcccggagta cgacttcgac gcgcgtgagt tcgggctcaa catgttccag   240
atggaggact cggacgccaa ccagacgatc tcgctgctca aggtgaagga ggcgctgacg   300
gacgccaaca tcccggcgtt ctcgagcggt aagaagaaca tcggctgcgt gctgggcatc   360
ggcggcggcc agaaggcgag ccacgagttc tactcgcggc tcaactacgt ggtcgtggac   420
aaggtgctgc gcaagatggg cctgccggag gaagacgtgg cggcggcggt ggacaagtac   480
aaggcgagtt tccccgagtg cgcctcgac tctttccccg ggttcctggg caacgtcacg   540
gcggggcgct gctgcaatac cttcaacatg gagggcatga actgcgtcgt ggacgcggcc   600
tgcgcgtcgt cgctgatcgc ggtcaaagtg gcgatcgagg agctgctcta cggcgactgc   660
gatgcgatga tcgcgggtgc cacctgcacg gacaactcga tcgggatgta catggccttc   720
tccaagacgc ccgtgttttc cacggacccg agcgtcaagg cgtacgacgc cgccaccaaa   780
ggcatgctca tcggcgaggg ctcggcgatg ctcgtgctga agcgctacgc ggacgccgtg   840
cgcgacggcg acaccgtgca cgccgtcatc aaggggtgcg cgtcctcgag cgacggcaag   900
gcggcgggca tctacacgcc gacaatctcg gccaggagg aggccctgcg ccgcgcctac   960
gcccgcgcca atgtcgaccc ggccactgtg acgctggtgg agggccacgg cacgggtacg  1020
ccggtgggcg acaagatcga gctgacggcg ctgagcaacc tcttctccaa ggcgttttct  1080
gccaacggtg gcggcgcgga ggaagcagag caggtggcgg tgggcagcat caagtcgcag  1140
atcgggcacc tcaaggcggt ggccgggctg gccgggctgg tcaaggtggt gctggcgctc  1200
aagcacaaga cgctgccgca gacgatcaac gtcgacaagc cgccgtcgct ggtggacggg  1260
accccgatcc agcagtcgcc gctgtacgtc aacacgatga accgcccctg gttcacgccc  1320
gtaggggtgc cgcgccgcgc cggcgtgtcg tcgtttgggt ttggcggtgc caactaccac  1380
gccgtgctgg aggag                                                   1395
```

<210> SEQ ID NO 8
<211> LENGTH: 465
<212> TYPE: PRT
<213> ORGANISM: Schizochytrium sp.

<400> SEQUENCE: 8

```
Thr Arg Ile Ala Ile Val Gly Met Ser Ala Ile Leu Pro Ser Gly Glu
1               5                   10                  15

Asn Val Arg Glu Ser Trp Glu Ala Ile Arg Asp Gly Leu Asp Cys Leu
                20                  25                  30

Ser Asp Leu Pro Ala Asp Arg Val Asp Val Thr Ala Tyr Tyr Asn Pro
            35                  40                  45

Glu Lys Thr Thr Lys Asp Lys Ile Tyr Cys Lys Arg Gly Gly Phe Ile
        50                  55                  60

Pro Glu Tyr Asp Phe Asp Ala Arg Glu Phe Gly Leu Asn Met Phe Gln
65                  70                  75                  80

Met Glu Asp Ser Asp Ala Asn Gln Thr Ile Ser Leu Leu Lys Val Lys
                85                  90                  95

Glu Ala Leu Thr Asp Ala Asn Ile Pro Ala Phe Ser Ser Gly Lys Lys
            100                 105                 110
```

```
Asn Ile Gly Cys Val Leu Gly Ile Gly Gly Gln Lys Ala Ser His
            115                 120                 125
Glu Phe Tyr Ser Arg Leu Asn Tyr Val Val Asp Lys Val Leu Arg
130                 135                 140
Lys Met Gly Leu Pro Glu Asp Val Ala Ala Val Asp Lys Tyr
145                 150                 155                 160
Lys Ala Ser Phe Pro Glu Trp Arg Leu Asp Ser Phe Pro Gly Phe Leu
                165                 170                 175
Gly Asn Val Thr Ala Gly Arg Cys Cys Asn Thr Phe Asn Met Glu Gly
                180                 185                 190
Met Asn Cys Val Val Asp Ala Ala Cys Ala Ser Ser Leu Ile Ala Val
            195                 200                 205
Lys Val Ala Ile Glu Glu Leu Leu Tyr Gly Asp Cys Asp Ala Met Ile
210                 215                 220
Ala Gly Ala Thr Cys Thr Asp Asn Ser Ile Gly Met Tyr Met Ala Phe
225                 230                 235                 240
Ser Lys Thr Pro Val Phe Ser Thr Asp Pro Ser Val Lys Ala Tyr Asp
                245                 250                 255
Ala Ala Thr Lys Gly Met Leu Ile Gly Glu Gly Ser Ala Met Leu Val
            260                 265                 270
Leu Lys Arg Tyr Ala Asp Ala Val Arg Asp Gly Asp Thr Val His Ala
275                 280                 285
Val Ile Lys Gly Cys Ala Ser Ser Asp Gly Lys Ala Ala Gly Ile
290                 295                 300
Tyr Thr Pro Thr Ile Ser Gly Gln Glu Ala Leu Arg Arg Ala Tyr
305                 310                 315                 320
Ala Arg Ala Asn Val Asp Pro Ala Thr Val Thr Leu Val Glu Gly His
                325                 330                 335
Gly Thr Gly Thr Pro Val Gly Asp Lys Ile Glu Leu Thr Ala Leu Ser
            340                 345                 350
Asn Leu Phe Ser Lys Ala Phe Ser Ala Asn Gly Gly Ala Glu Glu
355                 360                 365
Ala Glu Gln Val Ala Val Gly Ser Ile Lys Ser Gln Ile Gly His Leu
370                 375                 380
Lys Ala Val Ala Gly Leu Ala Gly Leu Val Lys Val Val Leu Ala Leu
385                 390                 395                 400
Lys His Lys Thr Leu Pro Gln Thr Ile Asn Val Asp Lys Pro Pro Ser
                405                 410                 415
Leu Val Asp Gly Thr Pro Ile Gln Gln Ser Pro Leu Tyr Val Asn Thr
            420                 425                 430
Met Asn Arg Pro Trp Phe Thr Pro Val Gly Val Pro Arg Arg Ala Gly
435                 440                 445
Val Ser Ser Phe Gly Phe Gly Gly Ala Asn Tyr His Ala Val Leu Glu
    450                 455                 460
Glu
465

<210> SEQ ID NO 9
<211> LENGTH: 903
<212> TYPE: DNA
<213> ORGANISM: Schizochytrium sp.

<400> SEQUENCE: 9
ttctcgggcc agggcgcgca gtacacgcac atgttcagcg acgtggcgat gaactggccc      60
```

-continued

| | |
|---|---|
| ccgttccgcg agagcgtcgc cgccatggac cgcgcccagc gcgagcgctt cgggcggcct | 120 |
| gccaagcgcg tgagcagcgt gctgtacccg cgcaagccgt acggcgacga accgcggcag | 180 |
| gaccacaagg agatctcgca aacgcgctac tcgcagcccg caacgctcgc gtgctcggtc | 240 |
| ggcgcctttg acatcttcaa agcggcggga ctggcgccga gctttgcggc gggccactcg | 300 |
| ctgggcgagt ttgcggcgct ctacgcggcc gggtcgctcg atcgcgacgc cgtcttcgac | 360 |
| ctggtctgcg cgcgcgccaa ggccatgagc gacttcacgg cccaggccag cagcagcggt | 420 |
| ggcgccatgg cggccgtgat tggcgccaag gcggaccagc tctcgctggg tggcgcgccc | 480 |
| gacgtgtggc tcgccaacag caactcgccc tcgcagaccg tgatcacggg aaccgccgaa | 540 |
| gcagtggctg cggcctctga caagttgcgc tgcagcggca acttccgcgt cgtgcctctg | 600 |
| gcctgcgagg cggccttcca ctcgccgcac atgcgcggcg cggagcagac gtttgcgtcg | 660 |
| gcgctcgcgc aggcgcccgt gtcggcaccg gcggctgctc ggttctactc taacgtgacg | 720 |
| gggggcgccg cggtaacctc gcccgcggac gtcaaaacga acctgggcaa gcacatgacg | 780 |
| agccctgtgc agttcgtgca gcaggtgcga gccatgcacg cggcgggcgc gcgtgtgttt | 840 |
| gtggagtttg gcccaagca ggtcctgtcg cgcctcgtca aggagaccct tggcgaggcc | 900 |
| ggc | 903 |

<210> SEQ ID NO 10
<211> LENGTH: 301
<212> TYPE: PRT
<213> ORGANISM: Schizochytrium sp.

<400> SEQUENCE: 10

Phe Ser Gly Gln Gly Ala Gln Tyr Thr His Met Phe Ser Asp Val Ala
1               5                   10                  15

Met Asn Trp Pro Pro Phe Arg Glu Ser Val Ala Met Asp Arg Ala
            20                  25                  30

Gln Arg Glu Arg Phe Gly Arg Pro Ala Lys Arg Val Ser Ser Val Leu
        35                  40                  45

Tyr Pro Arg Lys Pro Tyr Gly Asp Glu Pro Arg Gln Asp His Lys Glu
    50                  55                  60

Ile Ser Gln Thr Arg Tyr Ser Gln Pro Ala Thr Leu Ala Cys Ser Val
65                  70                  75                  80

Gly Ala Phe Asp Ile Phe Lys Ala Ala Gly Leu Ala Pro Ser Phe Ala
                85                  90                  95

Ala Gly His Ser Leu Gly Glu Phe Ala Ala Leu Tyr Ala Ala Gly Ser
            100                 105                 110

Leu Asp Arg Asp Ala Val Phe Asp Leu Val Cys Ala Arg Ala Lys Ala
        115                 120                 125

Met Ser Asp Phe Thr Ala Gln Ala Ser Ser Ser Gly Gly Ala Met Ala
    130                 135                 140

Ala Val Ile Gly Ala Lys Ala Asp Gln Leu Ser Leu Gly Gly Ala Pro
145                 150                 155                 160

Asp Val Trp Leu Ala Asn Ser Asn Ser Pro Ser Gln Thr Val Ile Thr
                165                 170                 175

Gly Thr Ala Glu Ala Val Ala Ala Ser Asp Lys Leu Arg Cys Ser
            180                 185                 190

Gly Asn Phe Arg Val Val Pro Leu Ala Cys Glu Ala Ala Phe His Ser
        195                 200                 205

Pro His Met Arg Gly Ala Glu Gln Thr Phe Ala Ser Ala Leu Ala Gln
    210                 215                 220

| | | | | | | | | | | |
|---|---|---|---|---|---|---|---|---|---|---|
|Ala|Pro|Val|Ser|Ala|Pro|Ala|Ala|Arg|Phe|Tyr|Ser|Asn|Val|Thr|
|225| | | | |230| | | | |235| | | | |240|

Gly Gly Ala Ala Val Thr Ser Pro Ala Asp Val Lys Thr Asn Leu Gly
          245                 250                 255

Lys His Met Thr Ser Pro Val Gln Phe Val Gln Gln Val Arg Ala Met
              260                 265                 270

His Ala Ala Gly Ala Arg Val Phe Val Glu Phe Gly Pro Lys Gln Val
          275                 280                 285

Leu Ser Arg Leu Val Lys Glu Thr Leu Gly Glu Ala Gly
          290                 295                 300

<210> SEQ ID NO 11
<211> LENGTH: 2103
<212> TYPE: DNA
<213> ORGANISM: Schizochytrium sp.

<400> SEQUENCE: 11

```
tccggcaaca gcaagagcac tcgtggcagt gctgatctgc aagcgctgct ggccaaggcg      60
gagactgtgg tgatggctgt gctggctgcc aagactggct acgaggccga catggttgag     120
gcggacatgg acctggaggc cgagctcggc atcgactcga tcaagcgcgt ggagatcctt     180
tccgaggtgc agggccagct gggcgtcgag gccaaggacg tggatgcgct gagccgcacg     240
cgcacggtcg gtgaggttgt ggacgccatg aaggcggaga tcgtggctgc ctctggtggt     300
agtgctcctg cggttccttc ggcgcccgct gcttctgcag ctccgactcc cgctgcttcg     360
actgcgcctt ctgctgatct gcaagcgctg ctgtccaagg cggagactgt ggtgatggct     420
gtgctggcgg ccaagactgg ctacgaggcc gacatggtcg aggcggacat ggacctggag     480
gccgagctcg gcatcgactc gatcaagcgc gtggagatcc tctcggaggt gcagggccag     540
ctgggcgtcg aggccaagga cgtggatgcg ctgagccgca cgcgcacggt cggtgaggtt     600
gtggatgcca tgaaggcgga aatcgtggct gcctctgctg gtagtgctcc tgctcctgct     660
gttccttcgg cgcccgctgc ttctgcagct ccgactcccg ctgcttcgac tgcgccttct     720
gctgatctgc aagcgctgct gtccaaggcg gagacggtgg tgatggctgt gctggcggcc     780
aagactggct acgaggccga catggtcgag gcggacatgg acctggaggc cgagctcggc     840
atcgactcga tcaagcgcgt ggagatcctc tcggaggtgc agggccagct gggcgtcgag     900
gccaaggacg tggatgcgct gagccgcacg cgcacggtcg gtgaggttgt ggatgccatg     960
aaggcggaaa tcgtggctgc ctctggtggt agtgctcctg ctcctgcggt tccttcggcg    1020
cccgctgctt ctgcagctcc gactcccgcg ctgcgacag cgccttctgc tgatctgcaa    1080
gcgctgctgg ccaaggcgga gactgtggtg atggctgtgc tggcggccaa gactggctac    1140
gaggccgaca tggtcgaggc ggacatggac ctggaggccg agctcggcat cgactcgatc    1200
aagcgcgtgg agatccttt cgaggtgcag ggccagctgg cgtcgaggc caaggacgta    1260
gatgcgctga gccgcacgcg cacggtcggt gaggttgtg atgccatgaa ggcggagatc    1320
gtggctgcct ctgctggtag tgctcctgct cctgctgttc cttcggcgcc cgctgcttct    1380
gcagctccga ctcccgctgc ttcgactgcg ccttctgctg atctgcaagc gctgctgtcc    1440
aaggcggaga ctgtggtgat ggctgtgctg gcggccaaga ctggctacga ggccgacatg    1500
gtcgaggcgg acatggacct ggaggccgag ctcggcatcg actcgatcaa gcgcgtggag    1560
atcctctcgg aggtgcaggg ccagctgggc gtcgaggcca aggacgtgga tgcgctgagc    1620
cgcacgcgca cggtcggtga ggttgtggat gccatgaagg cggaaatcgt ggctgcctct    1680
```

-continued

```
ggtggtagtg ctcctgctgc tgctgttcct tcggcgcccg ctgcttctgc agctccgact    1740
cctgcgactg cgccttctgc tgatctgcaa gcgctgctgt ccaaggcgga gactgtggtg    1800
atggctgtgc tggcggccaa gactggctac gaggccgaca tggtcgaggc ggacatggac    1860
ctggaggccg agctcggcat cgactcgatc aagcgcgtgg agatcctttc cgaggtgcag    1920
ggccagctgg gcgtcgaggc caaggacgta gatgcgctga ccgcacgcg cacggtcggt     1980 gaagtggtgg acgccatgaa ggcggagatc gtggctgcct ctggtggtag tgctcctgct    2040
gctccttcgg cgcccgcgct tcttccaacg ctgtttggtt ccgagtgcga ggacctgtct    2100
ctg                                                                  2103
```

<210> SEQ ID NO 12
<211> LENGTH: 701
<212> TYPE: PRT
<213> ORGANISM: Schizochytrium sp.

<400> SEQUENCE: 12

```
Ser Gly Asn Ser Lys Ser Thr Arg Gly Ser Ala Asp Leu Gln Ala Leu
1               5                   10                  15

Leu Ala Lys Ala Glu Thr Val Val Met Ala Val Leu Ala Ala Lys Thr
            20                  25                  30

Gly Tyr Glu Ala Asp Met Val Glu Ala Asp Met Asp Leu Glu Ala Glu
        35                  40                  45

Leu Gly Ile Asp Ser Ile Lys Arg Val Glu Ile Leu Ser Glu Val Gln
    50                  55                  60

Gly Gln Leu Gly Val Glu Ala Lys Asp Val Asp Ala Leu Ser Arg Thr
65                  70                  75                  80

Arg Thr Val Gly Glu Val Val Asp Ala Met Lys Ala Glu Ile Val Ala
                85                  90                  95

Ala Ser Gly Gly Ser Ala Pro Ala Val Pro Ser Ala Pro Ala Ala Ser
            100                 105                 110

Ala Ala Pro Thr Pro Ala Ala Ser Thr Ala Pro Ser Ala Asp Leu Gln
        115                 120                 125

Ala Leu Leu Ser Lys Ala Glu Thr Val Val Met Ala Val Leu Ala Ala
    130                 135                 140

Lys Thr Gly Tyr Glu Ala Asp Met Val Glu Ala Asp Met Asp Leu Glu
145                 150                 155                 160

Ala Glu Leu Gly Ile Asp Ser Ile Lys Arg Val Glu Ile Leu Ser Glu
                165                 170                 175

Val Gln Gly Gln Leu Gly Val Glu Ala Lys Asp Val Asp Ala Leu Ser
            180                 185                 190

Arg Thr Arg Thr Val Gly Glu Val Val Asp Ala Met Lys Ala Glu Ile
        195                 200                 205

Val Ala Ala Ser Ala Gly Ser Ala Pro Ala Pro Ala Val Pro Ser Ala
    210                 215                 220

Pro Ala Ala Ser Ala Ala Pro Thr Pro Ala Ala Ser Thr Ala Pro Ser
225                 230                 235                 240

Ala Asp Leu Gln Ala Leu Leu Ser Lys Ala Glu Thr Val Val Met Ala
                245                 250                 255

Val Leu Ala Ala Lys Thr Gly Tyr Glu Ala Asp Met Val Glu Ala Asp
            260                 265                 270

Met Asp Leu Glu Ala Glu Leu Gly Ile Asp Ser Ile Lys Arg Val Glu
        275                 280                 285
```

```
Ile Leu Ser Glu Val Gln Gly Gln Leu Gly Val Glu Ala Lys Asp Val
    290                 295                 300

Asp Ala Leu Ser Arg Thr Arg Thr Val Gly Glu Val Val Asp Ala Met
305                 310                 315                 320

Lys Ala Glu Ile Val Ala Ala Ser Gly Gly Ser Ala Pro Ala Pro Ala
                325                 330                 335

Val Pro Ser Ala Pro Ala Ala Ser Ala Ala Pro Thr Pro Ala Ala Ala
                340                 345                 350

Thr Ala Pro Ser Ala Asp Leu Gln Ala Leu Leu Ala Lys Ala Glu Thr
                355                 360                 365

Val Val Met Ala Val Leu Ala Ala Lys Thr Gly Tyr Glu Ala Asp Met
370                 375                 380

Val Glu Ala Asp Met Asp Leu Glu Ala Glu Leu Gly Ile Asp Ser Ile
385                 390                 395                 400

Lys Arg Val Glu Ile Leu Ser Glu Val Gln Gly Gln Leu Gly Val Glu
                405                 410                 415

Ala Lys Asp Val Asp Ala Leu Ser Arg Thr Arg Thr Val Gly Glu Val
                420                 425                 430

Val Asp Ala Met Lys Ala Glu Ile Val Ala Ala Ser Ala Gly Ser Ala
                435                 440                 445

Pro Ala Pro Ala Val Pro Ser Ala Pro Ala Ala Ser Ala Ala Pro Thr
                450                 455                 460

Pro Ala Ala Ser Thr Ala Pro Ser Ala Asp Leu Gln Ala Leu Leu Ser
465                 470                 475                 480

Lys Ala Glu Thr Val Val Met Ala Val Leu Ala Ala Lys Thr Gly Tyr
                485                 490                 495

Glu Ala Asp Met Val Glu Ala Asp Met Asp Leu Glu Ala Glu Leu Gly
                500                 505                 510

Ile Asp Ser Ile Lys Arg Val Glu Ile Leu Ser Glu Val Gln Gly Gln
                515                 520                 525

Leu Gly Val Glu Ala Lys Asp Val Asp Ala Leu Ser Arg Thr Arg Thr
530                 535                 540

Val Gly Glu Val Val Asp Ala Met Lys Ala Glu Ile Val Ala Ala Ser
545                 550                 555                 560

Gly Gly Ser Ala Pro Ala Ala Val Pro Ser Ala Pro Ala Ala Ser
                565                 570                 575

Ala Ala Pro Thr Pro Ala Thr Ala Pro Ser Ala Asp Leu Gln Ala Leu
                580                 585                 590

Leu Ser Lys Ala Glu Thr Val Val Met Ala Val Leu Ala Ala Lys Thr
595                 600                 605

Gly Tyr Glu Ala Asp Met Val Glu Ala Asp Met Asp Leu Glu Ala Glu
610                 615                 620

Leu Gly Ile Asp Ser Ile Lys Arg Val Glu Ile Leu Ser Glu Val Gln
625                 630                 635                 640

Gly Gln Leu Gly Val Glu Ala Lys Asp Val Asp Ala Leu Ser Arg Thr
                645                 650                 655

Arg Thr Val Gly Glu Val Val Asp Ala Met Lys Ala Glu Ile Val Ala
                660                 665                 670

Ala Ser Gly Gly Ser Ala Pro Ala Ala Pro Ser Ala Pro Ala Leu Leu
                675                 680                 685

Pro Thr Leu Phe Gly Ser Glu Cys Glu Asp Leu Ser Leu
690                 695                 700
```

-continued

```
<210> SEQ ID NO 13
<211> LENGTH: 276
<212> TYPE: DNA
<213> ORGANISM: Schizochytrium sp.

<400> SEQUENCE: 13
agtgctgatc tgcaagcgct gctggccaag gcggagactg tggtgatggc tgtgctggct      60
gccaagactg gctacgaggc cgacatggtt gaggcggaca tggacctgga ggccgagctc     120
ggcatcgact cgatcaagcg cgtggagatc ctttccgagg tgcagggcca gctgggcgtc     180
gaggccaagg acgtggatgc gctgagccgc acgcgcacgg tcggtgaggt tgtggacgcc     240
atgaaggcgg agatcgtggc tgcctctggt ggtagt                                276

<210> SEQ ID NO 14
<211> LENGTH: 92
<212> TYPE: PRT
<213> ORGANISM: Schizochytrium sp.

<400> SEQUENCE: 14

Ser Ala Asp Leu Gln Ala Leu Leu Ala Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Val Val Asp Ala
65                  70                  75                  80

Met Lys Ala Glu Ile Val Ala Ala Ser Gly Gly Ser
                85                  90

<210> SEQ ID NO 15
<211> LENGTH: 276
<212> TYPE: DNA
<213> ORGANISM: Schizochytrium sp.

<400> SEQUENCE: 15
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctgct ggtagt                                276

<210> SEQ ID NO 16
<211> LENGTH: 92
<212> TYPE: PRT
<213> ORGANISM: Schizochytrium sp.

<400> SEQUENCE: 16

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60
```

Val Asp Ala Leu Ser Arg Thr Arg Thr Val Gly Glu Val Val Asp Ala
65                  70                  75                  80

Met Lys Ala Glu Ile Val Ala Ala Ser Ala Gly Ser
                85                  90

<210> SEQ ID NO 17
<211> LENGTH: 276
<212> TYPE: DNA
<213> ORGANISM: Schizochytrium sp.

<400> SEQUENCE: 17
tctgctgatc tgcaagcgct gctgtccaag gcggagacgg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctggt ggtagt                               276

<210> SEQ ID NO 18
<211> LENGTH: 92
<212> TYPE: PRT
<213> ORGANISM: Schizochytrium sp.

<400> SEQUENCE: 18

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
                20                  25                  30

Asp Met Asp Leu Glu Ala Glu Leu Gly Ile Asp Ser Ile Lys Arg Val
            35                  40                  45

Glu Ile Leu Ser Glu Val Gln Gly Gln Leu Gly Val Glu Ala Lys Asp
        50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Gly Gly Ser
                85                  90

<210> SEQ ID NO 19
<211> LENGTH: 276
<212> TYPE: DNA
<213> ORGANISM: Schizochytrium sp.

<400> SEQUENCE: 19
tctgctgatc tgcaagcgct gctggccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctttccgagg tgcagggcca gctgggcgtc     180
gaggccaagg acgtagatgc gctgagccgc acgcgcacgg tcggtgaggt tgtggatgcc     240
atgaaggcgg agatcgtggc tgcctctgct ggtagt                               276

<210> SEQ ID NO 20
<211> LENGTH: 92
<212> TYPE: PRT
<213> ORGANISM: Schizochytrium sp.

<400> SEQUENCE: 20

Ser Ala Asp Leu Gln Ala Leu Leu Ala Lys Ala Glu Thr Val Val Met

```
                1               5                  10                  15
Ala Val Leu Ala Ala Lys Thr Gly Tyr Glu Ala Asp Met Val Glu Ala
                20                  25                  30

Asp Met Asp Leu Glu Ala Glu Leu Gly Ile Asp Ser Ile Lys Arg Val
                35                  40                  45

Glu Ile Leu Ser Glu Val Gln Gly Gln Leu Gly Val Glu Ala Lys Asp
                50                  55                  60

Val Asp Ala Leu Ser Arg Thr Arg Thr Val Gly Val Val Asp Ala
65                  70                  75                  80

Met Lys Ala Glu Ile Val Ala Ala Ser Ala Gly Ser
                85                  90

<210> SEQ ID NO 21
<211> LENGTH: 276
<212> TYPE: DNA
<213> ORGANISM: Schizochytrium sp.

<400> SEQUENCE: 21
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctggt ggtagt                                276

<210> SEQ ID NO 22
<211> LENGTH: 92
<212> TYPE: PRT
<213> ORGANISM: Schizochytrium sp.

<400> SEQUENCE: 22

Ser Ala Asp Leu Gln Ala Leu Leu Ser Lys Ala Glu Thr Val Val Met
1               5                  10                  15

Ala Val Leu Ala Ala Lys Thr Gly Tyr Glu Ala Asp Met Val Glu Ala
                20                  25                  30

Asp Met Asp Leu Glu Ala Glu Leu Gly Ile Asp Ser Ile Lys Arg Val
                35                  40                  45

Glu Ile Leu Ser Glu Val Gln Gly Gln Leu Gly Val Glu Ala Lys Asp
                50                  55                  60

Val Asp Ala Leu Ser Arg Thr Arg Thr Val Gly Val Val Asp Ala
65                  70                  75                  80

Met Lys Ala Glu Ile Val Ala Ala Ser Gly Gly Ser
                85                  90

<210> SEQ ID NO 23
<211> LENGTH: 276
<212> TYPE: DNA
<213> ORGANISM: Schizochytrium sp.

<400> SEQUENCE: 23
tctgctgatc tgcaagcgct gctgtccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctttccgagg tgcagggcca gctgggcgtc     180
gaggccaagg acgtagatgc gctgagccgc acgcgcacgg tcggtgaagt ggtggacgcc     240
atgaaggcgg agatcgtggc tgcctctggt ggtagt                                276
```

<210> SEQ ID NO 24
<211> LENGTH: 92
<212> TYPE: PRT
<213> ORGANISM: Schizochytrium sp.

<400> SEQUENCE: 24

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Glu Val Asp Ala
65                  70                  75                  80

Met Lys Ala Glu Ile Val Ala Ala Ser Gly Gly Ser
                85                  90

<210> SEQ ID NO 25
<211> LENGTH: 2178
<212> TYPE: DNA
<213> ORGANISM: Schizochytrium sp.

<400> SEQUENCE: 25

| | |
|---|---|
| gcgctacagg cggcgctcac gtccgtcgag gcgcagttcg gcaaggtggg tggctttgtg | 60 |
| ttccagttcg cgacgacga cgtgcaagcg cagctcggct gggcgctgct cgcggccaag | 120 |
| cacctcaaaa cttcgctgtc agaacagatc gagggcggtc gcaccttttt cgtggccgtc | 180 |
| gcgcggctcg acgccagct ggggctctcc ggcaagtcga cgaccgctac cgttgatctc | 240 |
| tcccgcgcgc agcagggcag cgtgttcggc ctgtgcaaga cactcgacct ggagtggccc | 300 |
| gctgtcttct gccgcggaat cgacctggcc gccgacctcg acgccgcaca ggccgcgcgg | 360 |
| tgcctgctgg gcgagctgtc agaccccgac gtggccgtgc gcgagtctgg ttactccgcc | 420 |
| tcgggccagc gctgcacgac aactacgaag tcgctgacta cgggcaagcc gcaccagccg | 480 |
| atctcctcgt cggacctctt tctggtgtcg ggcggcgcgc gcggcatcac ccgctgtgc | 540 |
| gtgcgcgagc tggcgcagcg cgtgggcggc ggcacgtacg tgctcatcgg ccgctcggag | 600 |
| ctgcccacga cggagcctgc ctgggcggtc ggcgtggagt ctggcaagcc gctggagaag | 660 |
| gccgcgctgg cgttcctgaa ggcggagttt gcagcgggcc gcggggccaa gccgacgccg | 720 |
| atgctgcaca agaagctcgt gggcgccgtg gtcggagcgc gcgaggtgcg agcctcgctc | 780 |
| gccgagatca ctgcacaggg cgccacggct gtgtacgagt cgtgcgacgt gagctctgcc | 840 |
| gccaaggtgc gtgagatggt agagcgcgtg cagcagcagg gcgggcggcg cgtgtcgggc | 900 |
| gtgttccacg cgtcgggcgt gctgcgcgac aagctcgtgg agaacaagtc gctggcggac | 960 |
| ttcagcgccg tgtacgacac caaggtgggc ggcctcatca acctgctggc ctgcgtggac | 1020 |
| ctggcgcagc tgcgtcacct cgtgctcttc agctcgctcg cgggcttcca cggcaacgtc | 1080 |
| gggcagtcgg actacgcaat ggccaacgag gcgctcaaca agctggcggc cacctgtcg | 1140 |
| gcggtgcacc cgcagctgtg cgcgcgctcg atctgcttcg accgtgggga cggcggcatg | 1200 |
| gtgacccccg cgctcaaggc caacttcatc cgcatgggca tccagatcat cccgcgccaa | 1260 |
| ggcggcgcgc agaccgtcgc caacatgctc gtcagtagct cccccggtca gctgctcgtg | 1320 |
| ggcaactggg gcgtgccacc cgtcgtgccg agtgccaccg agcacaccgt gctgcagacg | 1380 |

-continued

```
ctccgccaga gcgacaaccc cttcctcgac tcgcacgtga tccagggccg ccgcgtgctg    1440
cccatgaccc tggccgtggg ctacatggcg caccaggcgc agagcatcta cgcgggccac    1500
cagctgtggg ccgtcgagga cgcccagctc ttcaagggca tcgccatcga caatggcgcc    1560
gacgtgcccg tgcgcgtgga gctgtcgcgc gcaaggagg agcaggagga cgccggcaag     1620
gtcaaggtca aggtgcaggt gctgctcaaa tcgcaggtca acggcaagtc ggtgcccgcg    1680
tacaaggcga ccgtcgtgct gtcccctgcg ccgcgcccca gcgtcatcac gcgtgacttc    1740
gacctcaccc cggacccggc ctgcacggag cacgacctct acgacggcaa gacgctcttc    1800
cacggcaagg ccttccaggg catcgagcag gtgctctcgg cgacgcccaa gcagctcacc    1860
gccaagtgcc gcaatttgcc cctcacgccc gagcagcgcg ccagttcgt cgttaacctc     1920 agccagcagg acccgttcca ggcggacatt gcgttccagg cgatgctcgt ctgggcgcgc    1980
atgctgcgcc aatcggcggc cctgcccaac aactgcgagc gcttcgactt ttacaagccg    2040
atggccccgg cgccaccta ctacacgtcg gtcaagctgg cctcggcctc acccttggtg     2100
gactctgtgt gcaagtgcac cgtggcgatg cacgatgagc aaggtgaggt gtacttttct    2160
gctcgtgcca gcgtcgtc                                                  2178

<210> SEQ ID NO 26
<211> LENGTH: 726
<212> TYPE: PRT
<213> ORGANISM: Schizochytrium sp.

<400> SEQUENCE: 26

Ala Leu Gln Ala Ala Leu Thr Ser Val Glu Ala Gln Phe Gly Lys Val
1               5                   10                  15

Gly Gly Phe Val Phe Gln Phe Gly Asp Asp Val Gln Ala Gln Leu
            20                  25                  30

Gly Trp Ala Leu Leu Ala Ala Lys His Leu Lys Thr Ser Leu Ser Glu
        35                  40                  45

Gln Ile Glu Gly Gly Arg Thr Phe Phe Val Ala Val Ala Arg Leu Asp
    50                  55                  60

Gly Gln Leu Gly Leu Ser Gly Lys Ser Thr Thr Ala Thr Val Asp Leu
65                  70                  75                  80

Ser Arg Ala Gln Gln Gly Ser Val Phe Gly Leu Cys Lys Thr Leu Asp
                85                  90                  95

Leu Glu Trp Pro Ala Val Phe Cys Arg Gly Ile Asp Leu Ala Ala Asp
            100                 105                 110

Leu Asp Ala Ala Gln Ala Ala Arg Cys Leu Leu Gly Glu Leu Ser Asp
        115                 120                 125

Pro Asp Val Ala Val Arg Glu Ser Gly Tyr Ser Ala Ser Gly Gln Arg
    130                 135                 140

Cys Thr Thr Thr Thr Lys Ser Leu Thr Thr Gly Lys Pro His Gln Pro
145                 150                 155                 160

Ile Ser Ser Ser Asp Leu Phe Leu Val Ser Gly Gly Ala Arg Gly Ile
                165                 170                 175

Thr Pro Leu Cys Val Arg Glu Leu Ala Gln Arg Val Gly Gly Gly Thr
            180                 185                 190

Tyr Val Leu Ile Gly Arg Ser Glu Leu Pro Thr Thr Glu Pro Ala Trp
        195                 200                 205

Ala Val Gly Val Glu Ser Gly Lys Pro Leu Glu Lys Ala Ala Leu Ala
    210                 215                 220
```

```
Phe Leu Lys Ala Glu Phe Ala Ala Gly Arg Gly Ala Lys Pro Thr Pro
225                 230                 235                 240

Met Leu His Lys Lys Leu Val Gly Ala Val Val Gly Ala Arg Glu Val
            245                 250                 255

Arg Ala Ser Leu Ala Glu Ile Thr Ala Gln Gly Ala Thr Ala Val Tyr
        260                 265                 270

Glu Ser Cys Asp Val Ser Ser Ala Ala Lys Val Arg Glu Met Val Glu
    275                 280                 285

Arg Val Gln Gln Gln Gly Gly Arg Arg Val Ser Gly Val Phe His Ala
290                 295                 300

Ser Gly Val Leu Arg Asp Lys Leu Val Glu Asn Lys Ser Leu Ala Asp
305                 310                 315                 320

Phe Ser Ala Val Tyr Asp Thr Lys Val Gly Gly Leu Ile Asn Leu Leu
                325                 330                 335

Ala Cys Val Asp Leu Ala Gln Leu Arg His Leu Val Leu Phe Ser Ser
            340                 345                 350

Leu Ala Gly Phe His Gly Asn Val Gly Gln Ser Asp Tyr Ala Met Ala
        355                 360                 365

Asn Glu Ala Leu Asn Lys Leu Ala Ala His Leu Ser Ala Val His Pro
370                 375                 380

Gln Leu Cys Ala Arg Ser Ile Cys Phe Gly Pro Trp Asp Gly Gly Met
385                 390                 395                 400

Val Thr Pro Ala Leu Lys Ala Asn Phe Ile Arg Met Gly Ile Gln Ile
                405                 410                 415

Ile Pro Arg Gln Gly Gly Ala Gln Thr Val Ala Asn Met Leu Val Ser
            420                 425                 430

Ser Ser Pro Gly Gln Leu Leu Val Gly Asn Trp Gly Val Pro Pro Val
        435                 440                 445

Val Pro Ser Ala Thr Glu His Thr Val Leu Gln Thr Leu Arg Gln Ser
    450                 455                 460

Asp Asn Pro Phe Leu Asp Ser His Val Ile Gln Gly Arg Arg Val Leu
465                 470                 475                 480

Pro Met Thr Leu Ala Val Gly Tyr Met Ala His Gln Ala Gln Ser Ile
                485                 490                 495

Tyr Ala Gly His Gln Leu Trp Ala Val Glu Asp Ala Gln Leu Phe Lys
            500                 505                 510

Gly Ile Ala Ile Asp Asn Gly Ala Asp Val Pro Val Arg Val Glu Leu
        515                 520                 525

Ser Arg Arg Lys Glu Gln Glu Asp Ala Gly Lys Val Lys Val Lys
    530                 535                 540

Val Gln Val Leu Leu Lys Ser Gln Val Asn Gly Lys Ser Val Pro Ala
545                 550                 555                 560

Tyr Lys Ala Thr Val Val Leu Ser Pro Ala Pro Arg Pro Ser Val Ile
                565                 570                 575

Thr Arg Asp Phe Asp Leu Thr Pro Asp Pro Ala Cys Thr Glu His Asp
            580                 585                 590

Leu Tyr Asp Gly Lys Thr Leu Phe His Gly Lys Ala Phe Gln Gly Ile
        595                 600                 605

Glu Gln Val Leu Ser Ala Thr Pro Lys Gln Leu Thr Ala Lys Cys Arg
    610                 615                 620

Asn Leu Pro Leu Thr Pro Glu Gln Arg Gly Gln Phe Val Val Asn Leu
625                 630                 635                 640

Ser Gln Gln Asp Pro Phe Gln Ala Asp Ile Ala Phe Gln Ala Met Leu
```

```
                       645                 650                 655
Val Trp Ala Arg Met Leu Arg Gln Ser Ala Ala Leu Pro Asn Asn Cys
                660                 665                 670

Glu Arg Phe Asp Phe Tyr Lys Pro Met Ala Pro Gly Ala Thr Tyr Tyr
            675                 680                 685

Thr Ser Val Lys Leu Ala Ser Ala Ser Pro Leu Val Asp Ser Val Cys
        690                 695                 700

Lys Cys Thr Val Ala Met His Asp Glu Gln Gly Glu Val Tyr Phe Ser
705                 710                 715                 720

Ala Arg Ala Ser Val Val
                725

<210> SEQ ID NO 27
<211> LENGTH: 39
<212> TYPE: DNA
<213> ORGANISM: Schizochytrium sp.

<400> SEQUENCE: 27
ctcgactcgc acgtgatcca gggccgccgc gtgctgccc                          39

<210> SEQ ID NO 28
<211> LENGTH: 13
<212> TYPE: PRT
<213> ORGANISM: Schizochytrium sp.

<400> SEQUENCE: 28

Leu Asp Ser His Val Ile Gln Gly Arg Arg Val Leu Pro
1               5                   10

<210> SEQ ID NO 29
<211> LENGTH: 1341
<212> TYPE: DNA
<213> ORGANISM: Schizochytrium sp.

<400> SEQUENCE: 29
gataacattg cggtcgtggg catggcggtg cagtatgccg atgcaagaa  ccaggacgag     60 ttctgggata cgctgatgcg taaggagatc aactcgagcc cgatctcggc ggagcgcctc    120
ggtacgcgct accgcgacct ccacttccac ccgcagcgca gcaagtacgc cgacaccttc    180
tgcaacgatc gctacggctg cgtcgatgcc agcgtcgaca acgagcacga cctcctcgcc    240
gacctggccc ggcgcgccct gctcgacgcc ggaattaacc tcgacgacgc cagcaccacc    300
gccaacctac gcgacttcgg catcgtgagc ggctgcctgt cgttccccat ggacaatctg    360
cagggcgagc tgctcaatct gtaccaagtg catgtggaga accgcgtggg cgcccagcgc    420
ttccgcgact cgcgccccctg gtcggagcgc ccgcgcgctg tctcgcccga ggccagcgac    480
ccgcgcgtgt actccgaccc ggcgtccttc gtggccaacc agctcggcct ggggcccgtg    540
cgctacagcc tcgatgcagc ctgcgcgtcg cgctgtact gcctcaagct ggcgtccgac    600
cacttgctct cgcgcagcgc ggacgtgatg ctgtgcggcg ccacatgctt ccggacccg     660 ttcttcattc tctcggggtt ctccaccttc caggcgatgc cgctgggcgg accggacgat    720
aacccactgt ccgtgccgct gcggcagggc agccagggcc tgacgcccgg agagggcggc    780
gccatcatgg tgctgaagcg cctcgaggac gccgtgcgcg acggcgaccg catctacggc    840
accttgctcg gcacgagtct gagcaacgcc gggtgcggcc tgccgctgag cccgcacctg    900
ccgagcgaga agtcgtgcat ggaggacctg tacacgagcg tcggcatcga cccaagcgag    960
gtgcagtacg tggagtgcca cgccacgggc actccgcagg gcgacgtcgt ggaggtagag   1020
```

```
gcgctgcgcc actgctttcg aggtaacacg gaccacccgc cgcgcatggg ctccaccaag    1080
ggcaactttg ccacactctc cgtggcggcc gggttcgcag gcatggccaa ggtgctgctg    1140
tcgatgcagc acggcacgat cccgcccacg cccggtgtcg accgctccaa ctgcatcgac    1200
ccgctcgtcg tggacgaggc catcccttgg ccgtactcgt cggcgcaggc gcgggcaggc    1260
aaaccaggcg atgagctcaa gtgcgcctcg ctctccgcct ttggctttgg tggaaccaac    1320
gcgcactgtg tcttccgtga g                                              1341

<210> SEQ ID NO 30
<211> LENGTH: 447
<212> TYPE: PRT
<213> ORGANISM: Schizochytrium sp.

<400> SEQUENCE: 30
```

Asp Asn Ile Ala Val Gly Met Ala Val Gln Tyr Ala Gly Cys Lys
1               5                   10                  15

Asn Gln Asp Glu Phe Trp Asp Thr Leu Met Arg Lys Glu Ile Asn Ser
            20                  25                  30

Ser Pro Ile Ser Ala Glu Arg Leu Gly Thr Arg Tyr Arg Asp Leu His
        35                  40                  45

Phe His Pro Gln Arg Ser Lys Tyr Ala Asp Thr Phe Cys Asn Asp Arg
    50                  55                  60

Tyr Gly Cys Val Asp Ala Ser Val Asp Asn Glu His Asp Leu Leu Ala
65                  70                  75                  80

Asp Leu Ala Arg Arg Ala Leu Leu Asp Ala Gly Ile Asn Leu Asp Asp
                85                  90                  95

Ala Ser Thr Thr Ala Asn Leu Arg Asp Phe Gly Ile Val Ser Gly Cys
            100                 105                 110

Leu Ser Phe Pro Met Asp Asn Leu Gln Gly Glu Leu Leu Asn Leu Tyr
        115                 120                 125

Gln Val His Val Glu Asn Arg Val Gly Ala Gln Arg Phe Arg Asp Ser
    130                 135                 140

Arg Pro Trp Ser Glu Arg Pro Arg Ala Val Ser Pro Glu Ala Ser Asp
145                 150                 155                 160

Pro Arg Val Tyr Ser Asp Pro Ala Ser Phe Val Ala Asn Gln Leu Gly
                165                 170                 175

Leu Gly Pro Val Arg Tyr Ser Leu Asp Ala Ala Cys Ala Ser Ala Leu
            180                 185                 190

Tyr Cys Leu Lys Leu Ala Ser Asp His Leu Leu Ser Arg Ser Ala Asp
        195                 200                 205

Val Met Leu Cys Gly Ala Thr Cys Phe Pro Asp Pro Phe Phe Ile Leu
    210                 215                 220

Ser Gly Phe Ser Thr Phe Gln Ala Met Pro Leu Gly Gly Pro Asp Asp
225                 230                 235                 240

Asn Pro Leu Ser Val Pro Leu Arg Gln Gly Ser Gln Gly Leu Thr Pro
                245                 250                 255

Gly Glu Gly Gly Ala Ile Met Val Leu Lys Arg Leu Glu Asp Ala Val
            260                 265                 270

Arg Asp Gly Asp Arg Ile Tyr Gly Thr Leu Leu Gly Thr Ser Leu Ser
        275                 280                 285

Asn Ala Gly Cys Gly Leu Pro Leu Ser Pro His Leu Pro Ser Glu Lys
    290                 295                 300

Ser Cys Met Glu Asp Leu Tyr Thr Ser Val Gly Ile Asp Pro Ser Glu

```
                305                 310                 315                 320
Val Gln Tyr Val Glu Cys His Ala Thr Gly Thr Pro Gln Gly Asp Val
                325                 330                 335

Val Glu Val Glu Ala Leu Arg His Cys Phe Arg Gly Asn Thr Asp His
                340                 345                 350

Pro Pro Arg Met Gly Ser Thr Lys Gly Asn Phe Gly His Thr Leu Val
                355                 360                 365

Ala Ala Gly Phe Ala Gly Met Ala Lys Val Leu Leu Ser Met Gln His
            370                 375                 380

Gly Thr Ile Pro Pro Thr Pro Gly Val Asp Arg Ser Asn Cys Ile Asp
385                 390                 395                 400

Pro Leu Val Val Asp Glu Ala Ile Pro Trp Pro Tyr Ser Ser Ala Gln
                405                 410                 415

Ala Arg Ala Gly Lys Pro Gly Asp Glu Leu Lys Cys Ala Ser Leu Ser
                420                 425                 430

Ala Phe Gly Phe Gly Gly Thr Asn Ala His Cys Val Phe Arg Glu
            435                 440                 445

<210> SEQ ID NO 31
<211> LENGTH: 1293
<212> TYPE: DNA
<213> ORGANISM: Schizochytrium sp.

<400> SEQUENCE: 31
ggaccgattg ccatcatcgg gatggacgcg acgtttggta ccctcaaggg cctggacgcg       60
tttgagcagg ccatctacaa gggcacggac ggcgccagcg acctgccgag caagcgctgg     120
cggttcctgg gcgccgacac ggacttcttg accgccatgg gcctcgacgc cgtgccgcgc     180
gggtgctacg tgcgcgacgt ggacgtggac tacaagcggc tgcggtcgcc gatgatccct     240
gaggacgtcc tgcgcccgca acagctgctg gcggtggcta cgatggaccg cgcgctgcag     300
gacgctggaa tggcgacggg aggcaaggtg gcggtgctgg tggggctcgg cacggacacc     360
gagctgtacc ggcaccgcgc gcgcgtgaca ctcaaggagc ggctcgaccc ggccgcgttc     420
tcgcccgagc aggtgcagga gatgatggac tacatcaacg actgcggcac ctcgacgtcg     480
tacacgtcgt acatcggcaa cctcgtggcc acgcgcgtgt cctcgcagtg gggctttacg     540
ggcccgtcct tcaccgtcac cgaaggcgca aactcggtct accgctgcct cgagctgggc     600
aagttcctgc tcgacacgca ccaggtggac gccgtcgtgg tggccggcgt cgacctctgt     660
gccaccgccg agaacctttta cctcaaggcg cgccgctccg ccatcagccg acaggaccac     720
cctcgcgcca actttgaggc cagcgccgac gggtactttg ccggcgaggg cagcggcgcc     780
ctggtcctca gcgccaggc cgacgttggc tcagacgaca aggtctacgc cagtgtcgcg     840
ggcctcacgt gcgccgcgca gcccgctgaa gccgtgtcgc cgctactact ccaagtccac     900
aacgacgaca acgagaagag ggtggtggag atggtggagc tcgccgccga ctcgggtcgc     960
catgcgccgc acttggccaa ctcgccgctg agcgccgagt cgcagctgga gcaagtgtcc    1020
aagttgctcg cgcaccaggt gccgggctcg gtggccatcg gcagcgtgcg cgccaacgtg    1080
ggagacgtcg ggtacgcctc gggcgccgcg agcctcatca agacggcgct gtgcctccac    1140
aaccgctacc tcccggccaa cccgcagtgg gagcggccgg tggcgccggt ctccgaggcg    1200
ctgtttactt gcccgcgctc gcgtgcctgg ctgaagaacc cgggcgagtc gcgactggcg    1260
gctgtcgcca gtgcctccga gagcgggtcc tgc                                 1293
```

<210> SEQ ID NO 32
<211> LENGTH: 431
<212> TYPE: PRT
<213> ORGANISM: Schizochytrium sp.

<400> SEQUENCE: 32

Gly Pro Ile Ala Ile Gly Met Asp Ala Thr Phe Gly Thr Leu Lys
1               5                   10                  15

Gly Leu Asp Ala Phe Glu Gln Ala Ile Tyr Lys Gly Thr Asp Gly Ala
            20                  25                  30

Ser Asp Leu Pro Ser Lys Arg Trp Arg Phe Leu Gly Ala Asp Thr Asp
        35                  40                  45

Phe Leu Thr Ala Met Gly Leu Asp Ala Val Pro Arg Gly Cys Tyr Val
    50                  55                  60

Arg Asp Val Asp Val Asp Tyr Lys Arg Leu Arg Ser Pro Met Ile Pro
65                  70                  75                  80

Glu Asp Val Leu Arg Pro Gln Gln Leu Leu Ala Val Ala Thr Met Asp
                85                  90                  95

Arg Ala Leu Gln Asp Ala Gly Met Ala Thr Gly Gly Lys Val Ala Val
            100                 105                 110

Leu Val Gly Leu Gly Thr Asp Thr Glu Leu Tyr Arg His Arg Ala Arg
        115                 120                 125

Val Thr Leu Lys Glu Arg Leu Asp Pro Ala Ala Phe Ser Pro Glu Gln
    130                 135                 140

Val Gln Glu Met Met Asp Tyr Ile Asn Asp Cys Gly Thr Ser Thr Ser
145                 150                 155                 160

Tyr Thr Ser Tyr Ile Gly Asn Leu Val Ala Thr Arg Val Ser Ser Gln
                165                 170                 175

Trp Gly Phe Thr Gly Pro Ser Phe Thr Val Thr Glu Gly Ala Asn Ser
            180                 185                 190

Val Tyr Arg Cys Leu Glu Leu Gly Lys Phe Leu Leu Asp Thr His Gln
        195                 200                 205

Val Asp Ala Val Val Val Ala Gly Val Asp Leu Cys Ala Thr Ala Glu
    210                 215                 220

Asn Leu Tyr Leu Lys Ala Arg Arg Ser Ala Ile Ser Arg Gln Asp His
225                 230                 235                 240

Pro Arg Ala Asn Phe Glu Ala Ser Ala Asp Gly Tyr Phe Ala Gly Glu
                245                 250                 255

Gly Ser Gly Ala Leu Val Leu Lys Arg Gln Ala Asp Val Gly Ser Asp
            260                 265                 270

Asp Lys Val Tyr Ala Ser Val Ala Gly Leu Thr Cys Ala Ala Gln Pro
        275                 280                 285

Ala Glu Ala Val Ser Pro Leu Leu Gln Val His Asn Asp Asn
    290                 295                 300

Glu Lys Arg Val Val Glu Met Val Glu Leu Ala Ala Asp Ser Gly Arg
305                 310                 315                 320

His Ala Pro His Leu Ala Asn Ser Pro Leu Ser Ala Glu Ser Gln Leu
                325                 330                 335

Glu Gln Val Ser Lys Leu Leu Ala His Gln Val Pro Gly Ser Val Ala
            340                 345                 350

Ile Gly Ser Val Arg Ala Asn Val Gly Asp Val Gly Tyr Ala Ser Gly
        355                 360                 365

Ala Ala Ser Leu Ile Lys Thr Ala Leu Cys Leu His Asn Arg Tyr Leu
    370                 375                 380

Pro Ala Asn Pro Gln Trp Glu Arg Pro Val Ala Pro Val Ser Glu Ala
385                 390                 395                 400

Leu Phe Thr Cys Pro Arg Ser Arg Ala Trp Leu Lys Asn Pro Gly Glu
            405                 410                 415

Ser Arg Leu Ala Ala Val Ala Ser Ala Ser Glu Ser Gly Ser Cys
        420                 425                 430

<210> SEQ ID NO 33
<211> LENGTH: 1203
<212> TYPE: DNA
<213> ORGANISM: Schizochytrium sp.

<400> SEQUENCE: 33

```
acgccggaga agctggagaa ggagttggag ctggcagcca agggtgtacc gcgaagcgcc     60
aaggccgggc gcaactggat gtcgccatcg ggcagcgcct ttgcgccgac acctgtgacc    120
agcgaccgcg tcgcgttcat gtacggcgag ggccgcagcc cctactacgg cgtcgggctc    180
gacctgcacc gcctgtggcc ggctttgcac gagcgcatca acgacaagac cgcggcgctg    240
tgggagaacg gcgactcgtg gctcatgccg cgcgcggtgg atgccgactc gcagcgcgcc    300
gtgcagacgg cctttgacgc ggaccagatc gagatgttcc gcacgggcat cttcgtgtcc    360
atctgcctca ccgactacgc gcgcgacgtg ctcggggtgc agcccaaggc gtgcttcggc    420
ctcagcctcg gcgagatctc catgctcttt gcgctgtcgc gacgcaactg cggcctgtcg    480
gaccagctca cgcagcgcct acgcacctcg ccggtgtggt cgacacagct ggcggtggag    540
ttccaggcct tgcgcaagct atggaacgtg ccggcggacg cccccgtgga gtccttctgg    600
cagggctact tggttcgcgc cagccgcgcc gaaatcgaga aggcgatcgg gcccgacaac    660
cgcttcgtgc gcctgctgat cgtcaacgac tcgagcagcg cgctgatcgc cggcaaacct    720
gccgagtgtc tgcgcgtgct ggagcgcctg ggcgggcggt gccgccgat gcccgtcaag    780
caaggcatga ttgggcactg ccccgaagtg gcgccctaca cgcccgggcat cgcgcacatc    840
cacgagattt tggagattcc ggacagcccc gtcaagatgt acacctcggt caccaacgcc    900
gagctgcgcg ggggcagcaa cagcagcatc accgagttcg tgcagaagtt gtacacgcgc    960
atcgccgact ttccgggcat cgtcgacaag gtcagccgtg acggccacga tgtcttcgtc   1020
gaggtggggc cgaacaacat gcgctccgcc gcggtcagtg acattcttgg caaggctgcc   1080
accccgcatg tctccgtggc gctggaccgc cccagtgagt cggcgtggac gcagaccctc   1140
aagtcgctgg cgctgctgac cgcccaccgc gtgcccctgc acaacccgac tctgtttgcg   1200
gac                                                                1203
```

<210> SEQ ID NO 34
<211> LENGTH: 401
<212> TYPE: PRT
<213> ORGANISM: Schizochytrium sp.

<400> SEQUENCE: 34

Thr Pro Glu Lys Leu Glu Lys Glu Leu Glu Leu Ala Ala Lys Gly Val
1               5                   10                  15

Pro Arg Ser Ala Lys Ala Gly Arg Asn Trp Met Ser Pro Ser Gly Ser
            20                  25                  30

Ala Phe Ala Pro Thr Pro Val Thr Ser Asp Arg Val Ala Phe Met Tyr
        35                  40                  45

Gly Glu Gly Arg Ser Pro Tyr Tyr Gly Val Gly Leu Asp Leu His Arg
    50                  55                  60

| | | | | | | | | | | | | | | | |
|---|---|---|---|---|---|---|---|---|---|---|---|---|---|---|---|
|Leu|Trp|Pro|Ala|Leu|His|Glu|Arg|Ile|Asn|Asp|Lys|Thr|Ala|Ala|Leu|
|65| | | | |70| | | |75| | | | |80| |
|Trp|Glu|Asn|Gly|Asp|Ser|Trp|Leu|Met|Pro|Arg|Ala|Val|Asp|Ala|Asp|
| | | | |85| | | | |90| | | | |95| |
|Ser|Gln|Arg|Ala|Val|Gln|Thr|Ala|Phe|Asp|Ala|Asp|Gln|Ile|Glu|Met|
| | | |100| | | | |105| | | | |110| | |
|Phe|Arg|Thr|Gly|Ile|Phe|Val|Ser|Ile|Cys|Leu|Thr|Asp|Tyr|Ala|Arg|
| | |115| | | | |120| | | | |125| | | |
|Asp|Val|Leu|Gly|Val|Gln|Pro|Lys|Ala|Cys|Phe|Gly|Leu|Ser|Leu|Gly|
| |130| | | | |135| | | | |140| | | | |
|Glu|Ile|Ser|Met|Leu|Phe|Ala|Leu|Ser|Arg|Arg|Asn|Cys|Gly|Leu|Ser|
|145| | | | |150| | | | |155| | | | |160|
|Asp|Gln|Leu|Thr|Gln|Arg|Leu|Arg|Thr|Ser|Pro|Val|Trp|Ser|Thr|Gln|
| | | | |165| | | | |170| | | | |175| |
|Leu|Ala|Val|Glu|Phe|Gln|Ala|Leu|Arg|Lys|Leu|Trp|Asn|Val|Pro|Ala|
| | | |180| | | | |185| | | | |190| | |
|Asp|Ala|Pro|Val|Glu|Ser|Phe|Trp|Gln|Gly|Tyr|Leu|Val|Arg|Ala|Ser|
| | |195| | | | |200| | | | |205| | | |
|Arg|Ala|Glu|Ile|Glu|Lys|Ala|Ile|Gly|Pro|Asp|Asn|Arg|Phe|Val|Arg|
| |210| | | | |215| | | | |220| | | | |
|Leu|Leu|Ile|Val|Asn|Asp|Ser|Ser|Ala|Leu|Ile|Ala|Gly|Lys|Pro|
|225| | | | |230| | | | |235| | | | |240|
|Ala|Glu|Cys|Leu|Arg|Val|Leu|Glu|Arg|Leu|Gly|Gly|Arg|Leu|Pro|Pro|
| | | | |245| | | | |250| | | | |255| |
|Met|Pro|Val|Lys|Gln|Gly|Met|Ile|Gly|His|Cys|Pro|Glu|Val|Ala|Pro|
| | | |260| | | | |265| | | | |270| | |
|Tyr|Thr|Pro|Gly|Ile|Ala|His|Ile|His|Glu|Ile|Leu|Glu|Ile|Pro|Asp|
| | |275| | | | |280| | | | |285| | | |
|Ser|Pro|Val|Lys|Met|Tyr|Thr|Ser|Val|Thr|Asn|Ala|Glu|Leu|Arg|Gly|
| |290| | | | |295| | | | |300| | | | |
|Gly|Ser|Asn|Ser|Ser|Ile|Thr|Glu|Phe|Val|Gln|Lys|Leu|Tyr|Thr|Arg|
|305| | | | |310| | | | |315| | | | |320|
|Ile|Ala|Asp|Phe|Pro|Gly|Ile|Val|Asp|Lys|Val|Ser|Arg|Asp|Gly|His|
| | | | |325| | | | |330| | | | |335| |
|Asp|Val|Phe|Val|Glu|Val|Gly|Pro|Asn|Asn|Met|Arg|Ser|Ala|Ala|Val|
| | | |340| | | | |345| | | | |350| | |
|Ser|Asp|Ile|Leu|Gly|Lys|Ala|Ala|Thr|Pro|His|Val|Ser|Val|Ala|Leu|
| | |355| | | | |360| | | | |365| | | |
|Asp|Arg|Pro|Ser|Glu|Ser|Ala|Trp|Thr|Gln|Thr|Leu|Lys|Ser|Leu|Ala|
| |370| | | | |375| | | | |380| | | | |
|Leu|Leu|Thr|Ala|His|Arg|Val|Pro|Leu|His|Asn|Pro|Thr|Leu|Phe|Ala|
|385| | | | |390| | | | |395| | | | |400|
|Asp| | | | | | | | | | | | | | | |

<210> SEQ ID NO 35
<211> LENGTH: 1273
<212> TYPE: DNA
<213> ORGANISM: Schizochytrium sp.

<400> SEQUENCE: 35
tacgacgtgg actggccgct ctacatgggc gccatggcgg aaggcatctc gtcggtagac    60
ctggtggtcg ctgccgccga ggcccgcatg ctggcatcat tcggagcggc ccgcttgcct    120
atggaccagg tggaactcca gatccgtgag atccagcaac gcacctccaa cgcctttgct    180

-continued

```
gtcaacctga tgccgggtcc tgacgaggcc gcgacggtgg acgcgctgct gcgcacgggc     240
gtctcaatcg tcgaggcatc gggctacacc ggcgcgctct ctgcagacct ggtgcgctac     300
cgtgtcacgg gtctgcgacg aactagttgc ggtgcttctg tgtcggcgac tcaccgtgtg     360
gtcgccaagg tgtcgcgcac cgaggtggcc gagcactttc tgcgcccggc gccggccgcc     420
gtactagagg ctttggtcgc cgccaaacag attacgcccg agcaggccgc gctggccagc     480
cgcgtcgcca tggccgacga cgtcgcggtg gaggccgact cgggcgggca caccgacaac     540
cgaccgatcc acgtgctgct gccgctcgtg gtggcgcagc gcaaccgctg cgccacctg     600 gtggacacgc cagtgcgcgt cggcgccggc ggcgggatcg cctgtccgcg cgccgcgctg     660
ctcgcctttt ccctgggcgc cgcctttgtg gtcaccgggt ccgtcaacca actggcccgc     720
gaggctggca ccagcgacgc ggtccgacta ctgctggcga cggccaccta ctcggacgtg     780
gccatggcgc cgggcggcgt ccaggtgctc aagaagcaga ccatgttcgc cgcgcgggcc     840
acgatgctcg cccagctgca ggccaagttc ggctcctttg acgccgtgcc ggagccgcag     900
ctgcgcaagc tcgagcgctc cgtgttcaag cagtccgtgg cggacgtgtg ggctgctgca     960
cgcgaaaagt ttggtgtcga cgctaccgct gcaagtccgc aggagaggat ggcgctctgt    1020
gtgcgctggt acatgtcgca gtcgtcgcga tgggctaccg aggcgacgtc cgcgcgcaag    1080
gcggactacc agatctggtg cggccccgcc atcggcagct tcaacgactt cgttcgcggc    1140
accaagctgg acgcgaccgc tggcaccggc gagtttccgc gcgtcgtgga catcaaccag    1200
cacatcctcc tcggagcctc gcactaccgc cgcgtgcagc aacaacaaca ggacgacgac    1260
gtagaataca tca                                                       1273
```

<210> SEQ ID NO 36
<211> LENGTH: 401
<212> TYPE: PRT
<213> ORGANISM: Schizochytrium sp.

<400> SEQUENCE: 36

Tyr Asp Val Asp Trp Pro Leu Tyr Met Gly Ala Met Ala Glu Gly Ile
1               5                   10                  15

Ser Ser Val Asp Leu Val Val Ala Ala Glu Ala Arg Met Leu Ala
            20                  25                  30

Ser Phe Gly Ala Ala Arg Leu Pro Met Asp Gln Val Glu Leu Gln Ile
        35                  40                  45

Arg Glu Ile Gln Gln Arg Thr Ser Asn Ala Phe Ala Val Asn Leu Met
    50                  55                  60

Pro Gly Pro Asp Glu Ala Ala Thr Val Asp Ala Leu Leu Arg Thr Gly
65                  70                  75                  80

Val Ser Ile Val Glu Ala Ser Gly Tyr Thr Gly Ala Leu Ser Ala Asp
                85                  90                  95

Leu Val Arg Tyr Arg Val Thr Gly Leu Arg Arg Thr Ser Cys Gly Ala
            100                 105                 110

Ser Val Ser Ala Thr His Arg Val Ala Lys Val Ser Arg Thr Glu
        115                 120                 125

Val Ala Glu His Phe Leu Arg Pro Ala Pro Ala Val Leu Glu Ala
    130                 135                 140

Leu Val Ala Ala Lys Gln Ile Thr Pro Glu Gln Ala Ala Leu Ala Ser
145                 150                 155                 160

Arg Val Ala Met Ala Asp Asp Val Ala Val Glu Ala Asp Ser Gly Gly
                165                 170                 175

His Thr Asp Asn Arg Pro Ile His Val Leu Leu Pro Leu Val Val Ala
            180                 185                 190

Gln Arg Asn Arg Trp Arg His Leu Val Asp Thr Pro Val Arg Val Gly
        195                 200                 205

Ala Gly Gly Gly Ile Ala Cys Pro Arg Ala Ala Leu Leu Ala Phe Ser
    210                 215                 220

Leu Gly Ala Ala Phe Val Val Thr Gly Ser Val Asn Gln Leu Ala Arg
225                 230                 235                 240

Glu Ala Gly Thr Ser Asp Ala Val Arg Leu Leu Ala Thr Ala Thr
            245                 250                 255

Tyr Ser Asp Val Ala Met Ala Pro Gly Gly Val Gln Val Leu Lys Lys
        260                 265                 270

Gln Thr Met Phe Ala Ala Arg Ala Thr Met Leu Ala Gln Leu Gln Ala
    275                 280                 285

Lys Phe Gly Ser Phe Asp Ala Val Pro Glu Pro Gln Leu Arg Lys Leu
    290                 295                 300

Glu Arg Ser Val Phe Lys Gln Ser Val Ala Asp Val Trp Ala Ala Ala
305                 310                 315                 320

Arg Glu Lys Phe Gly Val Asp Ala Thr Ala Ala Ser Pro Gln Glu Arg
            325                 330                 335

Met Ala Leu Cys Val Arg Trp Tyr Met Ser Gln Ser Ser Arg Trp Ala
        340                 345                 350

Thr Glu Ala Thr Ser Ala Arg Lys Ala Asp Tyr Gln Ile Trp Cys Gly
    355                 360                 365

Pro Ala Ile Gly Ser Phe Asn Asp Phe Val Arg Gly Thr Lys Leu Asp
    370                 375                 380

Ala Thr Ala Gly Thr Gly Glu Phe Pro Arg Val Val Asp Ile Asn Gln
385                 390                 395                 400

His

<210> SEQ ID NO 37
<211> LENGTH: 1350
<212> TYPE: DNA
<213> ORGANISM: Schizochytrium sp.

<400> SEQUENCE: 37
atgacatcat cgaagaagac tcccgtgtgg gagatgagca aggaggagct gctggacggc     60
aagacggtgg tcttcgacta caacgagctg ctcgaattcg ccgagggcga cgtgggccaa    120
gtgttcggac ccgagttcga catcatcgac aagtaccggc gtcgcgtgcg gctgccggcg    180
cgcgagtacc tgctcgtgtc gcgcgtgacg ctgatggacg ccgaggtgaa caacttccgc    240
gtcgggtcgc gcatggtgac cgagtacgac gtgcccgtga acggggagct gtcggagggc    300
ggggacgtgc cgtgggcggt gctggtggag tcggggcagt gcgacctgat gctcatctcg    360
tacatgggca tcgacttcca gtgcaagggc gaccgcgtgt accgcctgct caacacatcg    420
ctcaccttct tcggggtggc gcacgagggc gagacgctgg tgtacgacat ccgcgtcacg    480
gggttcgcca agggcgcggg cggggagatc tcgatgttct tcttcgagta cgactgcttc    540
gtggacggcc gctgctgat cgagatgcgc gacgggtgcg ccgggttctt cacggacgcc    600
gagctggccg ccggcaaggg cgtgcttaag accaaggcgg agctggcggc gcgcgcgcag    660
atccagaagc aggacatcgc gccctttgcg ccggcgccgt gctcgcacaa gacctcgctg    720
gacgcgcgcg agatgcggct gctcgtggac cgccagtggg cgcgcgtctt cggcagcggc    780
atggcgggca tcgactacaa gttgtgcgct cgcaagatgc tcatgatcga ccgcgtcacg    840

```
cacctcgacc cgcgcggcgg cgcgcacggc ctcgggctgc tgatcgggga gaaggtgctg    900
gagcgcgacc actggtactt ccoctgccac tttgtgcgcg acgaggtgat ggccgggtcg    960
ctggtcagcg acggctgctc gcagctcctc aaggtgtaca tgctgtggct cggcctgcac   1020
acgaccgtgg gcgcgttcga ctttcgtccc gtgagcgggc acgccaacaa ggtgcggtgc   1080
cgcgggcaga tctcaccgca aagggcaag ctcgtgtacg tgatggagat caaggaaatg    1140
ggctttgacg cgaagacggg cgatccgttt gcgatcgcgg acgtggacat catcgacgtc   1200
aacttcgagg agggacaggc gtttgcggga gtggaagacc tgcacagcta cggccagggc   1260
gacctccgca agaagatcgt cgtcgacttc aagggcatcg cgctctccct gcagaagcgg   1320
aaggagcagc agaaggaaag catgaccgtg                                    1350
```

<210> SEQ ID NO 38
<211> LENGTH: 450
<212> TYPE: PRT
<213> ORGANISM: Schizochytrium sp.

<400> SEQUENCE: 38

```
Met Thr Ser Ser Lys Lys Thr Pro Val Trp Glu Met Ser Lys Glu Glu
1               5                   10                  15

Leu Leu Asp Gly Lys Thr Val Val Phe Asp Tyr Asn Glu Leu Leu Glu
            20                  25                  30

Phe Ala Glu Gly Asp Val Gly Gln Val Phe Gly Pro Glu Phe Asp Ile
        35                  40                  45

Ile Asp Lys Tyr Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

Gly Val Ala His Glu Gly Glu Thr Leu Val Tyr Asp Ile Arg Val Thr
145                 150                 155                 160

Gly Phe Ala Lys Gly Ala Gly Gly Glu Ile Ser Met Phe Phe Glu
                165                 170                 175

Tyr Asp Cys Phe Val Asp Gly Arg Leu Leu Ile Glu Met Arg Asp Gly
            180                 185                 190

Cys Ala Gly Phe Phe Thr Asp Ala Glu Leu Ala Ala Gly Lys Gly Val
        195                 200                 205

Leu Lys Thr Lys Ala Glu Leu Ala Ala Arg Ala Gln Ile Gln Lys Gln
    210                 215                 220

Asp Ile Ala Pro Phe Ala Pro Ala Pro Cys Ser His Lys Thr Ser Leu
225                 230                 235                 240

Asp Ala Arg Glu Met Arg Leu Leu Val Asp Arg Gln Trp Ala Arg Val
                245                 250                 255

Phe Gly Ser Gly Met Ala Gly Ile Asp Tyr Lys Leu Cys Ala Arg Lys
            260                 265                 270

Met Leu Met Ile Asp Arg Val Thr His Leu Asp Pro Arg Gly Gly Ala
```

```
                275                 280                 285
His Gly Leu Gly Leu Leu Ile Gly Glu Lys Val Leu Glu Arg Asp His
    290                 295                 300
Trp Tyr Phe Pro Cys His Phe Val Arg Asp Glu Val Met Ala Gly Ser
305                 310                 315                 320
Leu Val Ser Asp Gly Cys Ser Gln Leu Leu Lys Val Tyr Met Leu Trp
                325                 330                 335
Leu Gly Leu His Thr Thr Val Gly Ala Phe Asp Phe Arg Pro Val Ser
            340                 345                 350
Gly His Ala Asn Lys Val Arg Cys Arg Gly Gln Ile Ser Pro His Lys
            355                 360                 365
Gly Lys Leu Val Tyr Val Met Glu Ile Lys Glu Met Gly Phe Asp Ala
        370                 375                 380
Lys Thr Gly Asp Pro Phe Ala Ile Ala Asp Val Asp Ile Ile Asp Val
385                 390                 395                 400
Asn Phe Glu Glu Gly Gln Ala Phe Ala Gly Val Glu Asp Leu His Ser
                405                 410                 415
Tyr Gly Gln Gly Asp Leu Arg Lys Lys Ile Val Asp Phe Lys Gly
            420                 425                 430
Ile Ala Leu Ser Leu Gln Lys Arg Lys Glu Gln Gln Lys Glu Ser Met
            435                 440                 445
Thr Val
    450

<210> SEQ ID NO 39
<211> LENGTH: 1200
<212> TYPE: DNA
<213> ORGANISM: Schizochytrium sp.

<400> SEQUENCE: 39
tacccgccgc gggcggtgtg cttctcgccg ttccccaaca acccgcttga caacgaccac      60
acgccgggcc agatgccgtt gacctggttc aacatgtccg aattcatgtg cggcaaagtg     120
tccaactgcc tgggccccga gtttgcgcgc ttcgacgcga gcaagacgag ccgcagcccg     180
gcctttgacc tggcgctcgt gacgcgggtg acgagcgtgg cggacatgga gcacgggccg     240
ttctacaacg tggacgtcaa cccgggccag ggcacgatgg tgggcgagtt cgactgtccc     300
gcggacgcgt ggttcttcgg cgcctcgagc gcgacgacc acatgccgta ctcgatcctg     360
atggagatcg cgctgcagac gtcgggcgtc ctcacctcgg tgctcaaggc gccgctgacg     420
atggacaagg acgacatcct cttccgcaac ctcgacgcag acgccgagct cgtgggcgac     480
gccatgccgg acgtgcgcgg caagacgatc cgcaacttca ccaagtgcac aggctacagc     540
atgctcggca agatgggcat ccaccgcttc acctttgagc tcagcgtcga cggcgccgtc     600
ttctacaagg gcagcaccct cgtttggctg ttcgtccccg aggtcttcga gtcgcagacc     660
ggtctcgaca acggcaagcc gcgcctgcct tggtaccgcg agaacaacgt cgccgtcgac     720
acgctctccg cgcccgcctc cgcttcctcc gcgcaaggtc agctgcagct gcagcgacgc     780
gggtcgcagg cgcagttcct ggacacaatc cacctggcgg cagcggcgc cggcgtgcac     840
ggccagggct acgcgcacgg ggagaaggcc gtgaacaagc aagattggtt cttctcgtgc     900
cacttctggt cgaccccgt gatgcccggg tccctgggca tcgagtcgat gttccagctc     960
gtcgaggcgt ggtgcgtgaa gcagggactc cgggcgcggc acggcatcgc tcacccagtg    1020
ttcgcgcacg cgcccggggc cacgagctgg aagtaccgcg ggcagctaac ccccaagaac    1080
```

```
gaccgcatgg acagcgaggt gcacatcaag tcggtggcgg ccttctcctc ctgggtcgac    1140
gtcgtcgcgg acgggttcct cttcgtcgac ggcctccgcg tctactcggc agacaacctc    1200
```

<210> SEQ ID NO 40
<211> LENGTH: 400
<212> TYPE: PRT
<213> ORGANISM: Schizochytrium sp.

<400> SEQUENCE: 40

```
Tyr Pro Pro Arg Ala Val Cys Phe Ser Pro Phe Pro Asn Asn Pro Leu
1               5                   10                  15

Asp Asn Asp His Thr Pro Gly Gln Met Pro Leu Thr Trp Phe Asn Met
            20                  25                  30

Ser Glu Phe Met Cys Gly Lys Val Ser Asn Cys Leu Gly Pro Glu Phe
        35                  40                  45

Ala Arg Phe Asp Ala Ser Lys Thr Ser Arg Ser Pro Ala Phe Asp Leu
    50                  55                  60

Ala Leu Val Thr Arg Val Thr Ser Val Ala Asp Met Glu His Gly Pro
65                  70                  75                  80

Phe Tyr Asn Val Asp Val Asn Pro Gly Gln Gly Thr Met Val Gly Glu
                85                  90                  95

Phe Asp Cys Pro Ala Asp Ala Trp Phe Phe Gly Ala Ser Ser Arg Asp
            100                 105                 110

Asp His Met Pro Tyr Ser Ile Leu Met Glu Ile Ala Leu Gln Thr Ser
        115                 120                 125

Gly Val Leu Thr Ser Val Leu Lys Ala Pro Leu Thr Met Asp Lys Asp
    130                 135                 140

Asp Ile Leu Phe Arg Asn Leu Asp Ala Asp Ala Glu Leu Val Gly Asp
145                 150                 155                 160

Ala Met Pro Asp Val Arg Gly Lys Thr Ile Arg Asn Phe Thr Lys Cys
                165                 170                 175

Thr Gly Tyr Ser Met Leu Gly Lys Met Gly Ile His Arg Phe Thr Phe
            180                 185                 190

Glu Leu Ser Val Asp Gly Ala Val Phe Tyr Lys Gly Ser Thr Ser Phe
        195                 200                 205

Gly Trp Phe Val Pro Glu Val Phe Glu Ser Gln Thr Gly Leu Asp Asn
    210                 215                 220

Gly Lys Pro Arg Leu Pro Trp Tyr Arg Glu Asn Asn Val Ala Val Asp
225                 230                 235                 240

Thr Leu Ser Ala Pro Ala Ser Ala Ser Ala Gln Gly Gln Leu Gln
                245                 250                 255

Leu Gln Arg Arg Gly Ser Gln Ala Gln Phe Leu Asp Thr Ile His Leu
            260                 265                 270

Ala Gly Ser Gly Ala Gly Val His Gly Gln Gly Tyr Ala His Gly Glu
        275                 280                 285

Lys Ala Val Asn Lys Gln Asp Trp Phe Phe Ser Cys His Phe Trp Phe
    290                 295                 300

Asp Pro Val Met Pro Gly Ser Leu Gly Ile Glu Ser Met Phe Gln Leu
305                 310                 315                 320

Val Glu Ala Trp Cys Val Lys Gln Gly Leu Ala Ala Arg His Gly Ile
                325                 330                 335

Ala His Pro Val Phe Ala His Ala Pro Gly Ala Thr Ser Trp Lys Tyr
            340                 345                 350

Arg Gly Gln Leu Thr Pro Lys Asn Asp Arg Met Asp Ser Glu Val His
```

355                 360                 365
Ile Lys Ser Val Ala Ala Phe Ser Ser Trp Val Asp Val Ala Asp
            370                 375                 380
Gly Phe Leu Phe Val Asp Gly Leu Arg Val Tyr Ser Ala Asp Asn Leu
385                 390                 395                 400

<210> SEQ ID NO 41
<211> LENGTH: 1353
<212> TYPE: DNA
<213> ORGANISM: Schizochytrium sp.

<400> SEQUENCE: 41

| | | |
|---|---|---|
| cagctggacg cggggagcga ggtgcccgcc tgcgcggtga cgacctgggc cgatagggc | 60 |
| ttcatggaga cgtacggggt ggtggcgccg ctgtacagcg gggcgatggc caagggcatc | 120 |
| gcgtcggcgg acctggtgat cgcgatgggc cagcgcaaga tgctggggtc gtttggcgcg | 180 |
| ggcgggctcc cgatgcacgt cgtgcgcgcg gggattgaga agatccaggc agcgctgcca | 240 |
| gcggggccat acgcggtcaa cctgattcac tcgccttttg acgccaacct ggagaagggc | 300 |
| aacgtggacc tcttcctgga agggcgtg cgcgtcgtgg aggcgtcggc cttcatggag | 360 |
| ctcacgcccc aggtggtgcg ctaccgcgcg acgggcctct ctcgcgacgc gcgcggcggc | 420 |
| tccgtgcgca cggcccacaa gatcatcggc aaggtcagcc gcaccgagct ggccgagatg | 480 |
| tttatccggc ccgcgccgca agccattctc gacaagcttg tggcgtccgg cgagatcacc | 540 |
| cccgagcagg cggcgctggc gctcgaggtg cccatggcgg acgacatcgc cgtcgaggcc | 600 |
| gattcggggcg gcacaccga caaccgcccc atccacgtca cctgcccct catcctcagc | 660 |
| ctgcgcaacc gcctccagcg cgagctcaag taccctgcgc gacaccgcgt gcgcgtcggc | 720 |
| gccgggggcg catcgggtg cccgcaagcg gctctgggcg ccttccacat gggcgccgcg | 780 |
| tttgtggtga cgggcacggt caaccagctg agccggcagg ccgggacatg cgacaatgtg | 840 |
| cggcggcagc tgtcgcgcgc gacgtactcg gacatcacga tggcgccggc ggcggacatg | 900 |
| ttcgagcagg gcgtcgagct gcaggtgctc aagaagggca cgatgtttcc ctcgcgcgcc | 960 |
| aagaagctgt cgagctgtt tcacaagtac gactcgttcg aggcgatgcc ggcggacgag | 1020 |
| ctggcgcgcg tcgagaagcg catcttcagc aagtcactcg ccgaggtgtg ggccgagacc | 1080 |
| aaggacttct acatcacgcg gctcaacaac ccggagaaga tccgcaaggc ggagaacgag | 1140 |
| gaccccaagc tcaagatgtc actctgcttc cgctggtacc tcgggctcag ctcgttctgg | 1200 |
| gccaacaacg gcatcgcgga ccgcacgatg gactaccaga tctggtgcgg ccctgccatc | 1260 |
| ggcgccttca cgacttcat cgccgactcg tacctcgacg tggccgtctc gggcgagttc | 1320 |
| cccgacgtcg tgcagatcaa cctgcagatc ctg | 1353 |

<210> SEQ ID NO 42
<211> LENGTH: 451
<212> TYPE: PRT
<213> ORGANISM: Schizochytrium sp.

<400> SEQUENCE: 42

Gln Leu Asp Ala Gly Ser Glu Val Pro Ala Cys Ala Val Ser Asp Leu
1               5                   10                  15

Gly Asp Arg Gly Phe Met Glu Thr Tyr Gly Val Val Ala Pro Leu Tyr
                20                  25                  30

Ser Gly Ala Met Ala Lys Gly Ile Ala Ser Ala Asp Leu Val Ile Ala
            35                  40                  45

```
Met Gly Gln Arg Lys Met Leu Gly Ser Phe Gly Ala Gly Gly Leu Pro
     50                  55                  60
Met His Val Val Arg Ala Gly Ile Glu Lys Ile Gln Ala Ala Leu Pro
 65                  70                  75                  80
Ala Gly Pro Tyr Ala Val Asn Leu Ile His Ser Pro Phe Asp Ala Asn
             85                  90                  95
Leu Glu Lys Gly Asn Val Asp Leu Phe Leu Glu Lys Gly Val Arg Val
             100                 105                 110
Val Glu Ala Ser Ala Phe Met Glu Leu Thr Pro Gln Val Val Arg Tyr
             115                 120                 125
Arg Ala Thr Gly Leu Ser Arg Asp Ala Arg Gly Gly Ser Val Arg Thr
 130                 135                 140
Ala His Lys Ile Ile Gly Lys Val Ser Arg Thr Glu Leu Ala Glu Met
 145                 150                 155                 160
Phe Ile Arg Pro Ala Pro Gln Ala Ile Leu Asp Lys Leu Val Ala Ser
                 165                 170                 175
Gly Glu Ile Thr Pro Glu Gln Ala Ala Leu Ala Leu Glu Val Pro Met
                 180                 185                 190
Ala Asp Asp Ile Ala Val Glu Ala Asp Ser Gly Gly His Thr Asp Asn
             195                 200                 205
Arg Pro Ile His Val Ile Leu Pro Leu Ile Leu Ser Leu Arg Asn Arg
 210                 215                 220
Leu Gln Arg Glu Leu Lys Tyr Pro Ala Arg His Arg Val Arg Val Gly
 225                 230                 235                 240
Ala Gly Gly Gly Ile Gly Cys Pro Gln Ala Ala Leu Gly Ala Phe His
                 245                 250                 255
Met Gly Ala Ala Phe Val Val Thr Gly Thr Val Asn Gln Leu Ser Arg
             260                 265                 270
Gln Ala Gly Thr Cys Asp Asn Val Arg Arg Gln Leu Ser Arg Ala Thr
             275                 280                 285
Tyr Ser Asp Ile Thr Met Ala Pro Ala Ala Asp Met Phe Glu Gln Gly
 290                 295                 300
Val Glu Leu Gln Val Leu Lys Lys Gly Thr Met Phe Pro Ser Arg Ala
 305                 310                 315                 320
Lys Lys Leu Phe Glu Leu Phe His Lys Tyr Asp Ser Phe Glu Ala Met
                 325                 330                 335
Pro Ala Asp Glu Leu Ala Arg Val Glu Lys Arg Ile Phe Ser Lys Ser
                 340                 345                 350
Leu Ala Glu Val Trp Ala Glu Thr Lys Asp Phe Tyr Ile Thr Arg Leu
                 355                 360                 365
Asn Asn Pro Glu Lys Ile Arg Lys Ala Glu Asn Glu Asp Pro Lys Leu
 370                 375                 380
Lys Met Ser Leu Cys Phe Arg Trp Tyr Leu Gly Leu Ser Ser Phe Trp
 385                 390                 395                 400
Ala Asn Asn Gly Ile Ala Asp Arg Thr Met Asp Tyr Gln Ile Trp Cys
                 405                 410                 415
Gly Pro Ala Ile Gly Ala Phe Asn Asp Phe Ile Ala Asp Ser Tyr Leu
                 420                 425                 430
Asp Val Ala Val Ser Gly Glu Phe Pro Asp Val Val Gln Ile Asn Leu
             435                 440                 445
Gln Ile Leu
 450
```

METHOD OF INCREASING OMEGA-3 POLYUNSATURATED FATTY ACIDS PRODUCTION IN MICROALGAE

CROSS-REFERENCE TO RELATED APPLICATIONS

This application is a National Stage of International Application No. PCT/EP2017/061347 filed May 11, 2017, and which claims the benefit of the filing date of U.S. Provisional Patent Application No. 62/335,498 filed May 12, 2016, the entire contents of each of which are hereby incorporated herein by reference in their entireties.

TECHNICAL FIELD

The present disclosure relates to methods of increasing the production of omega-3 polyunsaturated fatty acids, such as eicosapentaenoic acid (EPA), in microalgae by altering the expression level of genes encoding the subunits of a polyunsaturated fatty acid synthase. For example, methods of increasing the production of EPA by increasing the expression level of PFA1 encoding polyunsaturated fatty acid synthase subunit 1 (PFA1), and/or PFA3 encoding polyunsaturated fatty acid synthase subunit 3 (PFA3) are disclosed. The present disclosure further relates to recombinant microalgae modified to alter the expression level of genes encoding a polyunsaturated fatty acid synthase, such as PFA1 and/or PFA3. The present disclosure further relates to methods of manipulating the ratio of omega-3 polyunsaturated fatty acids to omega-6 polyunsaturated fatty acids, such as manipulation of the ratio of EPA to docosahexaenoic acid (DHA) produced in microalgae.

BACKGROUND

Thraustochytrids are microorganisms of the order Thraustochytriales, including members of the genus *Thraustochytrium* and the genus *Schizochytrium*, and have been recognized as an important source of PUFAs. See, e.g., U.S. Pat. No. 5,130,242. It has been shown that polyketide synthase (PKS)-like systems in marine bacteria and thraustochytrids are capable of synthesizing polyunsaturated fatty acids (PUFAs) from acetyl-CoA and malonyl-CoA. These PKS-like systems are also referred to herein as PUFA synthase systems. PUFA synthase systems in the marine bacteria *Shewanella* and *Vibrio marinus* are described in U.S. Pat. No. 6,140,486. A PUFA synthase system in a thraustochytrid of the genus Schizochytrium is described in U.S. Pat. No. 6,566,583. PUFA synthase systems in thraustochytrids of the genus Schizochytrium (ATCC 20888) and the genus Thraustochytrium (ATCC 20892) are also described in U.S. Pat. Nos. 7,247,461 and 7,256,022. U.S. Pat. No. 7,211,418 describes a PUFA synthase system in a thraustochytrid of the genus Thraustochytrium and the production of eicosapentaenoic acid (C20:5, omega-3) (EPA) and other PUFAs using the system. U.S. Pat. No. 7,217,856 describes PUFA synthase systems in *Shewanella olleyana* and *Shewanella japonica*. WO 2005/097982 describes a PUFA synthase system in strain SAM2179. U.S. Pat. Nos. 7,208,590 and 7,368,552 describe PUFA synthase genes and proteins from *Thraustochytrium aureum*.

Recently, a PUFA synthase system from the *Schizochytrium* sp. ATCC PTA-9695 was described in U.S. Pat. No. 8,940,884. When expressed, the PUFA synthases from Schizochytrium sp. ATCC PTA-9695 (PFA1, PFA2, and PFA3) produce unique fatty acid profiles, characterized in part by high levels of omega-3 fatty acids. A schematic of the gene architecture for the PUFA synthases from *Schizochytrium* sp. ATCC PTA-9695 (PFA1, PFA2, and PFA3) is provided in FIG. 1. A schematic of the domain architecture for the PUFA synthases in several of the thraustochytrids mentioned above is provided in FIG. 2.

PKS systems have been traditionally described in the literature as falling into one of three basic types, typically referred to as Type I (modular or iterative), Type II, and Type III. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the Type II fatty acid synthase (FAS) systems found in plants and bacteria. Type I iterative PKS systems are similar to the Type II system in that the enzymes are used in an iterative fashion to produce the end product. The Type I iterative system differs from the Type II system in that enzymatic activities, instead of being associated with separable proteins, occur as domains of larger proteins. This system is analogous to the Type I FAS systems found in animals and fungi.

In contrast to the Type II systems, each enzyme domain in the Type I modular PKS systems is used only once in the production of the end product. The domains are found in very large proteins and the product of each reaction is passed on to another domain in the PKS protein.

Type III systems have been more recently discovered and belong to the plant chalcone synthase family of condensing enzymes. Type III PKS systems are distinct from Type I and Type II PKS systems and utilize free CoA substrates in iterative condensation reactions to usually produce a heterocyclic end product.

In the conventional or standard pathway for PUFA synthesis, medium chain-length saturated fatty acids (products of a fatty acid synthase (FAS) system) are modified by a series of elongation and desaturation reactions. The substrates for the elongation reaction are fatty acyl-CoA (the fatty acid chain to be elongated) and malonyl-CoA (the source of the two carbons added during each elongation reaction). The product of the elongase reaction is a fatty acyl-CoA that has two additional carbons in the linear chain. The desaturases create cis double bonds in the pre-existing fatty acid chain by extraction of two hydrogens in an oxygen-dependent reaction. The substrates for the desaturases are either acyl-CoA (in some animals) or the fatty acid that is esterified to the glycerol backbone of a phospholipid (e.g., phosphatidylcholine).

Fatty acids are classified based on the length and saturation characteristics of the carbon chain. Fatty acids are termed short chain, medium chain, or long chain fatty acids based on the number of carbons present in the chain, are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

PUFAs are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 PUFA with a chain length of 22 carbons and 6 double bonds, often designated as "22:6 n-3." Other omega-3 PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates. Roche, H. M., Proc. Nutr. Soc. 58: 397-401 (1999). DHA, for example, accounts for approximately 15%-20% of lipids in the human cerebral cortex, and 30%-60% of lipids in the retina, is concentrated in the testes and sperm, and is an important component of breast milk. Bergé, J. P., and Barnathan, G. Adv. Biochem. Eng. Biotechnol. 96:49-125 (2005). DHA accounts for up to 97% of the omega-3 fatty acids in the brain and up to 93% of the omega-3 fatty acids in the retina. Moreover, DHA is essential for both fetal and infant development, as well as maintenance of cognitive functions in adults. Id. Because omega-3 fatty acids are not synthesized de novo in the human body, these fatty acids must be derived from nutritional sources.

Flaxseed oil and fish oils are considered good dietary sources of omega-3 fatty acids. Flaxseed oil contains no EPA, DHA, DPA, or ARA but rather contains linolenic acid (C18:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

Efforts have been made to produce PUFAs in oilseed crop plants by modification of the endogenously-produced fatty acids. Genetic modification of these plants with various individual genes for fatty acid elongases and desaturases has produced leaves or seeds containing PUFAs such as EPA and DHA (Ruiz-Lopez et al., Appl. Microbiol. Biotechnol. 99:143-154 (2015); Qi et al., Nature Biotech. 22:739 (2004); PCT Publ. No. WO 04/071467; Abbadi et al., Plant Cell 16:1 (2004)); Napier and Sayanova, Proc. Nutrition Society 64:387-393 (2005); Robert et al., Functional Plant Biology 32:473-479 (2005); and U.S. Appl. Publ. No. 2004/0172682).

Oils produced from thraustochytrids often have simpler polyunsaturated fatty acid profiles than corresponding fish or microalgal oils (Lewis, T. E., Mar. Biotechnol. 1: 580-587 (1999)). Strains of thraustochytrid species have been reported to produce omega-3 fatty acids as a high percentage of the total fatty acids produced by the organisms (See U.S. Pat. No. 5,130,242; Huang, J. et al., J. Am. Oil. Chem. Soc. 78: 605-610 (2001); Huang, J. et al., Mar. Biotechnol. 5: 450-457 (2003)). However, isolated thraustochytrids vary in the identity and amounts of PUFAs produced, such that some previously described strains can have undesirable PUFA profiles.

As such, a continuing need exists for methods to produce desirable PUFA profiles through recombinant modification of single cell organisms. The solution to this technical problem is provided by the embodiments characterized in the claims.

SUMMARY OF INVENTION

The present disclosure provides a method for producing lipids enriched in omega-3 polyunsaturated fatty acids (PUFAs), such as EPA, comprising modifying a microalga to alter the expression level of genes encoding a polyunsaturated fatty acid synthase (PUFA synthase) and culturing the modified microalga under conditions wherein lipids enriched in omega-3 PUFAs are produced. For example, methods of the invention include altering the expression level of PFA1 which encodes polyunsaturated fatty acid synthase subunit 1 (PFA1), and/or altering the expression level of PFA2 which encodes polyunsaturated fatty acid synthase subunit 2 (PFA2), and/or altering the expression level of PFA3 which encodes polyunsaturated fatty acid synthase subunit 3 (PFA3). In one embodiment, the microalga is modified to increase the expression level of PFA1 and/or PFA3. In some embodiments, the microalga is modified to increase the expression level of PFA1. In other embodiments, the microalga is modified to increase expression of PFA1 and PFA3.

In some embodiments, the microalga to be modified is a Labyrinthulomycetes. In some embodiments, the microalga to be modified is a thraustochytrid, preferably a Schizochytrium or a Thraustochytrium. In a preferred embodiment, the microalga to be modified is a Schizochytrium. In a specific embodiment, the microalga to be modified is Schizochytrium sp. ATCC 20888, or a derivative thereof.

In one embodiment, the microalga is modified to contain multiple copies of a gene encoding PFA1 and/or a gene encoding PFA3. In a preferred embodiment, the microalga is modified to contain multiple copies of a gene encoding PFA1. In one embodiment, the microalga contains between 2 and 10 copies of a gene encoding PFA1. In another embodiment, the microalga contains between 3 and 7 copies of a gene encoding PFA1. In an additional embodiment, the microalga contains between 4 and 6 copies of a gene encoding PFA1.

In another embodiment, the microalga is modified to contain multiple copies of both a gene encoding PFA1 and a gene encoding PFA3.

In another embodiment, the microalga is modified to overexpress a gene encoding PFA1 and/or a gene encoding PFA3 by promoter engineering. For example, a construct of the invention may be modified to insert and/or replace one or more promoters which drive the expression of the gene encoding PFA1 and/or a gene encoding PFA3 to increase expression levels of these genes in the recombinant microalga.

In some embodiments, the genes encoding PFA1, PFA2, and/or PFA3 are derived from a Labyrinthulomycetes that endogenously produces EPA-rich lipids. In one embodiment, the genes encoding PFA1, PFA2, and/or PFA3 are derived from a Schizochytrium that endogenously produces EPA-rich lipids. In a preferred embodiment, the genes encoding PFA1, PFA2, and/or PFA3 are derived from Schizochytrium sp. ATCC PTA-9695, or are functional equivalents thereof. EPA-rich lipids are defined as lipids having a significant level of EPA, such as lipids containing at least 5% EPA. In other embodiments, lipids having a significant level of EPA are defined as lipids containing at least 10% EPA, at least 15% EPA, at least 20% EPA, or greater.

In a preferred embodiment, one or more of the endogenous PUFA synthase genes of the microalga to be modified (i.e., the host microalga) are mutated or deleted. In a more preferred embodiment, all of the endogenous PUFA synthase genes of the microalga to be modified are mutated or deleted.

Surprisingly, it has been found that by overexpressing a gene encoding PFA1, and/or a gene encoding PFA3, in recombinant microalgae, EPA production can be increased by at least 2-fold relative to EPA production by the host microalgae. In some embodiments, EPA production by the recombinant microalgae of the invention is increased by at least 5-fold relative to EPA production by the host microalgae. In some embodiments, EPA production by the recombinant microalgae of the invention is increased by at least 10-fold relative to EPA production by the host microalgae. In a further embodiment, EPA production by the recombinant microalgae of the invention is increased by at least 20-fold relative to EPA production by the host microalgae.

Additionally, it has been found that by overexpressing a gene encoding PFA1, and/or a gene encoding PFA3, in recombinant microalgae, the EPA:docosahexaenoic acid (DHA) ratio is increased by at least 2-fold relative to EPA production by the host microalgae. In some embodiments, in the recombinant microalgae, the EPA:docosahexaenoic acid (DHA) ratio is increased by at least 10-fold relative to EPA production by the host microalgae. In some embodiments, in the recombinant microalgae of the invention, the EPA:docosahexaenoic acid (DHA) ratio is increased by at least 20 fold relative to EPA production by the host microalgae. In a further embodiment, in the recombinant microalgae of the invention, the EPA:docosahexaenoic acid (DHA) ratio is increased by at least 50 fold relative to EPA production by the host microalgae.

In some embodiments, the lipids enriched for EPA produced according to the invention are further enriched for DHA.

The present disclosure also provides a method for producing lipids with a decreased level of DPA n-6, comprising modifying a microalga to alter the expression level of genes PFA1, PFA2, and/or PFA3 and culturing the modified microalga; wherein lipids with a decreased level of DPA n-6 are produced.

The present application also relates to a recombinant organism, wherein the recombinant organism is modified to alter the expression level of genes encoding a polyunsaturated fatty acid synthase (PUFA synthase). In some embodiments, organisms of the invention may contain native PUFA synthase genes. Organisms which contain native PUFA synthase genes include, but not limited to, microalga. For example, recombinant microalgae of the invention are modified to alter the expression level of PFA1 which encodes polyunsaturated fatty acid synthase subunit 1 (PFA1), and/or alter the expression level of PFA2 which encodes polyunsaturated fatty acid synthase subunit 2 (PFA2), and/or alter the expression level of PFA3 which encodes polyunsaturated fatty acid synthase subunit 3 (PFA3). In one embodiment, the microalga is modified to increase the expression level of PFA1 and/or PFA3. In some embodiments, the microalga is modified to increase the expression level of gene PFA1. In other embodiments, the microalga is modified to increase expression of PFA1 and PFA3. In other embodiments, organisms of the invention do not contain PUFA synthase genes, including, but not limited to, plants. These organisms must first be modified to express a PUFA synthase system to allow production of polyunsaturated fatty acids. The resulting recombinant organisms, such as plants are then further modified to alter the expression level of the genes encoding a PUFA synthase.

The present application also relates to mutant microalga that have undergone a mutation process, such as selective pressure, that results in the modified expression level of genes encoding a polyunsaturated fatty acid synthase wherein the mutant microalga produces an increased level of EPA compared to the wild-type, unmutated, microalga.

The present application also relates to methods for making the above-mentioned recombinant microalgal strains. The present application further relates to the PUFA oils produced by the above-mentioned recombinant microalgal strains.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

FIG. 4 shows analyses of the fatty acid methyl ester profiles (FAME) after culture at 25° C. (FIG. 4A) or 30° C. (FIG. 4B) in the native *Schizochytrium* sp. N230D containing the endogenous PFA1, PFA2, and PFA3 PUFA synthase subunit genes compared to the recombinant *Schizochytrium* sp. N230D in which the endogenous PFA1, PFA2, and PFA3 genes have been replaced by the PFA1, PFA2, and PFA3 genes from *Schizochytrium* sp. ATCC PTA-9695 at their respective loci (strain B156-2). Of particular interest, C20:5 n-3 is EPA, C22:5 n-6 is DPA n-6, and C22:6 n-3 is DHA.

DETAILED DESCRIPTION

Figure 1:
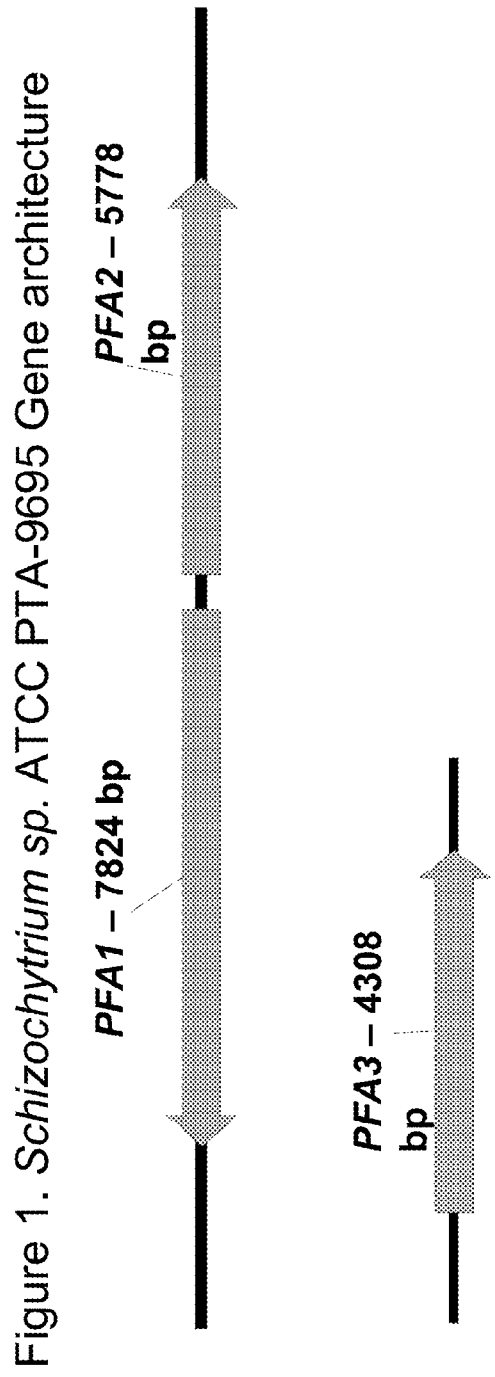
FIG. 1 shows the gene architecture of the *Schizochytrium* sp. ATCC PTA-9695 PUFA synthase subunits, PFA1, PFA2, and PFA3.
Figure 2:
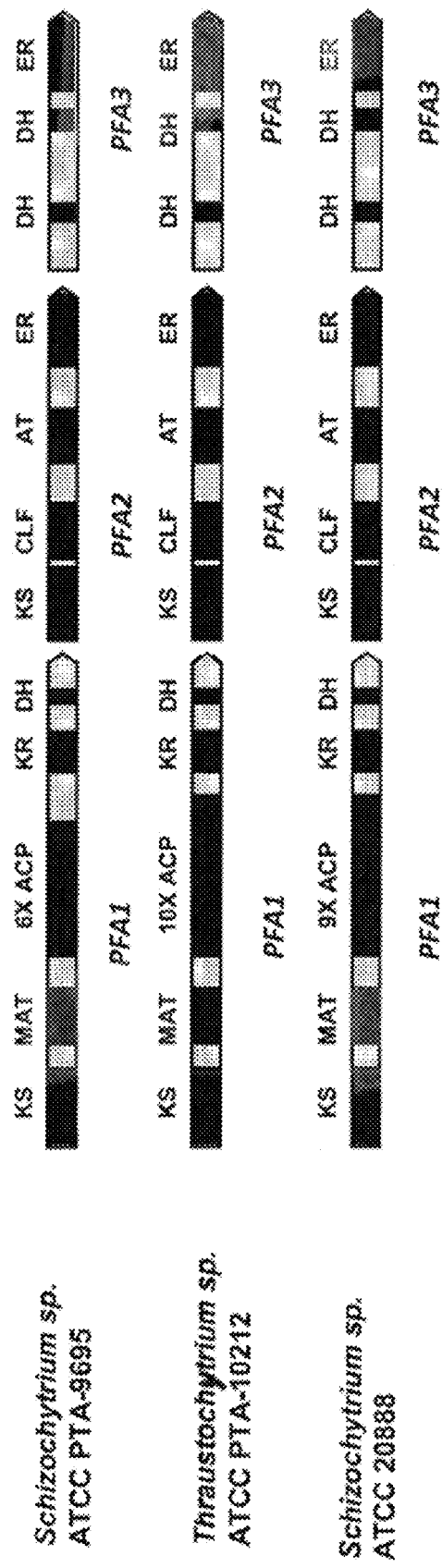
FIG. 2 shows the domain architecture of the *Schizochytrium* sp. ATCC PTA-9695, *Thraustochytrium* sp. ATCC PTA-10212, and *Schizochytrium* sp. ATCC 20888 PUFA synthases.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

As used herein, an "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein, a first nucleotide sequence is "operably linked" with a second nucleic acid sequence when the first nucleic acid sequence is in a functional relationship with the second nucleic acid sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; and polyadenylation recognition sequences. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. An "inducible" promoter may be a promoter which may be under environmental control.

Any inducible promoter can be used in some embodiments of the invention. See Ward et al. (1993) *Plant Mol. Biol.* 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) *Proc. Natl. Acad. Sci. USA* 88:0421).

Examples of promoters that can be used to drive the expression of the PFA1, PFA2 and PFA3 genes have been described in prior patents (U.S. Pat. Nos. 8,945,875, and 8,637,651). In addition, other promoters of various strengths can be selected using data generated by whole transcriptome analysis. For example, the promoters of calcium-transporting ATPase (EC 3.6.3.8) gene, NADP-specific glutamate dehydrogenase (EC 1.4.1.4) gene or acetyl-CoA acetyltransferase (EC 2.3.1.9) gene can be used for high expression throughout fermentation of *Schizochytrium* sp. N230D strain. The promoter of the sodium-dependent phosphate transporter gene can be used to induce high expression during the lipid accumulation phase of the fermentation of *Schizochytrium* sp. N230D strain. The promoters of Histone H2B gene or the aspartate-semialdehyde dehydrogenase (EC 1.2.1.11) can be used to promote high expression of PFA1 and PFA3 in the growth phase of *Schizochytrium* sp. N230D strain.

As used herein, the term "heterologous" means of different origin. For example, if a host cell is transformed with a nucleic acid that does not occur in the untransformed host cell in nature, then that nucleic acid is heterologous (and exogenous) to the host cell. Furthermore, different elements (e.g., promoter, enhancer, coding sequence, terminator, etc.) of a transforming nucleic acid may be heterologous to one another and/or to the transformed host. The term heterologous, as used herein, may also be applied to one or more nucleic acid(s) that are identical in sequence to a nucleic acid already present in a host cell, but that are now linked to different additional sequences and/or are present at a different copy number, etc.

As used herein, the term "native" refers to the form of a polynucleotide or gene in its natural location in the organism or in the genome of an organism as found in nature, with its own regulatory sequences, if present.

As used herein, the term "endogenous" refers to a polynucleotide, gene, or polypeptide that is located in the organism or genome that normally comprises the molecule in nature.

As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) *Nature* 319:791-3); lipofection (Felgner et al. (1987) *Proc. Natl. Acad. Sci. USA* 84:7413-7); microinjection (Mueller et al. (1978) *Cell* 15:579-85); *Agrobacterium*-mediated transfer (Fraley et al. (1983) *Proc. Natl. Acad. Sci. USA* 80:4803-7); direct DNA uptake; and microprojectile bombardment (Klein et al. (1987) *Nature* 327:70).

As used herein, a "transgene" is an exogenous nucleic acid sequence that is integrated into the genome of the host. In some examples, a transgene may contain regulatory sequences operably linked to a coding sequence of the transgene (e.g., a promoter).

As used herein, a "vector" is a nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, and protein coating).

As used herein, the term "expression" may refer to the transcription and stable accumulation of mRNA encoded by a polynucleotide, or to the translation of such an mRNA into a polypeptide. The term "overexpression," as used herein, refers to expression that is higher than endogenous expression of the same or a closely related gene. A heterologous gene is overexpressed if its expression is higher than that of a closely-related endogenous gene (e.g., a homolog).

As used herein, the term "exogenous" refers to one or more nucleic acid(s) that are not normally present within their specific environment or context. For example, if a host cell is transformed with a nucleic acid that does not occur in the untransformed host cell in nature, then that nucleic acid is exogenous to the host cell. The term exogenous, as used herein, also refers to one or more nucleic acid(s) that are identical in sequence to a nucleic acid already present in a host cell, but that are located in a different cellular or genomic context than the nucleic acid with the same sequence already present in the host cell. For example, a nucleic acid that is integrated in the genome of the host cell in a different location than a nucleic acid with the same sequence is normally integrated in the genome of the host cell. Furthermore, a nucleic acid (e.g., a DNA molecule) that is present in a plasmid or vector in the host cell is exogenous to the host cell when a nucleic acid with the same sequence is only normally present in the genome of the host cell.

The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "substantially identical" may refer to nucleotide sequences that are more than 80% identical. For example, a substantially identical nucleotide sequence may be at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

As used herein in the context of a nucleic acid encoding a protein, the term "optimized" refers to a nucleic acid wherein a heterologous nucleotide sequence has been changed to reflect the codon bias of a target host organism. In some embodiments, the nucleotide sequence may be further changed to remove genetic elements that may interfere with gene expression.

It will be understood that, due to the redundancy of the genetic code, multiple DNA sequences may be designed to encode a single amino acid sequence. Thus, optimized DNA sequences may be designed, for example, to remove superfluous restriction sites and undesirable RNA secondary structures, while optimizing the nucleotide sequence of the coding region so that the codon composition resembles the overall codon composition of the host in which the DNA is to be expressed. Guidance regarding the design and production of synthetic DNA sequences can be found in, for example, International Patent Application Nos. WO2013016546, WO2011146524, and WO1997013402; and U.S. Pat. Nos. 6,166,302 and 5,380,831.

As used herein, the term "conservative substitution" refers to a substitution where an amino acid residue is substituted for another amino acid in the same class. A non-conservative amino acid substitution is one where the residues do not fall into the same class, for example, substitution of a basic amino acid for a neutral or non-polar amino acid. Classes of amino acids that may be defined for the purpose of performing a conservative substitution are known in the art.

In some embodiments, a conservative substitution includes the substitution of a first aliphatic amino acid for a second, different aliphatic amino acid. For example, if a first amino acid is one of Gly; Ala; Pro; Ile; Leu; Val; and Met, the first amino acid may be replaced by a second, different amino acid selected from Gly; Ala; Pro; Ile; Leu; Val; and Met. In particular examples, if a first amino acid is one of Gly; Ala; Pro; Ile; Leu; and Val, the first amino acid may be replaced by a second, different amino acid selected from Gly; Ala; Pro; Ile; Leu; and Val. In particular examples involving the substitution of hydrophobic aliphatic amino acids, if a first amino acid is one of Ala; Pro; Ile; Leu; and Val, the first amino acid may be replaced by a second, different amino acid selected from Ala; Pro; Ile; Leu; and Val.

In some embodiments, a conservative substitution includes the substitution of a first aromatic amino acid for a second, different aromatic amino acid. For example, if a first amino acid is one of His; Phe; Trp; and Tyr, the first amino acid may be replaced by a second, different amino acid selected from His; Phe; Trp; and Tyr. In particular examples involving the substitution of uncharged aromatic amino acids, if a first amino acid is one of Phe; Trp; and Tyr, the first amino acid may be replaced by a second, different amino acid selected from Phe; Trp; and Tyr.

In some embodiments, a conservative substitution includes the substitution of a first hydrophobic amino acid for a second, different hydrophobic amino acid. For example, if a first amino acid is one of Ala; Val; Ile; Leu; Met; Phe; Tyr; and Trp, the first amino acid may be replaced by a second, different amino acid selected from Ala; Val; Ile; Leu; Met; Phe; Tyr; and Trp. In particular examples involving the substitution of non-aromatic, hydrophobic amino acids, if a first amino acid is one of Ala; Val; Ile; Leu; and Met, the first amino acid may be replaced by a second, different amino acid selected from Ala; Val; Ile; Leu; and Met.

In some embodiments, a conservative substitution includes the substitution of a first polar amino acid for a second, different polar amino acid. For example, if a first amino acid is one of Ser; Thr; Asn; Gln; Cys; Gly; Pro; Arg; His; Lys; Asp; and Glu, the first amino acid may be replaced by a second, different amino acid selected from Ser; Thr; Asn; Gln; Cys; Gly; Pro; Arg; His; Lys; Asp; and Glu. In particular examples involving the substitution of uncharged, polar amino acids, if a first amino acid is one of Ser; Thr; Asn; Gln; Cys; Gly; and Pro, the first amino acid may be replaced by a second, different amino acid selected from Ser; Thr; Asn; Gln; Cys; Gly; and Pro. In particular examples involving the substitution of charged, polar amino acids, if a first amino acid is one of His; Arg; Lys; Asp; and Glu, the first amino acid may be replaced by a second, different amino acid selected from His; Arg; Lys; Asp; and Glu. In further examples involving the substitution of charged, polar amino acids, if a first amino acid is one of Arg; Lys; Asp; and Glu, the first amino acid may be replaced by a second, different amino acid selected from Arg; Lys; Asp; and Glu. In particular examples involving the substitution of positively charged (basic), polar amino acids, if a first amino acid is one of His; Arg; and Lys, the first amino acid may be replaced by a second, different amino acid selected from His; Arg; and Lys. In further examples involving the substitution of positively charged, polar amino acids, if a first amino acid is Arg or Lys, the first amino acid may be replaced by the other amino acid of Arg and Lys. In particular examples involving the substitution of negatively charged (acidic), polar amino acids, if a first amino acid is Asp or Glu, the first amino acid may be replaced by the other amino acid of Asp and Glu.

In some embodiments, a conservative substitution includes the substitution of a first electrically neutral amino acid for a second, different electrically neutral amino acid. For example, if a first amino acid is one of Gly; Ser; Thr; Cys; Asn; Gln; and Tyr, the first amino acid may be replaced by a second, different amino acid selected from Gly; Ser; Thr; Cys; Asn; Gln; and Tyr.

In some embodiments, a conservative substitution includes the substitution of a first non-polar amino acid for a second, different non-polar amino acid. For example, if a first amino acid is one of Ala; Val; Leu; Ile; Phe; Trp; Pro; and Met, the first amino acid may be replaced by a second, different amino acid selected from Ala; Val; Leu; Ile; Phe; Trp; Pro; and Met.

In many examples, the selection of a particular second amino acid to be used in a conservative substitution to replace a first amino acid may be made in order to maximize the number of the foregoing classes to which the first and second amino acids both belong. Thus, if the first amino acid is Ser (a polar, non-aromatic, and electrically neutral amino acid), the second amino acid may be another polar amino acid (i.e., Thr; Asn; Gln; Cys; Gly; Pro; Arg; His; Lys; Asp; or Glu); another non-aromatic amino acid (i.e., Thr; Asn; Gln; Cys; Gly; Pro; Arg; His; Lys; Asp; Glu; Ala; Ile; Leu; Val; or Met); or another electrically-neutral amino acid (i.e., Gly; Thr; Cys; Asn; Gln; or Tyr). However, it may be preferred that the second amino acid in this case be one of Thr; Asn; Gln; Cys; and Gly, because these amino acids share all the classifications according to polarity, non-aromaticity, and electrical neutrality. Additional criteria that may optionally be used to select a particular second amino acid to be used in a conservative substitution are known in the art. For example, when Thr; Asn; Gln; Cys; and Gly are available to be used in a conservative substitution for Ser, Cys may be eliminated from selection in order to avoid the formation of undesirable cross-linkages and/or disulfide bonds. Likewise, Gly may be eliminated from selection, because it lacks an alkyl side chain. In this case, Thr may be selected, e.g., in order to retain the functionality of a side chain hydroxyl group. The selection of the particular second amino acid to be used in a conservative substitution is ultimately, however, within the discretion of the skilled practitioner.

As used herein, the term "polyunsaturated fatty acid" or "PUFA" refers to a fatty acid with a carbon chain length of at least 16 carbons (e.g., at least 18 carbons, at least 20 carbons, and 22 or more carbons), with at least 3 or more carbon-carbon double bonds (hereafter, "double bonds" discussed in reference to PUFAs refer to carbon-carbon bonds) (e.g., 4 or more double bonds, 5 or more double bonds, and 6 or more double bonds), wherein all double bonds are in the cis configuration.

As used herein, the term "long chain polyunsaturated fatty acid" or "LC-PUFA" refers to a fatty acid with a carbon chain length of 20 or more carbons containing 3 or more double bonds, or 22 or more carbons containing 3 or more double bonds (e.g., 4 or more double bonds, 5 or more double bonds, and 6 or more double bonds). LC-PUFAs of the ω-6 series include, for example and without limitation, di-homo-gamma-linolenic acid (C20:3 n-6), arachidonic acid (ARA; C20:4 n-6), adrenic acid (also called docosatetraenoic acid or DTA; C22:4 n-6), and docosapentaenoic acid (DPA n-6; C22:5 n-6). LC-PUFAs of the ω-3 series include, for example and without limitation, eicosatrienoic acid (C20:3 n-3), eicosatetraenoic acid (C20:4 n-3), eicosapentaenoic acid (EPA; C20:5 n-3), docosapentaenoic acid (DPA n-3; C22:5 n-3), and docosahexaenoic acid (DHA; C22:6 n-3). LC-PUFAs also include fatty acids with greater than 22 carbons and 4 or more double bonds for example and without limitation, C28:8 (n-3).

The term "PUFA synthase" as used herein refers to an enzyme that catalyzes de novo synthesis of PUFAs (e.g., LC-PUFAs). Most Thraustochytrid PUFA synthases are comprised of three subunits, designated here as PFA1, PFA2, and PFA3 (or Pfa1, Pfa2, and Pfa3). These subunits have previously been referred to as OrfA, OrfB, and OrfC (or ORFA, ORFB, and ORFC). PUFA synthases from bacteria are usually comprised of four subunits, designated PfaA, PfaB, PfaC, and PfaD. The term PUFA synthase includes, for example and without limitation, PUFA synthase systems or PUFA synthase-like systems for the production of PUFAs. Some specific PUFA synthases are designated herein by an additional notation, e.g., a PUFA synthase from *Schizochytrium* sp. ATCC Accession No. PTA-9695. The term "PUFA synthase system" refers to one or more PUFA synthase(s) and any heterologous accessory enzymes that can affect the function of the PUFA synthase (e.g., a 4'-phosphopantetheinyl transferase (PPTase) or acyl-CoA synthetase (ACS)).

The term "functional equivalent(s)" as used herein includes any PUFA synthase that catalyzes production of PUFAs or any genes and/or nucleotide sequences that encode any PUFA synthase that catalyzes production of PUFAs. A functional equivalent of PFA1 includes any polypeptide (or any gene and/or nucleotide sequence encoding a polypeptide) that possesses the same or similar enzymatic activities as PFA1. Similarly, a functional equivalent of PFA2 includes any polypeptide (or any gene and/or nucleotide sequence encoding a polypeptide) that possesses the same or similar enzymatic activities as PFA2 and a functional equivalent of PFA3 includes any polypeptide (or any gene and/or nucleotide sequence encoding a polypeptide) that possesses the same or similar enzymatic activities of PFA3. In some embodiments, a functional equivalent of a PUFA synthase subunit comprises one or more domains present within the PUFA synthase subunit. For example, a functional equivalent of PFA1 may comprise a KS domain, a MAT domain, an ACP domain, a combination of two or more ACP domains, such as two, three, four, five, six, seven, eight, nine, or ten ACP domains, including tandem domains, a KR domain, a DH domain, and combinations thereof. A functional equivalent of PFA2 may comprise a KS domain, a CLF domain, an AT domain, an ER domain, and combinations thereof. A functional equivalent of PFA3 may comprise a DH domain, an ER domain, and combinations thereof. In other embodiments, functional equivalents include, but are not limited to, additions or substitutions of amino acid residues within the reference amino acid sequence (i.e., SEQ ID NO:2; SEQ ID NO:4; SEQ ID NO:6), but which result in a silent change, thus producing a functionally equivalent gene product. For example, conservative amino acid substitutions may be made on the basis of similarity in polarity, charge, solubility, hydrophobicity, hydrophilicity, and/or the amphipathic nature of the residues involved.

The subject disclosure features, in one aspect, a method for producing lipids enriched for EPA, comprising modifying a microalga to increase the expression level of PFA1 which encodes PFA1, and/or PFA3 which encodes PFA3, and culturing the modified microalga wherein lipids enriched for EPA are produced. Also featured is a recombinant microalga in which a gene encoding PFA1 and/or a gene encoding PFA3 is overexpressed. Such recombinant microalgae have been demonstrated herein to produce very favorable fatty acid lipid profiles (e.g., increased levels of EPA, increased ratio of EPA:DHA, decreased levels of DPA n-6, etc.). Certain non-limiting embodiments of the invention are described in further detail below.

The marine Thraustochytrid *Schizochytrium* alga (as represented by ATCC Accession No. PTA-9695) produces oil with a high ω-3/ω-6 ratio that may also be used as sources of PUFA synthase genes for crop transformations. See PCT International Patent Publication No. WO2015/081270. Additionally, this Schizochytrium can produce oil that contains significant levels of EPA in addition to DHA. The ability to produce significant amounts of EPA is in contrast to some other Thraustochytrium strains (for example, *Schizochytrium* sp. ATCC Accession No. 20888). See U.S. Patent Publication No. US2013/0150599A1; PCT International Patent Publication No. WO2013/016546. In some embodiments, one or more PUFA synthase subunits derived from *Schizochytrium* sp. ATCC PTA-9695, or functional equivalents thereof, are expressed recombinantly in a microalga. In a preferred embodiment, genes encoding one or more PUFA synthase subunits from *Schizochytrium* sp. ATCC PTA-9695 are overexpressed recombinantly in a microalga. In particular, genes encoding one or more PUFA synthase subunits from *Schizochytrium* sp. ATCC PTA-9695 that are overexpressed are selected from a gene encoding PFA1 and a gene encoding PFA3, preferably a gene encoding PFA1, and optionally a gene encoding PFA3.

Methods of Producing Lipids Using Recombinant Host Cells

The present invention is directed to a method to produce at least one PUFA comprising expressing a PUFA synthase system in a host cell under conditions effective to produce PUFAs, wherein the PUFA synthase system comprises any of the isolated nucleic acid molecules and recombinant nucleic acid molecules described herein as well as combinations thereof, wherein at least one PUFA is produced. In some embodiments, the at least one PUFA includes EPA, DHA, or a combination thereof. In some embodiments, the host cell is a plant cell, an isolated animal cell, or a microbial cell. In some embodiments the host cell is a thraustochytrid.

The present invention is directed to a method to produce lipids enriched for EPA, DHA, or a combination thereof, comprising expressing at least one PUFA synthase gene in a host cell under conditions effective to produce lipids, wherein the at least one PUFA synthase gene comprises any of the isolated nucleic acid molecules and recombinant nucleic acid molecules described herein, as well as combinations thereof in the host cell, wherein lipids enriched with EPA, DHA, or a combination thereof are produced.

The present invention is also directed to a method of isolating lipids from a host cell, comprising expressing at least one PUFA synthase gene in the host cell under conditions effective to produce lipids, and isolating lipids from the host cell, wherein the PUFA synthase system in the host cell comprises any of the isolated nucleic acid molecules and recombinant nucleic acid molecules described herein as well as combinations thereof.

In some embodiments, one or more lipid fractions containing PUFAs are isolated from the host cells. In some embodiments, the one or more fractions isolated from the host cell includes the total fatty acid fraction, the sterol esters fraction, the triglyceride fraction, the free fatty acid fraction, the sterol fraction, the diacylglycerol fraction, the phospholipid fraction, or combination thereof. In some embodiments, PUFAs are isolated from the host cells, wherein the PUFAs are enriched for omega-3 fatty acids, or omega-6 fatty acids, or combinations thereof based on the composition of the PUFA synthase system introduced into a host cell. In some embodiments, the PUFAs are enriched for DHA, EPA, or a combination thereof based on the composition of the PUFA synthase system introduced into a host cell. In some embodiments, the PUFAs are enriched for DHA, EPA, or a combination thereof. In some embodiments, the PUFA profile of PUFAs isolated from a host cell include high concentrations of EPA and lower concentrations of DHA, ARA, DPA n-6, or combinations thereof. In some embodiments, the PUFA profile of PUFAs isolated from a host cell include high concentrations of DHA and EPA, and lower concentrations of ARA, DPA n-6, or combinations thereof. In some embodiments, the PUFA profile of PUFAs isolated from a host cell include high concentrations of EPA and lower concentrations of DHA, ARA, DPA n-6, or combinations thereof.

The invention is directed to a method of replacing an inactive or deleted PUFA synthase activity, introducing a new PUFA synthase activity, or enhancing an existing PUFA synthase activity in an organism having PUFA synthase activity, comprising expressing any of the isolated nucleic acid molecules and recombinant nucleic acid molecules described herein, as well as combinations thereof, in the organism under conditions effective to express the PUFA synthase activity. In some embodiments, the nucleic acid molecule comprises one or more polynucleotide sequences described herein that encode one or more of the PUFA synthase subunits; PFA1, PFA2 or PFA3. In a preferred embodiment, the nucleic acid molecule comprises one or more polynucleotide sequences described herein that encode a PFA1 and/or a PFA3. In some embodiments, the PUFA profiles of the organisms are altered by the introduction of the one or more nucleic acid molecules of the invention.

In some embodiments, the expression level of a gene encoding PFA1 and/or a gene encoding PFA3, is increased or enhanced in a recombinant host cell as described herein. In a preferred embodiment, the recombinant host cell is a microalga, such as a Thraustochytrid. As discussed in further detail in the Examples below, overexpression of a gene encoding PFA1 and/or a gene encoding PFA3 from a *Schizochytrium* that produces EPA-rich lipids in a *Schizochytrium* sp. that produces high levels of lipid, results in a more favorable PUFA profile than present in the wild-type Schizochytrium.

In some embodiments, the altered PUFA profiles include an increase in omega-3 fatty acids and a decrease in omega-6 fatty acids. In some embodiments, the amount of DHA is increased while the amounts of one or more of EPA, ARA, DPA n-6, or combinations thereof are maintained or decreased. In some embodiments, the amounts of EPA and DHA are increased while the amounts of ARA, DPA n-6, or a combination thereof are maintained or decreased. In some embodiments, the amount of EPA is increased while the amounts of one or more of DHA, ARA, DPA n-6, or combinations thereof are maintained or decreased. In some embodiments, the nucleic acid molecule comprises a polynucleotide sequence from a PFA1 coding sequence or one or more domains therein. In some embodiments, the nucleic acid molecule comprises a polynucleotide sequence encoding a PFA1 or one or more domains therein and the amount of omega-3 fatty acids in the organism is increased while the amount of omega-6 fatty acids is decreased. In some embodiments, the nucleic acid molecule comprises a polynucleotide sequence from a PFA3 coding sequence or one or more domains therein. In some embodiments, the nucleic acid molecule comprises a polynucleotide sequence encoding a PFA3 or one or more domains therein and the amount of omega-3 fatty acids in the organism is increased while the amount of omega-6 fatty acids is decreased The invention is directed to methods of increasing production of EPA, DHA, or a combination thereof in an organism having PUFA synthase activity, comprising expressing any of the isolated nucleic acid molecules and recombinant nucleic acid molecules described herein as well as combinations thereof in the organism under conditions effective to produce EPA, DHA, or a combination thereof, wherein the PUFA synthase activity replaces an inactive or deleted activity, introduces a new activity, or enhances an existing activity in the organism, and wherein production of DHA, EPA, or a combination thereof in the organism is increased.

In a preferred embodiment, the invention is directed to methods of increasing production of EPA, DHA, or a combination therein in an organism having PUFA synthase activity, comprising introduction and/or increasing the expression level of a gene encoding PFA1 and/or a gene encoding PFA3, in the organism. In some embodiments, the expression level of a gene encoding PFA1 and/or a gene encoding PFA3, in the organism is increased by the introduction of multiple copies of a nucleotide sequence encoding PFA1 and/or a nucleotide sequence encoding PFA3, into the organism. The introduction of multiple copies of a nucleotide sequence encoding PFA1, and optionally a nucleotide sequence encoding PFA3, into an organism can be either targeted or random. In another embodiment, the expression level of a nucleotide sequence encoding PFA1 and/or a nucleotide sequence encoding PFA3, in the organism is increased by the coupling of the nucleotide sequence encoding a PFA1 and/or a nucleotide sequence encoding PFA3, with a strong promoter, such as elongation factor-1 (EF-1) promoter.

PUFA Synthases

Embodiments herein include host organisms (e.g., microalgae) that are genetically modified to express a PUFA synthase. In some embodiments, an organism that has been genetically modified to express a heterologous PUFA synthase system, for example, a functional heterologous protein system comprising a PUFA synthase and at least one accessory protein thereof. The genetic modifications herein may also be used in some embodiments to improve PUFA production in a host organism that endogenously expresses a PUFA synthase.

A PUFA synthase system may comprise several multi-functional proteins (and can include single function proteins) that can act together to conduct both iterative processing of the fatty acid chain, as well as non-iterative processing, including trans-cis isomerization and enoyl reduction reactions in selected cycles. These proteins are referred to herein as the core PUFA synthase enzyme system or the core PUFA synthase. General information and details about the domains and motifs contained within these proteins may be found in, for example: U.S. Pat. Nos. 6,140,486 and 6,566,583; U.S. Patent Publication Nos. 2002/0194641, 2004/0235127, and 2005/0100995; International Patent Publication No. WO 2006/135866; and Metz et al. (2001) *Science* 293:290-3. Functional PUFA synthase domains may be found as a single protein (e.g., the domain and protein are synonymous) or as one of two or more domains in a single protein.

Numerous examples of enzymes having PUFA synthase activity, their subunits, and/or domains (and polynucleotides and genes encoding the same) are known in the art and may be combined in a genetically-modified host comprising a heterologous PUFA synthase that is disclosed herein. Such PUFA synthase enzymes (or their subunits or domains) include both bacterial and non-bacterial PUFA synthases. A non-bacterial PUFA synthase may be a eukaryotic PUFA synthase. Certain bacterial PUFA synthases are described, for example, in U.S. Patent Publication No. 2008/0050505.

In some embodiments, a heterologous PUFA synthase comprises biologically active domains selected from the group consisting of: at least one enoyl-ACP reductase (ER) domain (and, in some embodiments, two ER domains); multiple acyl carrier protein (ACP) domain(s) (e.g., at least from one to four, or at least five ACP domains, and in some embodiments up to six, seven, eight, nine, ten, or more than ten ACP domains); at least two 0-ketoacyl-ACP synthase (KS) domains; at least one acyltransferase (AT) domain (in addition to the malonyl-CoA:ACP acyltransferase domain listed below); at least one β-ketoacyl-ACP reductase (KR) domain; at least two *FabA*-like β-hydroxyacyl-ACP dehydrase (DH) domains; at least one chain length factor (CLF) domain; at least one malonyl-CoA:ACP acyltransferase (MAT) domain; and at least one DH domain that is not in the *FabA*-like DH family of DHs. In particular embodiments, a heterologous PUFA synthase also comprises at least one region containing a dehydratase conserved active site motif and which is identified as a DH domain by comparison to the Pfam protein families database (Finn et al., *Nucleic Acids Res. Database Issue* 44:D279-D285 (2016)).

In some embodiments, a heterologous PUFA synthase comprises the subunits PFA1 (SEQ ID NO: 2), PFA2 (SEQ ID NO: 4), and PFA3 (SEQ ID NO: 6) from *Schizochytrium* sp. ATCC PTA-9695, or functional equivalents thereof. See U.S. Pat. No. 8,940,884. PUFA synthases in other thraustochytrids have also been designated as ORF 1, ORF 2, and ORF 3, respectively, or as OrfA, OrfB, and OrfC, respectively. See, e.g., *Schizochytrium* sp. (ATCC-20888) and *Thraustochytrium* sp. (ATCC-20892) in U.S. Pat. Nos. 7,247,461 and 7,256,022, referring to orfA, orfB, and orfC genes and corresponding OrfA, OrfB, and OrfC proteins, and *Thraustochytrium aureum* (ATCC-34304) in U.S. Pat. No. 7,368,552, referring to ORF A, ORF B, and ORF C genes and proteins. See also, strain SAM2179 in WO/2005/097982, referring to ORF 1, ORF 2, and ORF 3 genes and proteins.

For example, a heterologous PUFA synthase system according to embodiments herein may include, for example and without limitation, at least one protein comprising an amino acid sequence having at least 80% (e.g., at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; and at least 99%) identity to SEQ ID NO: 2; SEQ ID NO:4; and/or SEQ ID NO:6. In particular examples, a heterologous PUFA synthase system includes at least one protein comprising SEQ ID NO: 2; SEQ ID NO: 4; and/or SEQ ID NO: 6. In particular examples, a heterologous PUFA synthase system comprises at least one protein having an amino acid sequence selected from the group consisting of SEQ ID NO: 2; SEQ ID NO: 4; and/or SEQ ID NO: 6.

Some embodiments include a heterologous PUFA synthase system that comprises at least one functional equivalent of SEQ ID NO: 2; SEQ ID NO: 4; and/or SEQ ID NO: 6 and at least one accessory enzyme. For example, the system may comprise a variant, portion, fragment, or derivative of SEQ ID NO: 2; SEQ ID NO: 4; and/or SEQ ID NO: 6, wherein such a system has PUFA synthase activity. For example, the polypeptide sequences of other PUFA synthases or their subunits or individual domains (and genes or polynucleotides encoding the same) can be identified in the literature and in bioinformatics databases available in the art. Such sequences may be identified, for example, through BLAST searching of publicly available databases with known PUFA synthase gene or polypeptide sequences. In such a method, identities can be based on the ClustalW method of alignment using the default parameters of GAP PENALTY=10, GAP LENGTH PENALTY=0.1, and Gonnet 250 series of protein weight matrix.

Additionally, the PUFA synthase gene or polypeptide sequences disclosed herein can be used to identify other PUFA synthase homologs in nature. For example, each of the PUFA synthase nucleic acid fragments disclosed herein can be used to isolate genes encoding homologous proteins. Isolation of homologous genes using sequence-dependent protocols is well known in the art. Examples of sequence-dependent protocols include, for example and without limitation: methods of nucleic acid hybridization; methods of DNA and RNA amplification, as exemplified by various uses of nucleic acid amplification technologies (e.g., polymerase chain reaction (PCR), ligase chain reaction (LCR), and strand displacement amplification (SDA)); and methods of library construction and screening by complementation.

In some embodiments, a heterologous PUFA synthase comprises a Schizochytrium PUFA synthase domain (e.g., ER domains, ACP domains, KS domains, AT domains, KR domains, FabA-like DH domains, CLF domains, MAT domains, and a non-FabA-like DH domain), wherein the domain is combined with one or more domains from a different PUFA synthase to form a complete PUFA synthase having PUFA synthase activity.

In some embodiments, a genetically-modified organism comprising a heterologous PUFA synthase can be further modified with at least one domain or biologically active fragment thereof of another PUFA synthase. In particular embodiments, any of the domains of a PUFA synthase may be modified from their natural structure to modify or enhance the function of that domain in the PUFA synthase system (e.g., to modify the PUFA types or ratios thereof produced by the system, see U.S. Pat. No. 8,003,772.

Nucleic Acid Molecules

As used herein, a "polynucleotide" can comprise a conventional phosphodiester bond or a non-conventional bond (e.g., an amide bond, such as found in peptide nucleic acids (PNA)). A polynucleotide can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotides can be composed of triple-stranded regions comprising RNA or DNA or both RNA and DNA. Polynucleotides can contain ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters. Polynucleotides can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms. The term nucleic acid molecule refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

The term "isolated" nucleic acid molecule refers to a nucleic acid molecule, DNA or RNA, which has been removed from its native environment. Further examples of isolated nucleic acid molecules include nucleic acid molecules comprising recombinant polynucleotides maintained in heterologous host cells or purified (partially or substantially) polynucleotides in solution. Isolated RNA molecules include in vivo or in vitro RNA transcripts of polynucleotides of the present invention. Isolated nucleic acid molecules according to the present invention further include such molecules produced synthetically. In addition, a nucleic acid molecule or polynucleotide can include a regulatory element such as a promoter, ribosome binding site, or a transcription terminator.

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

In some embodiments, the present invention is directed to isolated nucleic acid molecules comprising polynucleotide sequences at least 80% identical to the polynucleotide sequences of Schizochytrium sp. ATCC PTA-9695 PFA1 (SEQ ID NO:1), Schizochytrium sp. ATCC PTA-9695 PFA2 (SEQ ID NO:3), Schizochytrium sp. ATCC PTA-9695 PFA3 (SEQ ID NO:5), and combinations thereof, wherein the polynucleotides encode polypeptides comprising one or more activities associated with PUFA synthesis by PUFA synthases.

PUFA synthase domains can be identified by their sequence and structural homology to enzymes or domains with established biochemical activities. The presence of conserved active site motifs can provide additional evidence that the domain can have enzymatic activity. See, e.g., U.S. Pat. No. 8,940,884, incorporated by reference herein in its entirety. Examples of PUFA synthase domains include: the beta-ketoacyl-ACP synthase (KS) domain, malonyl-CoA: ACP acyltransferase (MAT) domain, acyl carrier protein (ACP) domains, ketoreductase (KR) domain, and beta-hydroxyacyl-ACP dehydrase (DH) domain in PFA1; the KS domain, chain length factor (CLF) domain, acyltransferase (AT) domain, and enoyl-ACP reductase (ER) domain in PFA2; and the DH domains and the ER domain in PFA3.

A polypeptide or domain of a polypeptide having beta-ketoacyl-ACP synthase (KS) biological activity (function) has been previously shown to be capable of carrying out the initial step of the fatty acid elongation reaction cycle. The term "beta-ketoacyl-ACP synthase" has been used interchangeably with the terms "3-keto acyl-ACP synthase," "beta-ketoacyl-ACP synthase," and "keto-acyl ACP synthase." In other systems, it has been shown that the acyl group for elongation is linked to a cysteine residue at the active site of KS by a thioester bond, and the acyl-KS undergoes condensation with malonyl-ACP to form -ketoacyl-ACP, C02, and unbound ("free") KS. In such systems, KS has been shown to possess greater substrate specificity than other polypeptides of the reaction cycle. Polypeptides (or domains of polypeptides) can be readily identified as belonging to the KS family by homology to known KS sequences.

A polypeptide or a domain of a polypeptide having malonyl-CoA:ACP acyltransferase (MAT) activity has been previously shown to be capable of transferring the malonyl moiety from malonyl-CoA to ACP. The term "malonyl-CoA:ACP acyltransferase" has been used interchangeably with "malonyl acyltransferase." In addition to the active site motif (GxSxG), MATs have been shown to possess an extended motif (R and Q amino acids in key positions). Polypeptides (or domains of polypeptides) can be readily identified as belonging to the MAT family by their homology to known MAT sequences and by their extended motif structure.

A polypeptide or a domain of a polypeptide having acyl carrier protein (ACP) activity has been previously shown to be capable of functioning as a carrier for growing fatty acyl chains via a thioester linkage to a covalently bound co-factor. ACPs are typically about 80 to about 100 amino acids long and have been shown to be converted from inactive apo-forms to functional holo-forms by transfer of the phosphopantetheinyl moiety of CoA to a highly conserved serine residue of the ACP. It has also been shown that acyl groups are attached to ACPs by a thioester linkage at the free terminus of the phosphopantetheinyl moiety. The presence of variations of an active site motif (LGIDS*) has also been recognized as a signature of ACPs. The functionality of the active site serine (S*) has been demonstrated in a bacterial PUFA synthase (Jiang et al., *J. Am. Chem. Soc.* 130:6336-7 (2008)). Polypeptides (or domains of polypeptides) can be readily identified as belonging to the ACP family by labeling with radioactive pantetheine and by sequence homology to known ACPs.

A polypeptide or a domain of a polypeptide having dehydrase or dehydratase (DH) activity has been previously shown to be capable of catalyzing a dehydration reaction. At least two domains of PUFA synthase systems have previously been demonstrated as showing homology to *FabA* DH/isomerase enzymes associated with the Type II FAS systems of some bacteria (rather than to the DH domains of other PKS systems). See, e.g., U.S. Pat. No. 7,217,856, incorporated by reference herein in its entirety. *FabA*-like enzymes have beta-hydroxyacyl-ACP dehydrase biological activity that initially produces a trans double bond in the carbon chain. In addition to the DH activity, the *FabA*-like enzymes also possess cis-trans isomerase activity (Heath et al., *J. Biol. Chem.* 271:27795 (1996)). The term "*FabA*-like beta-hydroxyacyl-ACP dehydrase" has been used interchangeably with the terms "*FabA*-like beta-hydroxy acyl-ACP dehydrase," "beta-hydroxyacyl-ACP dehydrase," and "dehydrase". Based on the demonstrated activities of the *FabA*-like DH/isomerase proteins, the domains of the PUFA synthase system with homology to those proteins could be responsible for creation of the cis double bonds in the PUFA synthase products. A polypeptide or domain can also have non-*FabA*-like DH activity, or non-*FabA*-like beta-hydroxyacyl-ACP dehydrase (DH) activity. More specifically, a conserved active site motif of about 13 amino acids in length has been previously identified in PUFA synthase DH domains: LxxHxxxGxxxxP (the L position can also be an I in the motif). See, e.g., U.S. Pat. No. 7,217,856, and Donadio S, Katz L., Gene 111(1):51-60 (1992), each of which is incorporated by reference herein in its entirety. This conserved motif is found in a similar region of all known PUFA synthase sequences and could be associated with a non-*FabA* like dehydration reaction. Additionally, the conserved motif is found in a region which is identified as a DH domain by comparison to the Pfam protein families database (Finn et al., *Nucleic Acids Res. Database Issue* 44:D279-D285 (2016).

A polypeptide or a domain of a polypeptide having beta-ketoacyl-ACP reductase (KR) activity has been previously shown to be capable of catalyzing the pyridine-nucleotide-dependent reduction of 3-ketoacyl forms of ACP. The term "beta-ketoacyl-ACP reductase" has been used interchangeably with the terms "ketoreductase," "3-ketoacyl-ACP reductase," and "keto-acyl ACP reductase." It has been determined in other systems that KR function involves the first reductive step in the de novo fatty acid biosynthesis elongation cycle. Polypeptides (or domains of polypeptides) can be readily identified as belonging to the KR family by sequence homology to known PUFA synthase KRs.

A polypeptide or a domain of a polypeptide having chain length factor (CLF) characteristics has been previously defined as having one or more of the following activities or characteristics: (1) it has been implicated in determining the number of elongation cycles and hence chain length of the end product in Type II PUFA synthase systems, (2) it has homology to KS, but lacks the KS active site cysteine, and (3) it can heterodimerize with KS. A domain with the sequence characteristics of a CLF is found in all currently identified PUFA synthase systems and in each case is found as part of a multidomain protein.

A polypeptide or a domain of a polypeptide having acyltransferase (AT) activity has been previously defined as having one or more of the following activities or characteristics: (1) it can transfer the fatty acyl group from the ACP domain(s) to water (i.e., a thioesterase), releasing the fatty acyl group as a free fatty acid, (2) it can transfer a fatty acyl group to an acceptor such as CoA, (3) it can transfer the acyl group among the various ACP domains, or (4) it can transfer the fatty acyl group to a lipophilic acceptor molecule (e.g., to lysophosphadic acid). Polypeptides (or domains of polypeptides) can be readily identified as belonging to the AT family by sequence homology to known ATs.

A polypeptide or a domain of a polypeptide having enoyl-ACP reductase (ER) biological activity has been previously shown to be capable of reducing the trans-double bond (introduced by the DH activity) in the fatty acyl-ACP, resulting in saturation of the associated carbons. The ER domain in PUFA synthase systems has previously been shown to have homology to a family of ER enzymes (Heath et al., *Nature* 406: 145-146 (2000), incorporated by reference herein in its entirety), and an ER homolog has been shown to function as an enoyl-ACP reductase in vitro (Bumpus et al. *J. Am. Chem. Soc.,* 130: 11614-11616 (2008), incorporated by reference herein in its entirety). The term "enoyl-ACP reductase" has been used interchangeably with "enoyl reductase," "enoyl ACP-reductase," and "enoyl acyl-ACP reductase." Polypeptides (or domains of polypeptides) can be readily identified as belonging to the ER family by sequence homology to known ERs.

In some embodiments, the present invention is directed to nucleic acid molecules comprising a polynucleotide sequence at least 80% identical to a polynucleotide sequence within PFA1 (SEQ ID NO:1) that encodes one or more PUFA synthase domains. In some embodiments, the nucleic acid molecule comprises a polynucleotide sequence at least 80% identical to a polynucleotide sequence within PFA1 (SEQ ID NO:1) that encodes one or more PUFA synthase domains such as a KS domain (SEQ ID NO:7), a MAT domain (SEQ ID NO:9), an ACP domain (such as any one of SEQ ID NOs: 13, 15, 17, 19, 21, or 23), a combination of two or more ACP domains, such as two, three, four, five, six, seven, eight, nine, or ten ACP domains, including tandem domains (SEQ ID NO:11 and portions thereof), a KR domain (SEQ ID NO:25), a DH domain (SEQ ID NO:27), and combinations thereof. In some embodiments, the nucleic acid molecule comprises one or more polynucleotide sequences within PFA1 (SEQ ID NO:1) that encodes one or more PUFA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA2 (SEQ ID NO:3) that encodes one or more PUFA synthase domains. In some embodiments, the nucleic acid molecule comprises a polynucleotide sequence at least 80% identical to the polynucleotide sequence within PFA2 (SEQ ID NO:3) that encodes one or more PUFA synthase domains such as a KS domain (SEQ ID NO:29), a CLF domain (SEQ ID NO:31), an AT domain (SEQ ID NO:33), an ER domain (SEQ ID NO:35), and combinations thereof. In some embodiments, the nucleic acid molecule comprises one or more polynucleotide sequences within PFA2 (SEQ ID NO:3) that encodes one or more PUFA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA3 (SEQ ID NO:5) that encodes one or more PUFA synthase domains. In some embodiments, the nucleic acid molecule comprises a polynucleotide sequence at least 80% identical to a polynucleotide sequence within PFA3 (SEQ ID NO:5) that encodes one or more PUFA synthase domains such as a DH domain (such as SEQ ID NO:37 and SEQ ID NO:39), an ER domain (SEQ ID NO:41), and combinations thereof. In some embodiments, the nucleic acid molecule comprises one or more polynucleotide sequences within PFA3 (SEQ ID NO:5) that encodes one or more PUFA synthase domains, including one or more copies of any individual domain in combination with one or more copies of any other individual domain.

In some embodiments, the present invention is directed to a nucleic acid molecule comprising a polynucleotide sequence at least 80% identical to SEQ ID NO:1, wherein the polynucleotide sequence encodes a polypeptide comprising PUFA synthase activity selected from the group consisting of KS activity, MAT activity, ACP activity, KR activity, DH activity, and combinations thereof.

In some embodiments, the present invention is directed to a nucleic acid molecule comprising a polynucleotide sequence at least 80% identical to SEQ ID NO:3, wherein the polynucleotide sequence encodes a polypeptide comprising PUFA synthase activity selected from the group consisting of KS activity, CLF activity, AT activity, ER activity, and combinations thereof.

In some embodiments, the present invention is directed to a nucleic acid molecule comprising a polynucleotide sequence at least 80% identical to SEQ ID NO:5, wherein the polynucleotide sequence encodes a polypeptide comprising PUFA synthase activity selected from the group consisting of DH activity, ER activity, and combinations thereof.

In some embodiments, the present invention is directed to a nucleic acid molecule comprising a polynucleotide sequence which encodes a functional equivalent of the PFA1 according to SEQ ID NO:2.

In some embodiments, the present invention is directed to a nucleic acid molecule comprising a polynucleotide sequence which encodes a functional equivalent of the PFA2 according to SEQ ID NO: 4.

In some embodiments, the present invention is directed to a nucleic acid molecule comprising a polynucleotide sequence which encodes a functional equivalent of the PFA3 according to SEQ ID NO: 6.

The present invention is directed to isolated nucleic acid molecules comprising polynucleotide sequences encoding polypeptides, wherein the polypeptides comprise amino acid sequences that are at least 80% identical to the amino acid sequences of PFA1 (SEQ ID NO:2), PFA2 (SEQ ID NO:4), or PFA3 (SEQ ID NO:6), wherein the polynucleotides encode polypeptides comprising one or more PUFA synthase activities.

The present invention is directed to nucleic acid molecules comprising a polynucleotide sequence encoding a polypeptide, wherein the polypeptide comprises an amino acid sequence at least 80% identical to the amino acid sequences of one or more PUFA synthase domains of the PUFA synthases of the invention.

In some embodiments, the present invention is directed to nucleic acid molecules comprising a polynucleotide sequence encoding a polypeptide, wherein the polypeptide comprises an amino acid sequence at least 80% identical to an amino acid sequence within PFA1 (SEQ ID NO:2) comprising one or more PUFA synthase domains. In some embodiments, the polypeptide comprises an amino acid sequence at least 80% identical to an amino acid sequence within PFA1 (SEQ ID NO:2) comprising one or more PUFA synthase domains such as a KS domain (SEQ ID NO: 8), a MAT domain (SEQ ID NO: 10), an ACP domain (such as any one of SEQ ID NOs: 14, 16, 18, 20, 22, or 24), a combination of two or more ACP domains, such as two, three, four, five, six, seven, eight, nine, or ten ACP domains, including tandem domains (SEQ ID NO:12, and portions thereof), a KR domain (SEQ ID NO:26), a DH domain (SEQ ID NO:28), and combinations thereof. In some embodiments, the polypeptide comprises one or more amino acid sequences within PFA1 (SEQ ID NO:2) comprising one or more PUFA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within PFA2 (SEQ ID NO:4) comprising one or more PUFA synthase domains. In some embodiments, the polypeptide comprises an amino acid sequence at least 80% identical to an amino acid sequence within PFA2 (SEQ ID NO:4) comprising one or more PUFA synthase domains such as a KS domain (SEQ ID NO:30), a CLF domain (SEQ ID NO:32), an AT domain (SEQ ID NO:34), an ER domain (SEQ ID NO:36), and combinations thereof. In some embodiments, the polypeptide comprises one or more amino acid sequences within PFA2 (SEQ ID NO:4) comprising one or more PUFA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within PFA3 (SEQ ID NO: 6) comprising one or more PUFA synthase domains. In some embodiments, the polypeptide comprises an amino acid sequence at least 80% identical to an amino acid sequence within PFA3 (SEQ ID NO:6) comprising one or more PUFA synthase domains such as a DH domain (such as SEQ ID NO:38 or SEQ ID NO:40), an ER domain (SEQ ID NO:42), and combinations thereof. In some embodiments, the polypeptide comprises one or more amino acid sequences within PFA3 (SEQ ID NO:6) comprising one or more PUFA synthase domains, including one or more copies of any individual domain in combination with one or more copies of any other individual domain.

In some embodiments, the present invention is directed to a nucleic acid molecule comprising a polynucleotide sequence encoding a polypeptide, wherein the polypeptide comprises an amino acid sequence at least 80% identical to SEQ ID NO:2, and wherein the polypeptide comprises a PUFA synthase activity selected from the group consisting of KS activity, MAT activity, ACP activity, KR activity, DH activity, and combinations thereof.

In some embodiments, the present invention is directed to nucleic acid molecules comprising a polynucleotide sequence encoding a polypeptide, wherein the polypeptide comprises an amino acid sequence at least 80% identical to SEQ ID NO:4, and wherein the polypeptide comprises a PUFA synthase activity selected from the group consisting of KS activity, CLF activity, AT activity, ER activity, and combinations thereof.

In some embodiments, the present invention is directed to nucleic acid molecules comprising a polynucleotide sequence encoding a polypeptide, wherein the polypeptide comprises an amino acid sequence at least 80% identical to SEQ ID NO:6, and wherein the polypeptide comprises a PUFA synthase activity selected from the group consisting of DH activity, ER activity, and combinations thereof.

In some embodiments, the nucleic acid molecules comprise polynucleotide sequences at least about 80%, 85%, or 90% identical to the polynucleotide sequences reported herein, or at least about 95%, 96%, 97%, 98%, 99%, or 100% identical to the polynucleotide sequences reported herein. The term "percent identity," as known in the art, is a relationship between two or more amino acid sequences or two or more polynucleotide sequences, as determined by comparing the sequences. In the art, "identity" also means the degree of sequence relatedness between amino acid or polynucleotide sequences, as the case may be, as determined by the match between strings of such sequences.

By a nucleic acid molecule having a polynucleotide sequence at least, for example, 95% "identical" to a reference polynucleotide sequence of the present invention, it is intended that the polynucleotide sequence of the nucleic acid molecule is identical to the reference sequence except that the polynucleotide sequence can include up to five nucleotide differences per each 100 nucleotides of the reference polynucleotide sequence. In other words, to obtain a nucleic acid molecule having a polynucleotide sequence at least 95% identical to a reference polynucleotide sequence, up to 5% of the nucleotides in the reference sequence can be deleted or substituted with another nucleotide, or a number of nucleotides up to 5% of the total nucleotides in the reference sequence can be inserted into the reference sequence.

As a practical matter, whether any particular polynucleotide sequence or amino acid sequence is at least 80%, 85%, 90%, 95%, 96%, 97%, 98% or 99% identical to a polynucleotide sequence or amino acid sequence of the present invention can be determined conventionally using known computer programs. A method for determining the best overall match between a query sequence (a sequence of the present invention) and a subject sequence can be determined using the alignment of sequences and calculation of identity scores. The alignments were done using the computer program AlignX, which is a component of the Vector NTI Suite 10.0 package from Invitrogen (www.invitrogen.com). The alignments were performed using a ClustalW alignment (Thompson, J. D., et al. Nucl. Acids Res. 22: 4673-4680 (1994)) for both amino acid and polynucleotide sequence alignments. The default scoring matrices Blosum62mt2 and swgapdnamt were used for amino acid and polynucleotide sequence alignments, respectively. For amino acid sequences, the default gap opening penalty is 10 and the gap extension penalty 0.1. For polynucleotide sequences, the default gap opening penalty is 15 and the gap extension penalty is 6.66.

The present invention is directed to an isolated nucleic acid molecule comprising a polynucleotide sequence encoding a polypeptide comprising PUFA synthase activity selected from the group consisting of KS activity, MAT activity, ACP activity, KR activity, CLF activity, AT activity, ER activity, DH activity, and combinations thereof, wherein the polynucleotide hybridizes under stringent conditions to the complement of any of the polynucleotide sequences described above.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified. See, e.g., Sambrook J. and Russell D. 2001. Molecular cloning: A laboratory manual, 3rd edition. Cold Spring Harbor Laboratory Press, Cold Spring Harbor, New York. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

The present invention is directed to an isolated nucleic acid molecule comprising a polynucleotide sequence that is fully complementary to any of the polynucleotide sequences described above. The term "complementary" is used to describe the relationship between nucleotide bases that are capable to hybridizing to one another. For example, with respect to DNA, adenosine is complementary to thymine and cytosine is complementary to guanine.

In certain embodiments, the polynucleotide or nucleic acid is DNA. In the case of DNA, a nucleic acid molecule comprising a polynucleotide sequence which encodes a polypeptide can normally include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a polynucleotide sequence encoding a polypeptide if the promoter was capable of effecting transcription of that polynucleotide sequence. The promoter can be a cell-specific promoter that directs substantial transcription of the DNA only in predetermined cells. In general, a coding region is located 3' to a promoter. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease Si), as well as protein binding domains (consensus sequences) responsible for the binding of RNA polymerase.

Suitable regulatory regions include nucleic acid regions located upstream (5' non-coding sequences), within, or downstream (3' non-coding sequences) of a coding region, and which influence the transcription, RNA processing or stability, or translation of the associated coding region. Regulatory regions can include promoters, translation leader sequences, RNA processing sites, effector binding sites, and stem-loop structures. Other transcription control elements, besides a promoter, for example enhancers, operators, repressors, and transcription termination signals, can be operably associated with the polynucleotide to direct cell-specific transcription. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

In certain aspects of the invention, polynucleotide sequences having at least 20 bases, at least 30 bases, or at least 50 bases and that hybridize to a polynucleotide sequence of the present invention can be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally, two short segments of the instant sequences can be used in polymerase chain reaction (PCR) protocols to amplify longer nucleic acid fragments encoding homologous genes from DNA or RNA. The polymerase chain reaction can also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence can be based upon sequences derived from the cloning vector.

In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Therefore, the nucleic acid molecules of the present invention can be used to isolate genes encoding homologous proteins from the same or other species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683,202; ligase chain reaction (LCR) (Tabor, S. et al., *Proc. Acad. Sci. USA* 82: 1074 (1985)); or strand displacement amplification (SDA; Walker, et al., *Proc. Natl. Acad. Sci. U.S.A.* 89: 392 (1992)).

In some embodiments, the isolated nucleic acid molecules of the present invention are used to isolate homologous nucleic acid molecules from other organisms in order to identify PUFA synthases that produce similar or improved PUFA profiles. In some embodiments, the isolated nucleic acid molecules of the present invention are used to isolate homologous nucleic acid molecules from other organisms that are involved in producing high amounts of DHA and/or EPA.

The nucleic acid molecules of the present invention also comprise polynucleotide sequences encoding a PUFA synthase, a domain of a PUFA synthase, or a fragment of the PUFA synthase fused in frame to a marker sequence which allows for detection of the polypeptide of the present invention. Marker sequences include auxotrophic or dominant markers known to one of ordinary skill in the art such as ZEO (zeocin), NEO (G418), hygromycin, arsenite, HPH, NAT, and the like.

The present invention also encompasses variants of the PUFA synthase gene. Variants can contain alterations in the coding regions, non-coding regions, or both. Examples are polynucleotide sequence variants containing alterations which produce silent substitutions, additions, or deletions, but do not alter the properties or activities of the encoded polypeptide. In certain embodiments, polynucleotide sequence variants are produced by silent substitutions due to the degeneracy of the genetic code. In further embodiments, polynucleotide sequence variants can be produced for a variety of reasons, e.g., to optimize codon expression for a particular host (e.g., changing codons in the thraustochytrid mRNA to those preferred by other organisms such as *E. coli* or *Saccharomyces cerevisiae*).

Also provided in the present invention are allelic variants, orthologs, and/or species homologs. Procedures known in the art can be used to obtain full-length genes, allelic variants, splice variants, full-length coding portions, orthologs, and/or species homologs of the genes described herein using information from the sequences disclosed herein. For example, allelic variants and/or species homologs can be isolated and identified by making suitable probes or primers from the sequences provided herein and screening a suitable nucleic acid source for allelic variants and/or the desired homologue.

Vectors

The present invention is directed to a recombinant nucleic acid molecule comprising any of the nucleic acid molecules described above or combinations thereof and a transcription control sequence. In some embodiments, the recombinant nucleic acid molecule is a recombinant vector.

The present invention is directed to a method for making a recombinant vector comprising inserting one or more isolated nucleic acid molecules as described herein into a vector.

The vectors of this invention can be, for example, a cloning vector or an expression vector. The vector can be, for example, in the form of a plasmid, a viral particle, a phage, etc.

The polynucleotide sequences of the invention can be included in any one of a variety of expression vectors for expressing a polypeptide. Such vectors include chromosomal, nonchromosomal, and synthetic DNA or RNA sequences, e.g., derivatives of SV40; bacterial plasmids; and yeast plasmids. However, any other appropriate vector known to one of ordinary skill in the art can be used.

The appropriate DNA sequence can be inserted into the vector by a variety of procedures. For example, the DNA sequence is inserted by traditional cloning methods (restriction enzyme cloning) or more modern molecular engineering techniques such as PCR cloning, seamless cloning, etc. Such procedures and others are deemed to be within the scope of those skilled in the art.

The present invention also includes recombinant constructs comprising one or more of the polynucleotide sequences described above. The constructs comprise a vector, such as a plasmid or viral vector, into which one or more sequences of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available.

Some embodiments include a recombinant vector (e.g., a plasmid) comprising one or more heterologous polynucleotides encoding a component of a PUFA synthase system. A recombinant vector is an engineered (e.g., artificially produced) nucleic acid molecule that is used as a tool for manipulating a nucleic acid sequence of choice, and/or for introducing such a nucleic acid sequence into a host cell. The recombinant vector may therefore be suitable for use in cloning, sequencing, and/or otherwise manipulating a polynucleotide therein, such as by expressing and/or delivering the polynucleotide into a host cell to form a recombinant cell. A vector may contain nucleotide sequences that are not naturally found adjacent to the polynucleotide to be cloned or delivered. A vector may also contain regulatory nucleic acid sequences (e.g., promoters, untranslated regions) that are naturally found adjacent to the polynucleotide or that are useful for expression of the polynucleotide. An integrated polynucleotide may be under chromosomal promoter control, under native or plasmid promoter control, or under a combination of several promoter controls. A vector may be either RNA or DNA, and may be either prokaryotic or eukaryotic. A vector may be maintained as an extrachromosomal element (e.g., a plasmid) or it may be integrated into a chromosome of a recombinant organism (e.g., a microbe, and plant cell). The entire vector may remain in place within a host cell, or under certain conditions, extraneous DNA (e.g., unnecessary plasmid sequences) may be deleted, leaving behind one or more heterologous polynucleotides encoding a component of a PUFA synthase system. Single or multiple copies of the heterologous polynucleotides may be integrated into the host genome. A recombinant vector of the present invention may contain at least one selectable marker.

In one embodiment, a recombinant vector used in the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., one or more PUFA synthases) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector that enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete, inactivate, or replace an endogenous gene or portion of a gene within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to associate with the target gene such that the target gene and the insert may undergo homologous recombination, whereby the endogenous target gene is deleted, inactivated, attenuated (i.e., by at least a portion of the endogenous target gene being mutated or deleted), or replaced. The use of this type of recombinant vector to replace an endogenous Schizochytrium gene, for example, with a recombinant gene is described in the Examples section, and the general technique for genetic transformation of Thraustochytrids is described in detail in U.S. Patent Application Publication No. 20030166207, published Sep. 4, 2003. Genetic transformation techniques for microalgae are well-known in the art. It is an embodiment of the present invention that the PUFA synthase genes described herein can be used to transform plants or microorganisms such as Thraustochytrids to improve and/or alter (modify, change) the PUFA synthase production capabilities of such plants or microorganisms.

Host Cells

The present invention is directed to a host cell that expresses any of the nucleic acid molecules and recombinant nucleic acid molecules described above as well as combinations thereof.

The term "expression" as used herein refers to a process by which a gene produces a biochemical, for example, a RNA or polypeptide. The process includes any manifestation of the functional presence of the gene within the cell including, without limitation, gene knockdown as well as both transient expression and stable expression. It includes, without limitation, transcription of the gene into messenger RNA (mRNA), transfer RNA (tRNA), small hairpin RNA (shRNA), small interfering RNA (siRNA), or any other RNA product, and the translation of such mRNA into polypeptide(s). If the final desired product is biochemical, expression includes the creation of that biochemical and any precursors.

To produce one or more desired polyunsaturated fatty acids, a host cell can be genetically modified to introduce one or more PUFA synthases, or their subunits, as disclosed herein into the host cell.

When genetically modifying organisms to express a PUFA synthase system according to the present invention, some host organisms can endogenously express accessory proteins that are required in conjunction with a PUFA synthase system in order to produce PUFAs. However, it may be necessary to transform some organisms with nucleic acid molecules encoding one or more accessory protein(s) in order to enable or to enhance production of PUFAs by the organism, even if the organism endogenously produces a homologous accessory protein. Some heterologous accessory proteins can operate more effectively or efficiently with the transformed PUFA synthase proteins than the host cells' endogenous accessory protein(s).

Accessory proteins are defined herein as proteins that are not considered to be part of the core PUFA synthase system (i.e., not part of the PUFA synthase enzyme complex itself) but which may be necessary for PUFA production or efficient PUFA production using the core PUFA synthase enzyme complex of the present invention. For example, in order to produce PUFAs, a PUFA synthase system must work with an accessory protein that transfers a 4'-phosphopantetheinyl moiety from coenzyme A to the acyl carrier protein (ACP) domain(s). Therefore, a PUFA synthase system can be considered to include at least one 4'-phosphopantetheinyl transferase (PPTase) domain, or such a domain can be considered to be an accessory domain or protein to the PUFA synthase system. Structural and functional characteristics of PPTases have been described in detail, e.g., in U.S. Appl. Publ. Nos. 2002/0194641; 2004/0235127; and 2005/0100995.

A domain or protein having 4'-phosphopantetheinyl transferase (PPTase) biological activity (function) is characterized as the enzyme that transfers a 4'-phosphopantetheinyl moiety from Coenzyme A to the acyl carrier protein (ACP). This transfer to an invariant serine reside of the ACP activates the inactive apo-form to the holo-form. In both polyketide and fatty acid synthesis, the phosphopantetheine group forms thioesters with the growing acyl chains. The PPTases are a family of enzymes that have been well characterized in fatty acid synthesis, polyketide synthesis, and non-ribosomal peptide synthesis. The sequences of many PPTases are known, crystal structures have been determined (e.g., Reuter K., et al., *EMBO J.* 18(23):6823-31 (1999)), and mutational analysis has identified amino acid residues important for activity (Mofid M. R., et al., *Biochemistry* 43(14):4128-36 (2004)).

One heterologous PPTase which has been previously demonstrated to recognize *Schizochytrium* PUFA synthase ACP domains as substrates is the Het I protein of *Nostoc* sp. PCC 7120 (formerly called *Anabaena* sp. PCC 7120). Het I is present in a cluster of genes in *Nostoc* known to be responsible for the synthesis of long chain hydroxy-fatty acids that are a component of a glyco-lipid layer present in heterocysts of that organism (Black and Wolk, *J. Bacteriol.* 176: 2282-2292 (1994); Campbell et al., *Arch. Microbiol.* 167: 251-258 (1997)). Het I is likely to activate the ACP domains of a protein, Hgl E, present in that cluster. Sequences and constructs containing Het I have been described in, e.g., U.S. Appl. Publ. No. 2007/0244192, incorporated by reference herein in its entirety.

Another heterologous PPTase which has been demonstrated previously to recognize the *Schizochytrium* PUFA synthase ACP domains is Sfp, derived from *Bacillus subtilis*. Sfp has been well characterized and is widely used due to its ability to recognize a broad range of substrates. Based on published sequence information (Nakana, et al., *Molecular and General Genetics* 232: 313-321 (1992)), an expression vector was previously produced for Sfp by cloning the coding region, along with defined up- and downstream flanking DNA sequences, into a pACYC-184 cloning vector. This construct encodes a functional PPTase as demonstrated by its ability to be co-expressed with the *Schizochytrium* PUFA synthase in *E. coli* which, under appropriate conditions, resulted in the accumulation of DHA in those cells (See U.S. Appl. Publ. No. 2004/0235127, incorporated by reference herein in its entirety).

Host cells can include microbial cells; animal cells; plant cells; and insect cells. Representative examples of appropriate hosts include bacterial cells; thermophilic or mesophilic bacteria; marine bacteria; thraustochytrids; fungal cells, such as yeast; plant cells; insect cells; and isolated animal cells. Host cells can be either untransfected cells or cells that are already transfected with at least one other recombinant nucleic acid molecule. Host cells can also include transgenic cells that have been engineered to express a PUFA synthase. The selection of an appropriate host is deemed to be within the scope of those skilled in the art from the teachings herein.

Host cells include any microorganism of the class of Labyrinthulomycetes, such as microorganisms from the order Thraustochytriales. In this application, the terms "Thraustochytriales" and "Thraustochytrids" are used interchangeably. In some embodiments, the host cell is any microorganism from the family Thraustochytriaceae. Host cells of the invention may be any microorganism from a genus including, but not limited to, Thraustochytrium, *Labyrinthuloides, Japonochytrium*, and Schizochytrium. Species within these genera include, but are not limited to: any Schizochytrium species, including *Schizochytrium aggregatum, Schizochytrium limacinum, Schizochytrium minutum*; any Thraustochytrium species (including former *Ulkenia* species such as *U. visurgensis, U. amoeboida, U. sarkariana, U. profunda, U. radiata*, U. minuta and *Ulkenia* sp. BP-5601), and including *Thraustochytrium striatum, Thraustochytrium aureum, Thraustochytrium roseum*; and any *Japonochytrium* species. Strains of Thraustochytriales include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); Schizochytrium *aggregatum* (Goldstein et Belsky) (ATCC 28209); *Schizochytrium limacinum* (Honda et Yokochi) (IFO 32693); Thraustochytrium sp. (23B) (ATCC 20891); *Thraustochytrium striatum* (Schneider) (ATCC 24473); *Thraustochytrium aureum* (Goldstein) (ATCC 34304); *Thraustochytrium roseum* (Goldstein) (ATCC 28210); and *Japonochytrium* sp. (L1) (ATCC 28207). Other examples of suitable host microorganisms for genetic modification include, but are not limited to, yeast including *Saccharomyces cerevisiae, Saccharomyces carls-*

*bergensis*, or other yeast such as *Candida, Kluyveromyces*, or other fungi, for example, filamentous fungi such as *Aspergillus, Neurospora, Penicillium*, etc. Bacterial cells also can be used as hosts. This includes *Escherichia coli*, which can be useful in fermentation processes. Alternatively, a host such as a *Lactobacillus* species or *Bacillus* species can be used as a host.

Plant host cells include, but are not limited to, any higher plants, including both dicotyledonous and monocotyledonous plants, and consumable plants, including crop plants and plants used for their oils. Such plants can include, for example: canola, oilseed, soybeans, rapeseed, linseed, corn, safflowers, sunflowers, peanut, and tobacco. Other plants include those plants that are known to produce compounds used as pharmaceutical agents, flavoring agents, nutraceutical agents, functional food ingredients, cosmetically active agents, or plants that are genetically engineered to produce these compounds/agents. Thus, any plant species or plant cell can be selected. Examples of plants and plant cells, and plants grown or derived therefrom, include, but are not limited to, plants and plant cells obtainable from canola (*Brassica rapa* L.); canola cultivars NQC02CNX12 (ATCC PTA-6011), NQC02CNX21 (ATCC PTA-6644), and NQC02CNX25 (ATCC PTA-6012) as well as cultivars, breeding cultivars, and plant parts derived from canola cultivars NQC02CNX12, NQC02CNX21, and NQC02CNX25 (See U.S. Pat. Nos. 7,355,100, 7,456,340, and 7,348,473, respectively); a plant of the family Fabaceae; a plant of the genus Glycine; common bean (*Phaseolus vulgaris*); broad bean (*Viciafaba*); common pea (*Pisum sativum*); soybean (*Glycine max*); rapeseed (*Brassica* spp.); linseed/flax (*Linum usitatissimum*); maize (corn) (*Zea mays*); safflower (Carthamus tinctorius); sunflower (*Helianthus annuus*); tobacco (*Nicotiana tabacum*); *Arabidopsis thaliana*, Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); mustard (*Brassica* spp. and *Sinapis alba*); oil palm (*Elaeis guineeis*); olive (*Olea eurpaea*); rice (*Oryza sativa*); squash (*Cucurbita maxima*); barley (*Hordeum vulgare*); wheat (*Traeticum aestivum*); and duckweed (*Lemnaceae* sp.). Plant lines from these and other plants can be produced, selected, or optimized for a desirable trait such as or associated with, but not limited to, seed yield, lodging resistance, emergence, disease resistance or tolerance, maturity, late season plant intactness, plant height, shattering resistance, ease of plant transformation, oil content, or oil profile. Plant lines can be selected through plant breeding such as pedigree breeding, recurrent selection breeding, intercross and backcross breeding, as well as methods such as marker assisted breeding and tilling. See, e.g., U.S. Pat. No. 7,348,473.

Animal cells include any isolated animal cells.

The present invention is directed to a host cell that expresses one or more nucleic acid molecules or recombinant nucleic acid molecules, including vectors, of the invention.

The present invention is directed to a method for making a recombinant host cell comprising introducing a recombinant vector into a host cell.

Host cells can be genetically engineered (transduced or transformed or transfected) with the vectors of this invention that can be, for example, a cloning vector or an expression vector. The vector can be, for example, in the form of a plasmid, a viral particle, a phage, etc. The vector containing a polynucleotide sequence as described herein, as well as an appropriate promoter or control sequence, can be employed to transform an appropriate host to permit expression of the polypeptide encoded by the polynucleotide sequence. The genetic modification of host cells can also include the optimization of genes for preferred or optimal host codon usage.

The engineered host cells can be cultured in conventional nutrient media modified as appropriate for activating promoters, selecting transformants, or amplifying the genes of the present invention. The culture conditions, such as temperature, pH, and the like, are those previously used with the host cell selected for expression, and will be apparent to the ordinarily skilled artisan.

In some embodiments, the host cell is a Thraustochytrid in which the native PUFA synthase system has been deleted. The present inventors have created knockouts of PFA1, PFA2, and PFA3 in Schizochytrium (See U.S. Pat. No. 7,217,856; referred to therein as OrfA, OrfB, and OrfC). The knockout strategy relies on the homologous recombination that has been demonstrated to occur in Schizochytrium (See U.S. Pat. No. 7,001,772). Several strategies can be employed in the design of knockout constructs. The specific strategy used to inactivate these three genes utilized insertion of a Zeocin™ resistance gene coupled to a tubulin promoter (derived from pMON50000, See U.S. Pat. No. 7,001,772) into a cloned portion of the Orf. The new construct containing the interrupted coding region was then used for the transformation of wild-type Schizochytrium cells via particle bombardment (See U.S. Pat. No. 7,001,772). Bombarded cells were spread on plates containing both Zeocin™ and a supply of PUFAs. Colonies that grew on these plates were then streaked onto Zeocin™ plates that were not supplemented with PUFAs. Those colonies that required PUFA supplementation for growth were candidates for having had the PUFA synthase Orf inactivated via homologous recombination. In all three cases, this presumption was confirmed by rescuing the knockout by transforming the cells with a full-length genomic DNA clone of the respective Schizochytrium PFA synthase genes. Furthermore, in some cases, it was found that in the rescued transformants the Zeocin™ resistance gene had been removed (See U.S. Pat. No. 7,217,856), indicating that the introduced functional gene had integrated into the original site by double homologous recombination (i.e., deleting the resistance marker). One key to the success of this strategy was supplementation of the growth medium with PUFAs. An effective means of supplementation was found to be sequestration of the PUFAs by mixing with partially methylated beta-cyclodextrin prior to adding to the growth medium (See U.S. Pat. No. 7,217,856). Together, these experiments demonstrate the principle that one of skill in the art, given the guidance provided herein, can inactivate one or more of the PUFA synthase genes in a PUFA synthase-containing microorganism such as Schizochytrium, and create a PUFA auxotroph which can then be used for further genetic modification (e.g., by introducing other PUFA synthase genes) according to the present invention (e.g., to alter the fatty acid profile of the recombinant organism).

One element of the genetic modification of the organisms of the present invention is the ability to directly transform a Thraustochytrid genome. In U.S. Pat. No. 7,001,772, supra, transformation of *Schizochytrium* via single crossover homologous recombination and targeted gene replacement via double crossover homologous recombination were demonstrated. As discussed above, the present inventors have used this technique for homologous recombination to inactivate PFA1, PFA2 and PFA3 of the PUFA synthase system in *Schizochytrium* (See U.S. Pat. No. 7,217,856). The resulting mutants are dependent on supplementation of the media with PUFAs. Several markers of transformation, promoter elements for high level expression of introduced genes and methods for delivery of exogenous genetic material have been developed and are available. Therefore, the tools are in place for knocking out endogenous PUFA synthase genes in Thraustochytrids and other eukaryotes having similar PUFA synthase systems and replacing them with genes from other organisms, such as the genes from *Schizochytrium* sp. ATCC PTA-9695 as shown herein.

Methods for Making a Recombinant Host Cell

The present invention is directed to a method for making a recombinant host cell comprising introducing a recombinant vector into a host cell.

Host cells can be genetically engineered (transduced or transformed or transfected) with the vectors of this invention that can be, for example, a cloning vector or an expression vector. The vector can be, for example, in the form of a plasmid, a viral particle, a phage, etc. The vector containing a polynucleotide sequence as described herein, as well as an appropriate promoter or control sequence, can be employed to transform an appropriate host to permit expression of the polypeptide encoded by the polynucleotide sequence. The genetic modification of host cells can also include the optimization of genes for preferred or optimal host codon usage.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast, or into plant cells. In microbial and plant systems, the term "transformation" is used to describe an inherited change due to the acquisition of exogenous nucleic acids by the microorganism or plant and is essentially synonymous with the term "transfection." However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass transfection of animal cells, and transformation of microbial cells or plant cells, to the extent that the terms pertain to the introduction of exogenous nucleic acids into a cell. Therefore, transfection techniques include, but are not limited to, transformation, particle bombardment, diffusion, active transport, bath sonication, electroporation, microinjection, lipofection, adsorption, infection and protoplast fusion.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

The engineered host cells can be cultured in conventional nutrient media modified as appropriate for activating promoters, selecting transformants, or amplifying the genes of the present invention. The culture conditions, such as temperature, pH, and the like, are those previously used with the host cell selected for expression, and will be apparent to the ordinarily skilled artisan.

According to the present invention, a genetically modified microorganism or plant includes a microorganism or plant that has been modified using recombinant technology or by classical mutagenesis and screening techniques. As used herein, genetic modifications that result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications that result in an increase in gene expression or function can be referred to as amplification, overproduction, overexpression, activation, enhancement, addition, or up-regulation of a gene.

The genetic modification of a microorganism or plant according to the present invention preferably affects the activity of the PUFA synthase system expressed by the microorganism or plant, whether the PUFA synthase system is endogenous and genetically modified, endogenous with the introduction of recombinant nucleic acid molecules into the organism (with the option of modifying the endogenous system or not), or provided completely by recombinant technology. To alter the PUFA production profile of a PUFA synthase system or organism expressing such system includes causing any detectable or measurable change in the production of any one or more PUFAs (or other bioactive molecule produced by the PUFA synthase system) by the host microorganism or plant as compared to in the absence of the genetic modification (i.e., as compared to the unmodified, wild-type microorganism or plant or the microorganism or plant that is unmodified at least with respect to PUFA synthesis, i.e., the organism might have other modifications not related to PUFA synthesis). To affect the activity of a PUFA synthase system includes any genetic modification that causes any detectable or measurable change or modification in the PUFA synthase system expressed by the organism as compared to in the absence of the genetic modification. A detectable change or modification in the PUFA synthase system can include, but is not limited to: a change or modification (introduction of, increase or decrease) of the expression and/or biological activity of any one or more of the domains in a modified PUFA synthase system as compared to the endogenous PUFA synthase system in the absence of genetic modification; the introduction of PUFA synthase system activity (i.e., the organism did not contain a PUFA synthase system prior to the genetic modification) into an organism such that the organism now has measurable/detectable PUFA synthase system activity, such as production of a product of a PUFA synthase system; the introduction into the organism of a functional domain from a different PUFA synthase system than the PUFA synthase system endogenously expressed by the organism such that the PUFA synthase system activity is modified (e.g., a PUFA synthase domain or protein is introduced into an organism that endogenously expresses a PUFA synthase system, such as a Thraustochytrid); a change in the amount of a bioactive molecule (e.g., a PUFA) produced by the PUFA synthase system (e.g., the system produces more (increased amount) or less (decreased amount) of a given product as compared to in the absence of the genetic modification); a change in the type of a bioactive molecule (e.g., a change in the type of PUFA) produced by the PUFA synthase system (e.g., the system produces an additional or different PUFA, a new or different product, or a variant of a PUFA or other product that is naturally produced by the system); and/or a change in the ratio of multiple bioactive molecules produced by the PUFA synthase system (e.g., the system produces a different ratio of one PUFA to another PUFA, produces a completely different lipid profile as compared to in the absence of the genetic modification, or places various PUFAs in different positions in a triacylglycerol as compared to the natural configuration). Such a genetic modification includes any type of genetic modification and specifically includes modifications made by recombinant technology and/or by classical mutagenesis.

It should be noted that reference to increasing the activity of a functional domain or protein in a PUFA synthase system refers to any genetic modification in the organism containing the domain or protein (or into which the domain or protein is to be introduced) which results in increased functionality of the domain or protein system and can include higher activity of the domain or protein (e.g., specific activity or in vivo enzymatic activity), reduced inhibition or degradation of the domain or protein system, and overexpression of the domain or protein. For example, gene copy number can be increased, expression levels can be increased by use of a promoter that gives higher levels of expression than that of the native promoter, or a gene can be altered by genetic engineering or classical mutagenesis to increase the activity of the domain or protein encoded by the gene.

Similarly, reference to decreasing the activity of a functional domain or protein in a PUFA synthase system refers to any genetic modification in the organism containing such domain or protein (or into which the domain or protein is to be introduced) which results in decreased functionality of the domain or protein and includes decreased activity of the domain or protein, increased inhibition or degradation of the domain or protein and a reduction or elimination of expression of the domain or protein. For example, the action of domain or protein of the present invention can be decreased by blocking or reducing the production of the domain or protein, "knocking out" the gene or portion thereof encoding the domain or protein, reducing domain or protein activity, or inhibiting the activity of the domain or protein. Blocking or reducing the production of a domain or protein can include placing the gene encoding the domain or protein under the control of a promoter that requires the presence of an inducing compound in the growth medium. By establishing conditions such that the inducer becomes depleted from the medium, the expression of the gene encoding the domain or protein (and therefore, of protein synthesis) could be turned off. The present inventors have demonstrated the ability to delete (knock out) targeted genes in a Thraustochytrid microorganism in U.S. Pat. No. 7,217,856. Blocking or reducing the activity of domain or protein could also include using an excision technology approach similar to that described in U.S. Pat. No. 4,743,546, incorporated herein by reference. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In a specific embodiment of the invention, the endogenous Thraustochytrid PUFA synthase genes, such as the Schizochytrium genes encoding PUFA synthase enzymes that normally produce DHA and DPA n-6, are modified by random or targeted mutagenesis, replaced with genes from other organisms that encode homologous PUFA synthase proteins (e.g., from bacteria or other sources) and/or replaced with genetically modified Schizochytrium, Thraustochytrium or other Thraustochytrid PUFA synthase genes. As discussed herein, combinations of nucleic acid molecules encoding one or more PUFA synthases genes from Schizochytrium sp. ATCC PTA-9695 will result in production of a desired PUFA or other bioactive molecule. The product of the enzymes encoded by these introduced and/or modified genes can be EPA, for example, or it could be some other related molecule, including other PUFAs. One feature of this method is the utilization of endogenous components of Thraustochytrid PUFA synthesis and accumulation machinery that is essential for efficient production and incorporation of the PUFA into phospholipids (PL) and triacylglycerols (TAG), while taking further advantage of the ability of PUFA synthases from Schizochytrium sp. ATCC PTA-9695, for example, to produce EPA. In particular, this embodiment of the invention is directed to the modification of the type of PUFA produced by the organism, while retaining the high oil productivity of the parent strain.

Although some of the following discussion uses the organism Schizochytrium as an exemplary host organism, any Thraustochytrid can be modified according to the present invention, including members of the genera Thraustochytrium, Labyrinthuloides, and Japonochytrium. Furthermore, using methods for screening organisms as set forth in U.S. Pat. No. 7,247,461, one can identify other organisms useful in the present method and all such organisms are encompassed herein. Moreover, PUFA synthase systems can be constructed using the exemplary information provided herein, produced in other microorganisms, such as bacteria or yeast, and transformed into plants cells to produce genetically modified plants. The concepts discussed herein can be applied to various systems as desired.

General discussion above with regard to recombinant nucleic acid molecules and transfection of host cells is intended to be applied to any recombinant nucleic acid molecule discussed herein, including those encoding any amino acid sequence having a biological activity of at least one domain from a PUFA synthase system, those encoding amino acid sequences from other PUFA synthase systems, and those encoding other proteins or domains.

Cultures and Isolated Biomasses

The invention is directed to a culture comprising one or more isolated recombinant host cells of the invention. Various fermentation parameters for inoculating, growing, and recovering microflora, such as microalgae and thraustochytrids, are known in the art. See, e.g., U.S. Pat. No. 5,130,242, incorporated by reference herein in its entirety. Liquid or solid media can contain natural or artificial sea water. Carbon sources for heterotrophic growth include, but are not limited to, glucose, fructose, xylose, saccharose, maltose, soluble starch, molasses, fucose, glucosamine, dextran, fats, oils, glycerol, sodium acetate, and mannitol. Nitrogen sources include, but are not limited to, peptone, yeast extract, polypeptone, malt extract, meat extract, casamino acid, corn steep liquor, organic nitrogen sources, sodium glutamate, urea, inorganic nitrogen sources, ammonium acetate, ammonium sulfate, ammonium chloride, and ammonium nitrate.

The invention is directed to an isolated biomass of a recombinant host cell of the invention. An isolated biomass of the invention is a harvested cellular biomass obtained by any conventional method for the isolation of a biomass, such as described in U.S. Pat. No. 5,130,242 and U.S. Appl. Publ. No. 2002/0001833, each of which are incorporated by reference herein in its entirety. In some embodiments, the dry cell weight of the biomass isolated from each liter of culture is at least about 10 g, at least about 15 g, at least about 20 g, at least about 25 g, at least about 30 g, at least about 50 g, at least about 60 g, at least about 70 g, at least about 80 g, at least about 100 g, at least about 120 g, at least about 140 g, at least about 160 g, at least about 180 g, or at least about 200 g after growing for about 6 days to about 8 days at about 15° C. to about 30° C. in a culture medium of about pH 6.5 to about 9.5 comprising sources of carbon, nitrogen, and nutrients, and about 950 ppm to about 8500 ppm chloride ions. In some embodiments, the dry cell weight of the biomass isolated from each liter of culture is at least about 10 g, at least about 15 g, at least about 20 g, at least about 25 g, at least about 30 g, at least about 50 g, at least about 60 g, at least about 70 g, at least about 80 g, at least about 100 g, at least about 120 g, at least about 140 g, at least about 160 g, at least about 180 g, or at least about 200 g after growing for about 6 days, about 7 days, or about 8 days at about 15° C., about 16° C., about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, about pH 8.5, about pH 9, or about pH 9.5 comprising sources of carbon, nitrogen, and nutrients, and about 950 ppm to about 8500 ppm chloride ions. In some embodiments, the dry cell weight of the biomass isolated from each liter of culture is about 10 g to about 200 g after growing for about 6 days to about 8 days at about 15° C. to about 30° C. in a culture medium of about pH 6.5 to about pH 9.5 comprising sources of carbon, nitrogen, and nutrients, and about 950 ppm to about 8500 ppm chloride ions. In some embodiments, the dry cell weight of the biomass isolated from each liter of culture is about 10 g to about 200 g, about 10 g to about 100 g, about 10 g to about 50 g, about 15 g to about 200 g, about 15 g to about 100 g, about 15 g to about 50 g, about 20 g to about 200 g, about 20 g to about 100 g, about 20 g to about 50 g, about 50 g to about 200 g, or about 50 g to about 100 g after growing for about 6 days, about 7 days, or about 8 days at about 15° C., about 16° C., about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, about pH 8.5, about pH 9, or about pH 9.5 comprising sources of carbon, nitrogen, and nutrients, and about 950 ppm to about 8500 ppm chloride ions. In some embodiments, the isolated culture does not contain polyvinylpyrrolidone.

In some embodiments, the isolated culture has an omega-3 fatty acid productivity of at least about 0.2 g/L/day, at least about 0.3 g/L/day, at least about 0.4 g/L/day, at least about 0.5 g/L/day, at least about 1 g/L/day, at least about 1.2 g/L/day, at least about 1.5 g/L/day, at least about 1.7 g/L/day, at least about 2 g/L/day, at least about 3 g/L/day, at least about 3.5 g/L/day, at least about 4 g/L/day, at least about 4.5 g/L/day, at least about 5 g/L/day, at least about 6 g/L/day, or at least about 8 g/L/day after growing for about 6 days, about 7 days, or about 8 days at about 15° C. to about 30° C. in a culture medium of about pH 6.5 to about pH 8.5 or about pH 6.5 to about pH 9.5 comprising sources of carbon, nitrogen, and nutrients, and about 950 ppm to about 8500 ppm chloride ions. In some embodiments, the isolated culture has an omega-3 fatty acid productivity of about 0.2 g/L/day to about 20 g/L/day, about 0.4 g/L/day to about 20 g/L/day, about 0.4 g/L/day to about 2 g/L/day, about 1 g/L/day to about 2 g/L/day, about 1 g/L/day to about 20 g/L/day, about 2 g/L/day to about 15 g/L/day, about 2 g/L/day to about 10 g/L/day, about 3 g/L/day to about 10 g/L/day, about 4 g/L/day to about 9 g/L/day, about 4 g/L/day to about 8 g/L/day, about 4 g/L/day to about 7 g/L/day, or about 4 g/L/day to about 6 g/L/day after growing for about 6 days, about 7 days, or about 8 days at about 15° C. to about 30° C. in a culture medium of about pH 6.5 to about pH 9.5 comprising sources of carbon, nitrogen, and nutrients, and about 950 ppm to about 8500 ppm chloride ions.

In some embodiments, the isolated culture comprises an EPA productivity of at least about 0.2 g/L/day, at least about 0.3 g/L/day, at least about 0.4 g/L/day, at least about 0.5 g/L/day, at least about 0.6 g/L/day, at least about 0.7 g/L/day, at least about 0.8 g/L/day, at least about 0.9 g/L/day, at least about 1 g/L/day, at least about 1.2 g/L/day, at least about 1.5 g/L/day, at least about 1.7 g/L/day, at least about 2 g/L/day, at least about 3 g/L/day, at least about 4 g/L/day, or at least about 5 g/L/day after growing for about 6 days, about 7 days, or about 8 days at about 15° C. to about 30° C. in a culture medium of about pH 6.5 to about pH 8.5 or about pH 6.5 to about pH 9.5 comprising sources of carbon, nitrogen, and nutrients, and about 950 ppm to about 8500 ppm chloride ions. In some embodiments, the EPA productivity is about 0.2 g/L/day to about 5 g/L/day, about 0.2 g/L/day to about 4 g/L/day, about 0.2 g/L/day to about 3 g/L/day, about 0.2 g/L/day to about 2 g/L/day, about 0.2 g/L/day to about 1 g/L/day, about 0.2 g/L/day to about 0.8 g/L/day, about 0.2 g/L/day to about 0.7 g/L/day, about 1 g/L/day to about 5 g/L/day, about 1 g/L/day to about 4 g/L/day, about 1 g/L/day to about 3 g/L/day, or about 1 g/L/day to about 2 g/L/day after growing for about 6 days, about 7 days, or about 8 days at about 15° C. to about 30° C. in a culture medium of about pH 6.5 to about pH 8.5 or about pH 6.5 to about pH 9.5 comprising sources of carbon, nitrogen, and nutrients, and about 950 ppm to about 8500 ppm chloride ions. In some embodiments, any of the aforementioned EPA productivities are associated with any of the aforementioned omega-3 fatty acid productivities. In some embodiments, the culture further comprises a DHA productivity of about 0 g/L/day to about 5 g/L/day, about 0 g/L/day to about 4 g/L/day, about 0 g/L/day to about 3 g/L/day, about 0 g/L/day to about 2 g/L/day, about 0 g/L/day to about 1 g/L/day, about 0.2 g/L/day to about 5 g/L/day, about 0.2 g/L/day to about 4 g/L/day, about 0.2 g/L/day to about 3 g/L/day, about 0.2 g/L/day to about 2 g/L/day, about 0.2 g/L/day to about 1 g/L/day, about 1 g/L/day to about 5 g/L/day, about 2 g/L/day to about 5 g/L/day, about 2 g/L/day to about 4 g/L/day, or about 2 g/L/day to about 3 g/L/day. In some embodiments, the DHA productivity is less than about 5 g/L/day, less than about 4 g/L/day, less than about 3 g/L/day, less than about 2 g/L/day, less than about 1 g/L/day, less than about 0.5 g/L/day, less than about 0.2 g/L/day, or about 0 g/L/day.

In some embodiments, the fermentation volume (volume of culture) is at least about 2 liters, at least about 10 liters, at least about 50 liters, at least about 100 liters, at least about 200 liters, at least about 500 liters, at least about 1000 liters, at least about 10,000 liters, at least about 20,000 liters, at least about 50,000 liters, at least about 100,000 liters, at least about 150,000 liters, at least about 200,000 liters, or at least about 250,000 liters. In some embodiments, the fermentation volume is about 2 liters to about 300,000 liters, about 2 liters, about 10 liters, about 50 liters, about 100 liters, about 200 liters, about 500 liters, about 1000 liters, about 10,000 liters, about 20,000 liters, about 50,000 liters, about 100,000 liters, about 150,000 liters, about 200,000 liters, about 250,000 liters, or about 300,000 liters.

In some embodiments, the invention is directed to an isolated biomass comprising a fatty acid profile of the invention. In some embodiments, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the dry cell weight of the biomass are fatty acids. In some embodiments, greater than about 20%, greater than about 25%, greater than about 30%, greater than about 35%, greater than about 40%, greater than about 45%, greater than about 50%, greater than about 55%, or greater than about 60% of the dry cell weight of the biomass are fatty acids. In some embodiments, about 20% to about 55%, about 20% to about 60%, about 20% to about 70%, about 20% to about 80%, about 30% to about 55%, about 30% to about 70%, about 30% to about 80%, about 40% to about 60%, about 40% to about 70%, about 40% to about 80%, about 50% to about 60%, about 50% to about 70%, about 50% to about 80%, about 55% to about 70%, about 55% to about 80%, about 60% to about 70%, or about 60% to about 80% by weight of the dry cell weight of the biomass are fatty acids. In some embodiments, the biomass comprises more than about 10%, at least about 12%, at least about 15%, at least about 20%, at least about 25%, at least about 30%, about least about 35%, at least about 40%, or at least about 45% by weight of the fatty acids as EPA. In some embodiments, the biomass comprises about 10% to about 55%, about 12% to about 55%, about 15% to about 55%, about 20% to about 55%, about 20% to about 40%, or about 20% to about 30% by weight of the fatty acids as EPA. In some embodiments, the biomass comprises a triacylglycerol fraction, wherein at least about 12%, at least about 13%, at least about 14%, at least about 15%, at least about 16%, at least about 17%, at least about 18%, at least about 19%, or at least about 20% by weight of the triacylglycerol fraction is EPA. In some embodiments, the biomass comprises a triacylglycerol fraction, wherein the EPA content of the triacylglycerol fraction is from at least about 12% to about 55%, about 12% to about 50%, about 12% to about 45%, at least about 12% to about 40%, at least about 12% to about 35%, or at least about 12% to about 30%, about 15% to about 55%, about 15% to about 50%, about 15% to about 45%, about 15% to about 40%, about 15% to about 35%, about 15% to about 30%, about 20% to about 55%, about 20% to about 50%, about 20% to about 45%, at least about 20% to about 40%, at least about 20% to about 35%, or about 20% to about 30% by weight. In some embodiments, at least about 20%, at least about 25%, at least about 30%, at least about 35%, at least about 40%, at least about 50%, or at least about 60% by weight of the dry cell weight of the biomass is DHA. In some embodiments, about 20% to about 60%, about 25% to about 60%, about 25% to about 50%, about 25% to about 45%, about 30% to about 50%, or about 35% to about 50% by weight of the dry cell weight of the biomass is DHA. In some embodiments, the biomass comprises about 10% or less, about 9% or less, about 8% or less, about 7% or less, about 6% or less, about 5% or less, about 4% or less, about 3% or less, about 2% or less, or about 1% or less by weight of the fatty acids as DHA. In some embodiments, the biomass comprises about 1% to about 10%, about 1% to about 5%, about 2% to about 5%, about 3% to about 5%, or about 3% to about 10% by weight of the fatty acids as DHA. In some embodiments, the biomass is substantially free of DHA. In some embodiments, the biomass comprises about 0.1% to less than about 5%, about 0.1% to about 4%, about 0.1% to about 3%, about 0.1% to about 2%, about 0.2% to less than about 5%, about 0.2% to about 4%, about 0.2% to about 3%, about 0.2% to about 2%, about 0.3% to about 2%, about 0.1% to about 0.5%, about 0.2% to about 0.5%, about 0.1% to about 0.4%, about 0.2% to about 0.4%, about 0.5% to about 2%, about 1% to about 2%, about 0.5% to about 1.5%, or about 1% to about 1.5% by weight of the fatty acids as ARA. In some embodiments, the biomass comprises less than about 5%, about 4% or less, about 3% or less, about 2% or less, about 1.5% or less, about 1% or less, about 0.5% or less, about 0.4% or less, about 0.3% or less, about 0.2% or less, or about 0.1% or less by weight of the fatty acids as ARA. In some embodiments, the biomass is substantially free of ARA. In some embodiments, the biomass comprises about 0.4% to about 2%, about 0.4% to about 3%, about 0.4% to about 4%, about 0.4% to about 5%, about 0.4% to less than about 5%, about 0.5% to about 1%, about 0.5% to about 2%, about 0.5% to about 3%, about 0.5% to about 4%, about 0.5% to about 5%, about 0.5% to less than about 5%, about 1% to about 2%, about 1% to about 3%, about 1% to about 4%, about 1% to about 5%, or about 1% to less than about 5% by weight of the fatty acids as DPA n-6. In some embodiments, the biomass comprises about 5% or less, less than about 5%, about 4% or less, about 3% or less, about 2% or less, about 1% or less, about 0.75% or less, about 0.6% or less, or about 0.5% or less by weight of the fatty acids as DPA n-6. In some embodiments, the biomass is substantially free of DPA n-6. In some embodiments, the biomass comprises fatty acids with about 5% or less, less than about 5%, about 4% or less, about 3% or less, or about 2% or less by weight of oleic acid (18:1 n-9), linoleic acid (18:2 n-6), linolenic acid (18:3 n-3), eicosenoic acid (20:1 n-9), erucic acid (22:1 n-9), or combinations thereof. The characteristics of an isolated biomass of the invention are associated with endogenous or native properties of the isolated biomass rather than exogenously introduced materials. In some embodiments, the isolated biomass does not contain polyvinylpyrrolidone or is not isolated from a culture containing polyvinylpyrrolidone.

The present invention is directed to a method of producing a biomass. In some embodiments, the method for producing a biomass of the invention comprises growing any of the isolated recombinant host cells of the invention or mixtures thereof in a culture to produce a biomass. The present invention is directed to a biomass produced by the method.

Microbial Oils

The invention is directed to a microbial oil comprising a fatty acid profile of the invention. A microbial oil of the invention is a "crude oil" or a "refined oil" comprising a triacylglycerol fraction of at least about 35% by weight. A "crude oil" is an oil that is extracted from the biomass of the recombinant host cell without further processing. A "refined oil" is an oil that is obtained by treating a crude oil with standard processing of refining, bleaching, and/or deodorizing. See, e.g., U.S. Pat. No. 5,130,242, incorporated by reference herein in its entirety. A microbial oil also includes a "final oil" as described herein, which is a refined oil that has been diluted with a vegetable oil. In some embodiments, a final oil is a refined oil that has been diluted with high oleic sunflower oil. The term "microbial" as used herein includes, but is not limited to, the terms "microalgal," "thraustochytrid," and taxonomic classifications associated with any of the host cells described herein. The terms "Thraustochytriales," "thraustochytrid," "Schizochytrium," and "Thraustochytrium" as used in reference to any of the microbial oils of the host cells described herein are based on present taxonomic classifications including available phylogenetic information and are not intended to be limiting in the event that the taxonomic classifications are revised after the filing date of the present application.

In some embodiments, a fatty acid as described herein can be a fatty acid ester. In some embodiments, a fatty acid ester includes an ester of an omega-3 fatty acid, omega-6 fatty acid, and combinations thereof. In some embodiments, the fatty acid ester is a DHA ester, an EPA ester, or a combination thereof. In some embodiments, an oil or fraction thereof as described herein is esterified to produce an oil or fraction thereof comprising fatty acid esters. The term "ester" refers to the replacement of the hydrogen in the carboxylic acid group of the fatty acid molecule with another substituent. Typical esters are known to those in the art, a discussion of which is provided by Higuchi, T. and V. Stella in Pro-drugs as Novel Delivery Systems, Vol. 14, *A.C.S. Symposium Series*, Bioreversible Carriers in Drug Design, Ed. Edward B. Roche, American Pharmaceutical Association, Pergamon Press, 1987, and Protective Groups in Organic Chemistry, McOmie ed., Plenum Press, New York, 1973. Examples of esters include methyl, ethyl, propyl, butyl, pentyl, t-butyl, benzyl, nitrobenzyl, methoxybenzyl, benzhydryl, and trichloroethyl. In some embodiments, the ester is a carboxylic acid protective ester group, esters with aralkyl (e.g., benzyl, phenethyl), esters with lower alkenyl (e.g., allyl, 2-butenyl), esters with lower-alkoxy-lower-alkyl (e.g., methoxymethyl, 2-methoxyethyl, 2-ethoxyethyl), esters with lower-alkanoyloxy-lower-alkyl (e.g., acetoxymethyl, pivaloyloxymethyl, 1-pivaloyloxyethyl), esters with lower-alkoxycarbonyl-lower-alkyl (e.g., methoxycarbonylmethyl, isopropoxycarbonylmethyl), esters with carboxy-lower alkyl (e.g., carboxymethyl), esters with lower-alkoxycarbonyloxy-lower-alkyl (e.g., 1-(ethoxycarbonyloxy)ethyl, 1-(cyclohexyloxycarbonyloxy)ethyl), esters with carbamoyloxy-lower alkyl (e.g., carbamoyloxymethyl), and the like. In some embodiments, the added substituent is a linear or cyclic hydrocarbon group, e.g., a C1-C6 alkyl, C1-C6 cycloalkyl, C1-C6 alkenyl, or C1-C6 aryl ester. In some embodiments, the ester is an alkyl ester, e.g., a methyl ester, ethyl ester or propyl ester. In some embodiments, the ester substituent is added to the free fatty acid molecule when the fatty acid is in a purified or semi-purified state. Alternatively, the fatty acid ester is formed upon conversion of a triacylglycerol to an ester.

The present invention is directed to methods of producing microbial oils. In some embodiments, the method comprises growing any of the isolated recombinant host cells of the invention or mixtures thereof in a culture to produce a microbial oil comprising omega-3 fatty acids. In some embodiments, the method further comprises extracting the microbial oil. In some embodiments, the method comprises extracting a microbial oil comprising omega-3 fatty acids from any of the biomasses of the invention or mixtures thereof. In some embodiments, the method comprises heterotrophically growing the isolated recombinant host cells, wherein the culture comprises a carbon source as described herein. The microbial oil can be extracted from a freshly harvested biomass or can be extracted from a previously harvested biomass that has been stored under conditions that prevent spoilage. Known methods can be used to culture a recombinant host cell of the invention, to isolate a biomass from the culture, to extract a microbial oil from the biomass, and to analyze the fatty acid profile of oils extracted from the biomass. See, e.g., U.S. Pat. No. 5,130,242, incorporated by reference herein in its entirety. The invention is directed to a microbial oil produced by any of the methods of the invention.

In some embodiments, the microbial oil comprises a sterol esters fraction of about 0%, at least about 0.1%, at least about 0.2%, at least about 0.5%, at least about 1%, at least about 1.5%, at least about 2%, or at least about 5% by weight. In some embodiments, the microbial oil comprises a sterol esters fraction of about 0% to about 1.5%, about 0% to about 2%, about 0% to about 5%, about 1% to about 1.5%, about 0.2% to about 1.5%, about 0.2% to about 2%, or about 0.2% to about 5% by weight. In some embodiments, the microbial oil comprises a sterol esters fraction of about 5% or less, about 4% or less, about 3% or less, about 2% or less, about 1% or less, about 0.5% or less, about 0.3% or less, about 0.2% or less, about 0.5% or less, about 0.4% or less, about 0.3% or less, or about 0.2% or less by weight.

In some embodiments, the microbial oil comprises a triacylglycerol fraction of at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some embodiments, the microbial oil comprises a triacylglycerol fraction of about 35% to about 98%, about 35% to about 90%, about 35% to about 80%, about 35% to about 70%, about 35% to about 70%, about 35% to about 65%, about 40% to about 70%, about 40% to about 65%, about 40% to about 55%, about 40% to about 50%, about 65% to about 95%, about 75% to about 95%, about 75% to about 98%, about 80% to about 95%, about 80% to about 98%, about 90% to about 96%, about 90% to about 97%, about 90% to about 98%, about 90%, about 95%, about 97%, or about 98% by weight.

In some embodiments, the microbial oil comprises a diacylglycerol fraction of at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 10% to about 45%, about 10% to about 40%, about 10% to about 35%, about 10% to about 30%, about 15% to about 40%, about 15% to about 35%, or about 15% to about 30% by weight. In some embodiments, the microbial oil comprises a 1,2-diacylglycerol fraction of at least about 0.2%, at least about 0.3%, at least about 0.4%, at least about 0.5%, at least about 1%, at least about 5%, at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 0.2% to about 45%, about 0.2% to about 30%, about 0.2% to about 20%, about 0.2% to about 10%, about 0.2% to about 5%, about 0.2% to about 1%, about 0.2% to about 0.8%, about 0.4% to about 45%, about 0.4% to about 30%, about 0.4% to about 20%, about 0.4% to about 10%, about 0.4% to about 5%, about 0.4% to about 1%, about 0.4% to about 0.8%, about 0.5% to about 1%, about 0.5% to about 0.8%, about 10% to about 45%, about 10% to about 40%, about 10% to about 35%, about 10% to about 30%, about 15% to about 40%, about 15% to about 35%, about 15% to about 30%, or about 15% to about 25% by weight. In some embodiments, the microbial oil comprises a 1,3-diacylglycerol fraction of at least about 0.1%, at least about 0.2%, at least about 0.5%, at least about 1%, at least about 2%, at least about 2.5%, or at least about 3% by weight. In some embodiments, the microbial oil comprises a sterol fraction of at least about 0.3%, at least about 0.4%, at least about 0.5%, at least about 1%, at least about 1.5%, at least about 2%, or at least about 5% by weight.

In some embodiments, the microbial oil comprises a sterol fraction of about 0.3% to about 5%, about 0.3% to about 2%, about 0.3% to about 1.5%, about 0.5% to about 1.5%, about 1% to about 1.5%, about 0.5% to about 2%, about 0.5% to about 5%, about 1% to about 2%, or about 1% to about 5% by weight. In some embodiments, the microbial oil comprises a sterol fraction of about 5% or less, about 4% or less, about 3% or less, about 2% or less, about 1.5% or less, or about 1% or less by weight.

In some embodiments, the microbial oil comprises a phospholipid fraction of at least about 2%, at least about 5%, or at least about 8% by weight. In some embodiments, the microbial oil comprises a phospholipid fraction of about 2% to about 25%, about 2% to about 20%, about 2% to about 15%, about 2% to about 10%, about 5% to about 25%, about 5% to about 20%, about 5% to about 20%, about 5% to about 10%, or about 7% to about 9% by weight. In some embodiments, the microbial oil comprises a phospholipid fraction of less than about 20%, less than about 15%, less than about 10%, less than about 9%, or less than about 8% by weight. In some embodiments, the microbial oil is substantially free of phospholipids. In some embodiments, the microbial oil comprises unsaponifiables of less than about 2%, less than about 1.5%, less than about 1%, or less than about 0.5% by weight of the oil. The lipid classes present in the microbial oil, such as a triacylglycerol fraction, can be separated by flash chromatography and analyzed by thin layer chromatography (TLC), or separated and analyzed by other methods known in the art.

In some embodiments, the microbial oil and/or one or more fractions thereof selected from the triacylglycerol fraction, the free fatty acid fraction, the sterol fraction, the diacylglycerol fraction, and combinations thereof, comprises at least about 5%, at least about 10%, more than about 10%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, or at least about 45% by weight EPA. In some embodiments, the microbial oil and/or one or more fractions thereof selected from the triacylglycerol fraction, the free fatty acid fraction, the sterol fraction, the diacylglycerol fraction, and combinations thereof, comprises about 5% to about 55%, about 5% to about 50%, about 5% to about 45%, about 5% to about 40%, about 5% to about 35%, about 5% to about 30%, about 10% to about 55%, about 10% to about 50%, about 10% to about 45%, about 10% to about 40%, about 10% to about 35%, about 10% to about 30%, at least about 12% to about 55%, at least about 12% to about 50%, at least about 12% to about 45%, at least about 12% to about 40%, at least about 12% to about 35%, or at least about 12% to about 30%, about 15% to about 55%, about 15% to about 50%, about 15% to about 45%, about 15% to about 40%, about 15% to about 35%, about 15% to about 30%, about 15% to about 25%, about 15% to about 20%, about 20% to about 55%, about 20% to about 50%, about 20% to about 45%, about 20% to about 40%, or about 20% to about 30% by weight EPA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises at least about 5%, at least about 10%, at least about 15%, at least about 20%, at least about 25%, at least about 30%, at least about 35%, at least about 40%, at least about 50%, or at least about 60% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% to about 60%, about 5% to about 55%, about 5% to about 50%, about 5% to about 40%, about 10% to about 60%, about 10% to about 50%, about 10% to about 40%, about 20% to about 60%, about 25% to about 60%, about 25% to about 50%, about 25% to about 45%, about 30% to about 50%, about 35% to about 50%, or about 30% to about 40% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 10% or less, about 9% or less, about 8% or less, about 7% or less, about 6% or less, about 5% or less, about 4% or less, about 3% or less, about 2% or less, or about 1% or less by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 1% to about 10%, about 1% to about 5%, about 2% to about 5%, about 3% to about 5%, or about 3% to about 10% by weight of the fatty acids as DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.1% to about 5%, about 0.1% to less than about 5%, about 0.1% to about 4%, about 0.1% to about 3%, about 0.1% to about 2%, about 0.2% to about 5%, about 0.2% to less than about 5%, about 0.2% to about 4%, about 0.2% to about 3%, about 0.2% to about 2%, about 0.3% to about 2%, about 0.1% to about 0.5%, about 0.2% to about 0.5%, about 0.1% to about 0.4%, about 0.2% to about 0.4%, about 0.5% to about 2%, about 1% to about 2%, about 0.5% to about 1.5%, or about 1% to about 1.5% by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% or less, less than about 5%, about 4% or less, about 3% or less, about 2% or less, about 1.5% or less, about 1% or less, about 0.5% or less, about 0.4% or less, about 0.3% or less, about 0.2% or less, or about 0.1% or less by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.4% to about 2%, about 0.4% to about 3%, about 0.4% to about 4%, about 0.4% to about 5%, about 0.4% to less than about 5%, about 0.5% to about 1%, about 0.5% to about 2%, about 0.5% to about 3%, about 0.5% to about 4%, about 0.5% to about 5%, about 0.5% to less than about 5%, about 1% to about 2%, about 1% to about 3%, about 1% to about 4%, about 1% to about 5%, or about 1% to less than about 5% by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5%, less than about 5%, about 4% or less, about 3% or less, about 2% or less, about 1% or less, about 0.75% or less, about 0.6% or less, or about 0.5% or less by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises fatty acids with about 5% or less, less than about 5%, about 4% or less, about 3% or less, or about 2% or less by weight of oleic acid (18:1 n-9), linoleic acid (18:2 n-6), linolenic acid (18:3 n-3), eicosenoic acid (20:1 n-9), erucic acid (22:1 n-9), stearidonic acid (18:4 n-3), or combinations thereof.

The triacylglycerol molecule contains 3 central carbon atoms (C(sn-1)H2R1-(sn-2)H2R2-C(sn-3)H2R3), allowing for formation of different positional isomers. In some embodiments, the microbial oil comprises a triacylglycerol fraction in which at least about 2%, at least about 3%, at least about 5%, at least about 10%, at least about 15%, at least about 20%, at least about 30%, at least about 35%, or at least about 40% of the triacylglycerols in the triacylglycerol fraction contain DHA at two positions in the triacylglycerol (di-substituted DHA) selected from any two of the sn-1, sn-2, and sn-3 positions, based on the relative area percent of peaks on an HPLC chromatograph. In some embodiments, the microbial oil comprises a triacylglycerol fraction in which about 2% to about 55%, about 2% to about 50%, about 2% to about 45%, about 2% to about 40%, about 2% to about 35%, about 2% to about 30%, about 2% to about 25%, about 5% to about 55%, about 5% to about 50%, about 5% to about 45%, about 5% to about 40%, about 5% to about 35%, about 5% to about 30%, about 5% to about 25%, about 10% to about 55%, about 10% to about 50%, about 10% to about 45%, about 10% to about 40%, about 10% to about 35%, about 10% to about 30%, about 10% to about 25%, about 10% to about 20%, about 20% to about 40%, about 20% to about 35%, or about 20% to about 25% of the triacylglycerols in the triacylglycerol fraction contain EPA at two positions in the triacylglycerol selected from any two of the sn-1, sn-2, or sn-3 positions, based on the relative area percent of peaks on an HPLC chromatograph. In some embodiments, the microbial oil comprises a triacylglycerol fraction in which at least about 0.5%, at least about 1%, at least about 1.5%, or at least about 2% of the triacylglycerols in the triacylglycerol fraction contain DHA at all of the sn-1, sn-2, and sn-3 positions (tri-substituted DHA), based on the relative area percent of peaks on an HPLC chromatograph. In some embodiments, the microbial oil comprises a triacylglycerol fraction in which about 0.5% to about 5%, about 0.5% to about 3%, about 0.5% to about 2.5%, about 0.5% to about 2%, about 1% to about 5%, about 1% to about 3%, or about 1% to about 2% of the triacylglycerols in the triacylglycerol fraction contain DHA at all of the sn-1, sn-2, and sn-3 positions, based on the relative area percent of peaks on an HPLC chromatograph. In some embodiments, the microbial oil comprises a triacylglycerol fraction in which at least about 10%, at least about 15%, at least about 20%, at least about 25%, at least about 30%, at least about 35%, at least about 40%, at least about 45%, at least about 50%, at least about 55%, or at least about 60% of the triacylglycerols in the triacylglycerol fraction contain DHA at one position in the triacylglycerol selected from any one of the sn-1, sn-2, or sn-3 positions, based on the relative area percent of peaks on an HPLC chromatograph. In some embodiments, the microbial oil comprises a triacylglycerol fraction in which about 10% to about 80%, about 10% to about 70%, about 10% to about 60%, about 15% to about 80%, about 15% to about 75%, about 15% to about 70%, about 15% to about 65%, about 15% to about 60%, about 35% to about 80%, about 35% to about 75%, about 35% to about 65%, about 35% to about 60%, about 40% to about 80%, about 40% to about 75%, about 40% to about 70%, about 40% to about 65%, about 40% to about 60%, or about 40% to about 55% of the triacylglycerols in the triacylglycerol fraction contain DHA at one position in the triacylglycerol selected from any one of the sn-1, sn-2, and sn-3 positions, based on the relative area percent of peaks on an HPLC chromatograph.

Compositions

The invention is directed to compositions comprising a recombinant host cell of the invention, an isolated biomass of the invention, a microbial oil of the invention, or combinations thereof.

A recombinant host cell, biomass, or microbial oil of the invention can be further chemically or physically modified or processed based on the requirements of the composition by any known technique.

Recombinant host cells or biomasses can be dried prior to use in a composition by methods including, but not limited to, freeze drying, air drying, spray drying, tunnel drying, vacuum drying (lyophilization), and a similar process. Alternatively, a harvested and washed biomass can be used directly in a composition without drying. See, e.g., U.S. Pat. Nos. 5,130,242 and 6,812,009, each of which is incorporated by reference herein in its entirety.

Microbial oils of the invention can be used as starting material to more efficiently produce a product enriched in a fatty acid such as EPA. For example, the microbial oils of the invention can be subjected to various purification techniques known in the art, such as distillation or urea adduction, to produce a higher potency product with higher concentrations of EPA or another fatty acid. The microbial oils of the invention can also be used in chemical reactions to produce compounds derived from fatty acids in the oils, such as esters and salts of EPA or another fatty acid.

A composition of the invention can include one or more excipients. As used herein, "excipient" refers to a component, or mixture of components, that is used in a composition of the present invention to give desirable characteristics to the composition, including foods as well as pharmaceutical, cosmetic, and industrial compositions. An excipient of the present invention can be described as a "pharmaceutically acceptable" excipient when added to a pharmaceutical composition, meaning that the excipient is a compound, material, composition, salt, and/or dosage form which is, within the scope of sound medical judgment, suitable for contact with tissues of human beings and non-human animals without excessive toxicity, irritation, allergic response, or other problematic complications over the desired duration of contact commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, Remington: The Science and Practice of Pharmacy, $21^{st}$ ed. (2005). Inclusion of an excipient in a particular classification herein (e.g., "solvent") is intended to illustrate rather than limit the role of the excipient. A particular excipient can fall within multiple classifications.

Compositions of the invention include, but are not limited to, food products, pharmaceutical compositions, cosmetics, and industrial compositions.

In some embodiments, the composition is a food product. A food product is any food for non-human animal or human consumption, and includes both solid and liquid compositions. A food product can be an additive to animal or human foods. Foods include, but are not limited to, common foods; liquid products, including milks, beverages, therapeutic drinks, and nutritional drinks; functional foods; supplements; nutraceuticals; infant formulas, including formulas for pre-mature infants; foods for pregnant or nursing women; foods for adults; geriatric foods; and animal foods.

In some embodiments, a recombinant host cell, biomass, or microbial oil of the invention can be used directly as or included as an additive within one or more of: an oil, shortening, spread, other fatty ingredient, beverage, sauce, dairy-based or soy-based food (such as milk, yogurt, cheese and ice-cream), a baked good, a nutritional product, e.g., as a nutritional supplement (in capsule or tablet form), a vitamin supplement, a diet supplement, a powdered drink, and a finished or semi-finished powdered food product. In some embodiments, the nutritional supplement is in the form of a vegetarian capsule that is not formed from and does not contain any components from an animal source.

A partial list of food compositions that can include a microbial oil of the invention includes, but is not limited to, soy-based products (milks, ice creams, yogurts, drinks, creams, spreads, whiteners); soups and soup mixes; doughs, batters, and baked food items including, for example, fine bakery wares, breakfast cereals, cakes, cheesecakes, pies, cupcakes, cookies, bars, breads, rolls, biscuits, muffins, pastries, scones, croutons, crackers, sweet goods, snack cakes, pies, granola/snack bars, and toaster pastries; candy; hard confectionery; chocolate and other confectionery; chewing gum; liquid food products, for example milks, energy drinks, infant formula, carbonated drinks, teas, liquid meals, fruit juices, fruit-based drinks, vegetable-based drinks; multivitamin syrups, meal replacers, medicinal foods, and syrups; powdered beverage mixes; pasta; processed fish products; processed meat products; processed poultry products; gravies and sauces; condiments (ketchup, mayonnaise, etc.); vegetable oil-based spreads; dairy products; yogurt; butters; frozen dairy products; ice creams; frozen desserts; frozen yogurts; semi-solid food products such as baby food; puddings and gelatin desserts; processed and unprocessed cheese; pancake mixes; food bars including energy bars; waffle mixes; salad dressings; replacement egg mixes; nut and nut-based spreads; salted snacks such as potato chips and other chips or crisps, corn chips, tortilla chips, extruded snacks, popcorn, pretzels, potato crisps, and nuts; and specialty snacks such as dips, dried fruit snacks, meat snacks, pork rinds, health food bars and rice/corn cakes.

In some embodiments, a microbial oil of the invention can be used to supplement infant formula. Infant formula can be supplemented with a microbial oil of the invention alone or in combination with a physically refined oil derived from an arachidonic acid (ARA)-producing microorganism. An ARA-producing microorganism, for example, is *Mortierella alpina* or *Mortierella* sect. *schmuckeri*. Alternatively, infant formulas can be supplemented with a microbial oil of the invention in combination with an oil rich in ARA, including ARASCO® (Martek Biosciences, Columbia, MD).

In some embodiments, the composition is an animal feed. An "animal" includes non-human organisms belonging to the kingdom Animalia, and includes, without limitation, aquatic animals and terrestrial animals. The term "animal feed" or "animal food" refers to any food intended for non-human animals, whether for fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; or rodents such as mice, rats, hamsters and guinea pigs; and so on. An animal feed includes, but is not limited to, an aquaculture feed, a domestic animal feed including pet feed, a zoological animal feed, a work animal feed, a livestock feed, and combinations thereof.

In some embodiments, the composition is a feed or feed supplement for any animal whose meat or products are consumed by humans, such as any animal from which meat, eggs, or milk is derived for human consumption. When fed to such animals, nutrients such as LC-PUFAs can be incorporated into the flesh, milk, eggs or other products of such animals to increase their content of these nutrients.

In some embodiments, the composition is a spray-dried material that can be crumbled to form particles of an appropriate size for consumption by zooplankton, artemia, rotifers, and filter feeders. In some embodiments, the zooplankton, artemia, or rotifers fed by the composition are in turn fed to fish larvae, fish, shellfish, bivalves, or crustaceans.

In some embodiments, the composition is a pharmaceutical composition. Suitable pharmaceutical compositions include, but are not limited to, an anti-inflammatory composition, a drug for treatment of coronary heart disease, a drug for treatment of arteriosclerosis, a chemotherapeutic agent, an active excipient, an osteoporosis drug, an antidepressant, an anti-convulsant, an anti-*Helicobacter pylori* drug, a drug for treatment of neurodegenerative disease, a drug for treatment of degenerative liver disease, an antibiotic, a cholesterol lowering composition, and a triacylglycerol lowering composition. In some embodiments, the composition is a medical food. A medical food includes a food that is in a composition to be consumed or administered externally under the supervision of a physician and that is intended for the specific dietary management of a condition, for which distinctive nutritional requirements, based on recognized scientific principles, are established by medical evaluation.

In some embodiments, the microbial oil can be formulated in a dosage form. Dosage forms can include, but are not limited to, tablets, capsules, cachets, pellets, pills, powders and granules, and parenteral dosage forms, which include, but are not limited to, solutions, suspensions, emulsions, and dry powders comprising an effective amount of the microbial oil. It is also known in the art that such formulations can also contain pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. Administration forms can include, but are not limited to, tablets, dragees, capsules, caplets, and pills, which contain the microbial oil and one or more suitable pharmaceutically acceptable carriers.

For oral administration, the microbial oil can be combined with pharmaceutically acceptable carriers well known in the art. Such carriers enable the microbial oils of the invention to be formulated as tablets, pills, dragees, capsules, liquids, gels, syrups, slurries, suspensions and the like, for oral ingestion by a subject to be treated. In some embodiments, the dosage form is a tablet, pill or caplet. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, and polyvinylpyrrolidone (PVP). If desired, disintegrating agents can be added, such as, but not limited to, the cross-linked polyvinylpyrrolidone, agar, or alginic acid or a salt thereof such as sodium alginate. Pharmaceutical preparations that can be used orally include, but are not limited to, push-fit capsules made of gelatin, as well as soft, sealed capsules made of gelatin and a plasticizer, such as glycerol or sorbitol. In some embodiments, the dosage form is a vegetarian dosage form, in which the dosage form is not formed from and does not contain any components from an animal source. In some embodiments, the vegetarian dosage form is a vegetarian capsule.

In some embodiments, the composition is a cosmetic. Cosmetics include, but are not limited to, emulsions, creams, lotions, masks, soaps, shampoos, washes, facial creams, conditioners, make-ups, bath agents, and dispersion liquids. Cosmetic agents can be medicinal or non-medicinal.

In some embodiments, the composition is an industrial composition. In some embodiments, the composition is a starting material for one or more manufactures. A manufacture includes, but is not limited to, a polymer; a photographic photosensitive material; a detergent; an industrial oil; or an industrial detergent. For example, U.S. Pat. No. 7,259,006 describes use of DHA-containing fat and oil for production of behenic acid and production of photographic sensitive materials using behenic acid.

Methods of Using the Compositions

In some embodiments, the compositions can be used in the treatment of a condition in humans or non-human animals. In some embodiments, the compositions can be used for nutrition in humans or non-human animals.

The terms "treat" and "treatment" refer to both therapeutic treatment and prophylactic or preventative measures, wherein the object is to prevent or slow down (lessen) an undesired physiological condition, disease, or disorder, or to obtain beneficial or desired clinical results. For purposes of this invention, beneficial or desired clinical results include, but are not limited to, alleviation or elimination of the symptoms or signs associated with a condition, disease, or disorder; diminishment of the extent of a condition, disease, or disorder; stabilization of a condition, disease, or disorder, (i.e., where the condition, disease, or disorder is not worsening); delay in onset or progression of the condition, disease, or disorder; amelioration of the condition, disease, or disorder; remission (whether partial or total and whether detectable or undetectable) of the condition, disease, or disorder; or enhancement or improvement of a condition, disease, or disorder. Treatment includes eliciting a clinically significant response without excessive side effects. Treatment also includes prolonging survival as compared to expected survival if not receiving treatment.

In some embodiments, the composition is used to treat a condition, disease, or disorder such as acne, acute inflammation, age related maculopathy, allergy, Alzheimer's, arthritis, asthma, atherosclerosis, autoimmune disease, blood lipid disorder, breast cysts, cachexia, cancer, cardiac restenosis, cardiovascular diseases, chronic inflammation, coronary heart disease, cystic fibrosis, degenerative disorder of the liver, diabetes, eczema, gastrointestinal disorder, heart disease, high triacylglycerol levels, hypertension, hyperactivity, immunological diseases, inhibiting tumor growth, inflammatory conditions, intestinal disorders, kidney dysfunction, leukemia, major depression, multiple sclerosis, neurodegenerative disorder, osteoarthritis, osteoporosis, peroxisomal disorder, preeclampsia, preterm birth, psoriasis, pulmonary disorder rheumatoid arthritis, risk of heart disease, or thrombosis.

In some embodiments, the composition is used to increase the length of gestation of a fetus in the third trimester.

In some embodiments, the composition is used to control blood pressure.

In some embodiments, the composition is used to improve or maintain cognitive function.

In some embodiments, the composition is used to improve or maintain memory.

The composition or dosage form can be administered into the body of a subject by any route compatible with the composition or dosage form. A substance is considered to be "administered" if the substance is introduced into the body of the subject by the subject, or if another person, a machine, or a device introduces the substance into the body of the subject. "Administering," therefore, includes, e.g., self-administration, administration by others, and indirect administration. The term "continuous" or "consecutive," as used herein in reference to "administration," means that the frequency of administration is at least once daily. Note, however, that the frequency of administration can be greater than once daily and still be "continuous" or "consecutive," e.g., twice or even three times daily, as long as the dosage levels as specified herein are not exceeded. The means and methods for administration are known in the art and an artisan can refer to various pharmacologic references for guidance. For example, "Modern Pharmaceutics," Banker & Rhodes, Informa Healthcare, USA, 4th ed. (2002); and "Goodman & Gilman's The Pharmaceutical Basis of Therapeutics," McGraw-Hill Companies, Inc., New York, 10th ed. (2001) can be consulted.

By "subject," "individual," or "patient" is meant any subject, whether human or non-human, for whom diagnosis, prognosis, therapy, or administration of the composition or dosage form is desired. Mammalian subjects include, but are not limited to, humans; domestic animals; farm animals; zoo animals; sport animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; rodents such as mice, rats, hamsters and guinea pigs; and so on. The term subject also encompasses model animals, e.g., disease model animals. In some embodiments, the term subject includes valuable animals, either economically or otherwise, e.g., economically important breeding stock, racing animals, show animals, heirloom animals, rare or endangered animals, or companion animals. In certain embodiments, the subject is a human subject. In certain embodiments, the subject is a non-human subject.

The composition can be administered as a "nutritional amount," "therapeutically effective amount," a "prophylactically effective amount," a "therapeutic dose," or a "prophylactic dose." A "nutritional amount" refers to an amount effective, at dosages and for periods of time necessary, to achieve a desired nutritional result. A nutritional result can be, e.g., increased levels of a desirable fatty acid component in a subject. A "therapeutically effective amount" or "therapeutic dose" refers to an amount effective, at dosages and for periods of time necessary, to achieve a desired therapeutic result. A therapeutic result can be, e.g., lessening of symptoms, prolonged survival, improved mobility, and the like. A therapeutic result need not be a "cure." A "prophylactically effective amount" or "prophylactic dose" refers to an amount effective, at dosages and for periods of time necessary, to achieve the desired prophylactic result. Typically, since a prophylactic dose is used in subjects prior to or at an earlier stage of disease, a prophylactically effective amount will be less than a therapeutically effective amount for treatment of an advanced stage of disease.

Various dosage amounts of the composition, dosage form, or pharmaceutical composition can be administered to a subject, based on the amount of EPA or other fatty acid component of the microorganism, biomass, or microbial oil to be administered to the subject. The terms "daily dosage," "daily dosage level," and "daily dosage amount" refer herein to the total amount of EPA or other fatty acid component administered per day (per 24-hour period). Thus, for example, administration of EPA to a subject at a daily dosage of 2 mg means that the subject receives a total of 2 mg of EPA on a daily basis, whether the EPA is administered as a single dosage form comprising 2 mg EPA, or alternatively, four dosage forms comprising 0.5 mg EPA each (for a total of 2 mg EPA). In some embodiments, the daily amount of EPA is administered in a single dosage form, or in two dosage forms. The dosage forms of the present invention can be taken in a single application or multiple applications. For example, if four tablets are taken daily, each tablet comprising 0.5 mg EPA, then all four tablets can be taken once daily, or 2 tablets can be taken twice daily, or 1 tablet can be taken every 6 hours. In some embodiments, the daily dosage is about 100 mg to about 15 g of EPA. In some embodiments, the daily dosage is about 0.5 mg to about 250 mg, about 100 mg to about 250 mg, about 100 mg to about 500 mg, about 100 mg to about 1 g, about 1 g to about 2.5 g, about 1 g to about 5 g, about 1 g to about 10 g, about 1 g to about 15 g, about 5 g to about 10 g, about 5 g to about 15 g, about 10 g to about 15 g, about 100 mg to about 10 g, about 100 mg to about 5 g, or about 100 mg to about 2.5 g of EPA, DHA, or a combination thereof. In some embodiments, the composition is a dosage form that comprises about 0.5 mg to about 250 mg, 100 mg to about 250 mg, about 0.5 mg to about 500 mg, about 100 mg to about 500 mg, about 0.5 mg to about 1 g, or about 100 mg to about 1 g of EPA, DHA, or a combination thereof per dosage form.

Administration of the compositions or dosage forms of the present invention can be achieved using various regimens. For example, in some embodiments, administration occurs daily on consecutive days, or alternatively, occurs every other day (bi-daily). Administration can occur on one or more days.

Administration of the compositions and dosage forms can be combined with other regimens used for treatment of the condition. For example, the method of the present invention can be combined with diet regimens (e.g., low carbohydrate diets, high protein diets, high fiber diets, etc.), exercise regimens, weight loss regimens, smoking cessation regimens, or combinations thereof. The method of the present invention can also be used in combination with other pharmaceutical products in the treatment of the condition. The compositions or dosage forms of the present invention can be administered before or after other regimens or pharmaceutical products.

Kits Comprising the Compositions

The invention is directed to kits or packages containing one or more units of a composition of the invention. Kits or packages can include units of a food product, pharmaceutical composition, cosmetic, or industrial composition comprising the recombinant host cell, biomass, or microbial oil of the invention, or combinations thereof. Kits or packages can also include an additive comprising the recombinant host cell, biomass, or microbial oil of the invention, or combinations thereof for preparation of a food, cosmetic, pharmaceutical composition, or industrial composition.

In some embodiments, the kit or package contains one or more units of a pharmaceutical composition to be administered according to the methods of the present invention. The kit or package can contain one dosage unit, or more than one dosage unit (i.e., multiple dosage units). If multiple dosage units are present in the kit or package, the multiple dosage units can be optionally arranged for sequential administration.

The kits of the present invention can optionally contain instructions associated with the units or dosage forms of the kits. Such instructions can be in a form prescribed by a governmental agency regulating the manufacture, use or sale of pharmaceutical products, which notice reflects approval by the agency of the manufacture, use or sale for human administration to treat a condition or disorder. The instructions can be in any form which conveys information on the use of the units or dosage forms in the kit according to the methods of the invention. For example, the instructions can be in the form of printed matter, or in the form of a pre-recorded media device.

In the course of examination of a patient, a medical professional can determine that administration of one of the methods of the present invention is appropriate for the patient, or the physician can determine that the patient's condition can be improved by the administration of one of the methods of the present invention. Prior to prescribing any regimen, the physician can counsel the patient, for example, on the various risks and benefits associated with the regimen. The patient can be provided full disclosure of all known and suspected risks associated with the regimen. Such counseling can be provided verbally, as well as in written form. In some embodiments, the physician can provide the patient with literature materials on the regimen, such as product information, educational materials, and the like.

The present invention is directed to methods of educating consumers about the methods of treatment, the method comprising distributing the dosage forms with consumer information at a point of sale. In some embodiments, the distribution will occur at a point of sale having a pharmacist or healthcare provider.

The term "consumer information" can include, but is not limited to, an English language text, non-English language text, visual image, chart, telephone recording, website, and access to a live customer service representative. In some embodiments, consumer information will provide directions for use of the dosage forms according to the methods of the present invention, appropriate age use, indication, contraindications, appropriate dosing, warnings, telephone number or website address. In some embodiments, the method further comprises providing professional information to relevant persons in a position to answer consumer questions regarding use of the disclosed regimens according to the methods of the present invention. The term "professional information" includes, but is not limited to, information concerning the regimen when administered according to the methods of the present invention that is designed to enable a medical professional to answer costumer questions.

A "medical professional," includes, for example, a physician, physician assistant, nurse, nurse practitioner, pharmacist and customer service representative.

Having generally described this invention, a further understanding can be obtained by reference to the examples provided herein. These examples are for purposes of illustration only and are not intended to be limiting.

EXAMPLES

General Protocols

Unless otherwise indicated, molecular biological and biochemical manipulations described in the subsequent Examples were performed by standard methodologies as disclosed in, for example, Ausubel et al. (1995) *Current Protocols in Molecular Biology*, John Wiley & Sons; Sambrook et al. (1989) *Molecular Cloning: A Laboratory Manual*, Cold Spring Harbor Laboratory Press; and the like.

Electroporation with Enzyme Pretreatment

Cells were grown in 50 mL of M50-20 media (See U.S. Pat. No. 8,859,855, Weaver et al. 2014) on a shaker at 200 rpm for 2 days at 30° C. The cells were diluted at 1:100 into M2B media See U.S. Pat. No. 8,859,855, Weaver et al. 2014) and grown overnight (16-24 h), attempting to reach mid-log phase growth (OD600 of 1.5-2.5). The cells were centrifuged in a 50 mL conical tube for 5 min at about 3000×g. The supernatant was removed and the cells were resuspended in 1 M mannitol, pH 5.5, in a suitable volume to reach a final concentration of 2 OD600 units. 5 mL of cells were aliquoted into a 25 mL shaker flask and amended with 10 mM $CaCl_2$) (1.0 M stock, filter sterilized) and 0.25 mg/mL Protease XIV (10 mg/mL stock, filter sterilized; Sigma-Aldrich, St. Louis, MO). Flasks were incubated on a shaker at 30° C. and about 100 rpm for 4 h. Cells were monitored under the microscope to determine the degree of protoplasting, with single cells desired. The cells were centrifuged for 5 min at about 2500×g in round-bottom tubes (i.e., 14 mL Falcon™ tubes, BD Biosciences, San Jose, CA). The supernatant was removed and the cells were gently resuspended with 5 mL of ice cold 10% glycerol. The cells were re-centrifuged for 5 min at about 2500×g in round-bottom tubes. The supernatant was removed and the cells were gently resuspended with 500 μL of ice cold 10% glycerol, using wide-bore pipette tips. 90 μL of cells were aliquoted into a pre-chilled electro-cuvette (Gene Pulser® cuvette—0.1 cm gap or 0.2 cm gap, Bio-Rad, Hercules, CA). One μg to 5 μg of DNA (in less than or equal to a 10 μL volume) was added to the cuvette, mixed gently with a pipette tip, and placed on ice for 5 min. Cells were electroporated at 200 ohms (resistance), 25 μF (capacitance), and either 250V (for 0.1 cm gap) or 500V (0.2 cm gap). 0.5 mL of M50-20 media was added immediately to the cuvette. The cells were then transferred to 4.5 mL of M50-20 media in a 25 mL shaker flask and incubated for 2-3 h at 30° C. and about 100 rpm on a shaker. The cells were centrifuged for 5 min at about 2500×g in round bottom tubes. The supernatant was removed and the cell pellet was resuspended in 0.5 mL of M50-20 media. Cells were plated onto an appropriate number (2 to 5) of M2B plates with appropriate selection and incubated at 30° C.

Total Fatty Acid Methyl Ester (FAME) Production

In brief, cells were grown in M2B liquid media (see U.S. Pat. No. 8,637,651) at 30° C. with 200 rpm shaking for 3 days. Alternatively, cells were also grown for 1-2 days in M50-20 liquid media followed by transfer of 2 OD units to 50 mL fresh SSFM liquid medium (see U.S. Pat. No. 8,637,651) and grown for around 4 days at 27° C. in baffled 250 mL shake flasks with 200 rpm shaking. Cells were harvested and the fatty acids were converted to methyl-esters using standard techniques. Fatty acid profiles were determined using gas chromatography with flame ionization detection (GC-FID) as fatty acid methyl esters (FAME).

Example 1

Targeted Replacement of Native PUFA Synthase Genes in *Schizochytrium* sp. N230D with PUFA Synthase Genes from *Schizochytrium* sp. ATCC PTA-9695

*Schizochytrium* sp. N230D is a daughter of *Schizochytrium* sp. ATCC 20888; cells of *Schizochytrium* sp. ATCC 20888 were subjected to chemical mutagenesis and clones from that procedure were analyzed for desirable growth characteristics, leading to the identification of *Schizochytrium* sp. N230D. Like *Schizochytrium* sp. ATCC 20888, *Schizochytrium* sp. N230D is haploid and does not harbor a complete classical pathway for PUFA biosynthesis. It is missing a Δ 12 desaturase and shows very limited activity for the other enzymes of the pathway. (See Metz et al., *Plant Physiol. Biochem.* 47(6):472-478 (2009)); Lippmeier et al. *Lipids.* 44:621-630 (2009)). The native PUFA synthase of this organism produces DHA and docosapentaenoic acid (DPA n-6) at a ratio similar to that observed in *Schizochytrium* sp. ATCC 20888.

The nucleotide sequences of the coding regions of PFA1, PFA2, and PFA3 of *Schizochytrium* sp. ATCC 20888 and *Schizochytrium* sp. N230D are identical. The generation of vectors to recombinantly express PFA1, PFA2, and PFA3 has been previously demonstrated and described. See, e.g., U.S. Pat. No. 8,940,884, incorporated by reference herein in its entirety.

The native PFA3 gene in *Schizochytrium* sp. N230D was replaced by homologous recombination following transformation with a linearized vector containing the paromomycin resistance marker surrounded by sequences from the PFA3 flanking region (plasmid pDS97). A mutant strain was generated lacking a functional PFA3 gene (B142). The mutant strain was auxotrophic and required PUFA supplementation for growth.

*Schizochytrium* sp. ATCC PTA-9695 PFA3 (SEQ ID NO:5) was cloned into expression vector pREZ22 to generate pREZ324. The expression vector contained approximately 2 kb of DNA from the flanking region of the native PFA3 gene locus from *Schizochytrium* sp. ATCC 20888.

The *Schizochytrium* sp. N230D mutant lacking functional PFA3 was transformed with linearized pREZ324 containing *Schizochytrium* sp. ATCC PTA-9695 PFA3. Based on homologous regions flanking the paromomycin resistance marker in the mutant and flanking the Schizochytrium sp. ATCC PTA-9695 PFA3 gene in pREZ324, recombination occurred such that *Schizochytrium* sp. ATCC PTA-9695 PFA3 was inserted into the native PFA3 locus. This mutant strain was termed B154.

Figure 3:
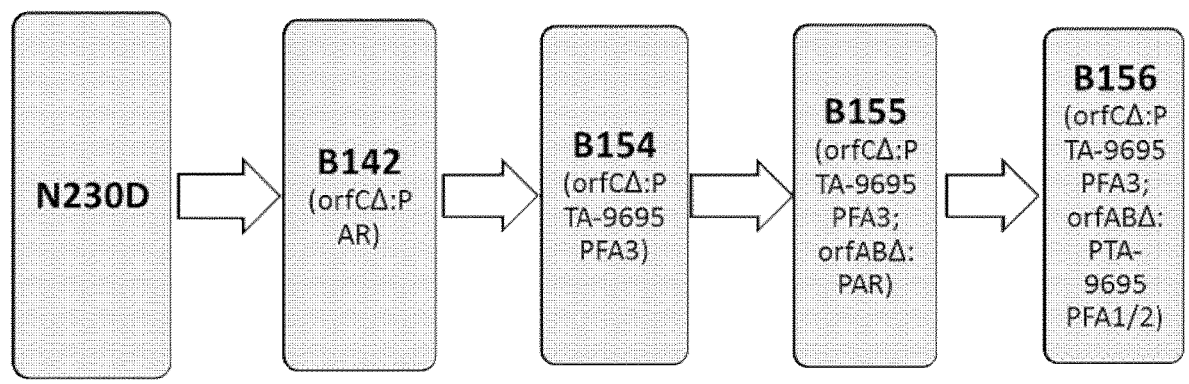
FIG. 3 shows the strain lineage of Schizochytrium strain B156 which was produced by targeted replacement of the native PUFA synthase subunit genes in *Schizochytrium* sp. N230D with the PUFA synthase subunit genes from *Schizochytrium* sp. ATCC PTA-9695 as described further in Example 1.

The native PFA1 and PFA2 genes in Schizochytrium mutant strain B154 were replaced with the PFA1 and PFA2 genes from *Schizochytrium* sp. ATCC PTA-9695 using a similar strategy as described for the PFA3 gene replacement. Replacement of these two genes was facilitated by their head to head arrangement (see FIG. 1). Transformation of strain B154 with a vector containing the paromomycin resistance marker surrounded by sequences from the PFA1 and PFA2 downstream flanking regions (plasmid pCX023) resulted in replacement of the PFA1 and PFA2 locus with the resistance marker. This auxotrophic mutant strain was termed B155. Strain B155 was transformed with pLP112 containing *Schizochytrium* sp. ATCC PTA-9695 PFA1 (SEQ ID NO:1) and *Schizochytrium* sp. ATCC PTA-9695 PFA2 (SEQ ID NO:3) arranged head to head with the native *Schizochytrium* sp. ATCC 20888 intergenic region between the genes and with around 2 kb of the *Schizochytrium* sp. ATCC 20888 PFA1 and PFA2 downstream flanking regions. Recombination occurred such that *Schizochytrium* sp. ATCC PTA-9695 PFA1 was inserted into the native PFA1 locus and *Schizochytrium* sp. ATCC PTA-9695 PFA2 was inserted into the native PFA2 locus of the strain. The resulting recombinant strain (B156) lacked the native PFA1, PFA2, and PFA3 coding sequences and contained *Schizochytrium* sp. ATCC PTA-9695 PFA1, PFA2, and PFA3 inserted into the respective PFA1, PFA2, and PFA3 loci. The genes were driven by the native PFA1/2 and PFA3 promoters, respectively. B156 recovered PUFA prototrophy and did not contain any resistance markers. The genomic structures of all transgenic strains of interest were confirmed by PCR and southern blotting. A schematic for the process is provided in FIG. 3.

As shown in FIG. 4A, the *Schizochytrium* sp. N230D strain containing its native PFA1, PFA2, and PFA3 genes produced 0.39% EPA (% of total FAME produced), 8.20% DPA n-6, and 28.39% DHA after growth at 25° C. The recombinant strain B156-2 containing *Schizochytrium* sp. ATCC PTA-9695 PFA1 (SEQ ID NO:1), PFA2 (SEQ ID NO: 3), and PFA3 (SEQ ID NO: 5) in place of the deleted native PFA1, PFA2, and PFA3 coding regions produced 1.12% EPA, 1.78% DPA n-6, and 28.56% DHA after culture at 25° C.

FAME composition of the strains was also determined after growth at 30° C., as shown in FIG. 4B. The *Schizochytrium* sp. N230D strain containing its native PFA1, PFA2, and PFA3 genes produced 0.60% EPA (% of total FAME produced), 13.16% DPA n-6, and 32.34% DHA after culture at 30° C. The recombinant strain B156 containing *Schizochytrium* sp. ATCC PTA-9695 PFA1 (SEQ ID NO:1), PFA2 (SEQ ID NO: 3), and PFA3 (SEQ ID NO: 5) in place of the inactivated PFA1, PFA2, and PFA3 genes produced 1.17% EPA, 3.03% DPA n-6, and 28.46% DHA after growth at 30° C.

Example 2

Replacement of Native PUFA Synthase Subunit Genes in *Schizochytrium* sp. ATCC 20888 with PUFA Synthase Subunit Genes from *Schizochytrium* sp. ATCC PTA-9695 Integrated in the Genome in a Random Fashion The inactivation of native PUFA synthase genes in *Schizochytrium* sp. ATCC 20888, to generate PUFA auxotrophs, and the replacement of such inactivated genes with exogenously introduced homologous genes to restore PUFA synthesis has been previously demonstrated and described. See, e.g., U.S. Pat. No. 7,217,856, incorporated by reference herein in its entirety and Example 1, above.

The native PFA1 and PFA2 coding regions in *Schizochytrium* sp. ATCC 20888 were knocked-out by homologous recombination following transformation with a plasmid containing a Zeocin™ resistance cassette placed between about 2 kb of the PFA1 and PFA2 downstream flanking DNAs. Similarly, the PFA3 coding region was deleted by transformation with a plasmid containing a paromornycin resistance cassette flanked by the native PFA3 up and down stream DNA. The resulting strain was termed B122-17 (*Schizochytrium* sp. ATCC 20888 ΔPFA1,2,3—also referred to as ΔorfA,B,C). B122-17 is auxotrophic and requires PUFA supplementation.

The Schizochytrium strain B122-17 was transformed simultaneously with circular vectors pREZ345, pREZ331, and pREZ324 containing the genes Orfs for PFA1, PFA2, and PFA3 from *Schizochytrium* sp. ATCC PTA-9695 (See U.S. Pat. No. 8,940,884, Examples 7 and 9, for details regarding the vectors). Briefly, pREZ345 contains the sequence of *Schizochytrium* sp. ATCC PTA-9695 PFA1 surrounded by approximately 2 kb of DNA from the flanking regions of the native PFA1. pREZ331 contains the sequence of *Schizochytrium* sp. ATCC PTA-9695 PFA2 surrounded by approximately 2 kb of DNA from the flanking regions of the native PFA2. pREZ324 contains the sequence of *Schizochytrium* sp. ATCC PTA-9695 PFA3 surrounded by approximately 2 kb of DNA from the flanking regions of the native PFA3. Transformants were selected based on growth on media without PUFA supplementation, indicating the functional integration of all three PUFA synthase subunit genes had occurred. The prototrophic strains that emerged from this transformation were termed B149, and the individual isolates designated by a dash #(e.g., B149-E1, or B149-3).

Since the strain used for the transformation (B122-17) lacks the PFA1/PFA2 intergenic DNA, mechanisms other than homologous double cross-over events for the PFA1 and PFA2 genes are likely to account for their integration events. The newly introduced PFA3 gene could integrate at the PFA3 locus (via homologous double cross-over recombination) or elsewhere. In addition, the use of circular vectors could favor single cross-over events or ectopic integrations.

Figure 5:
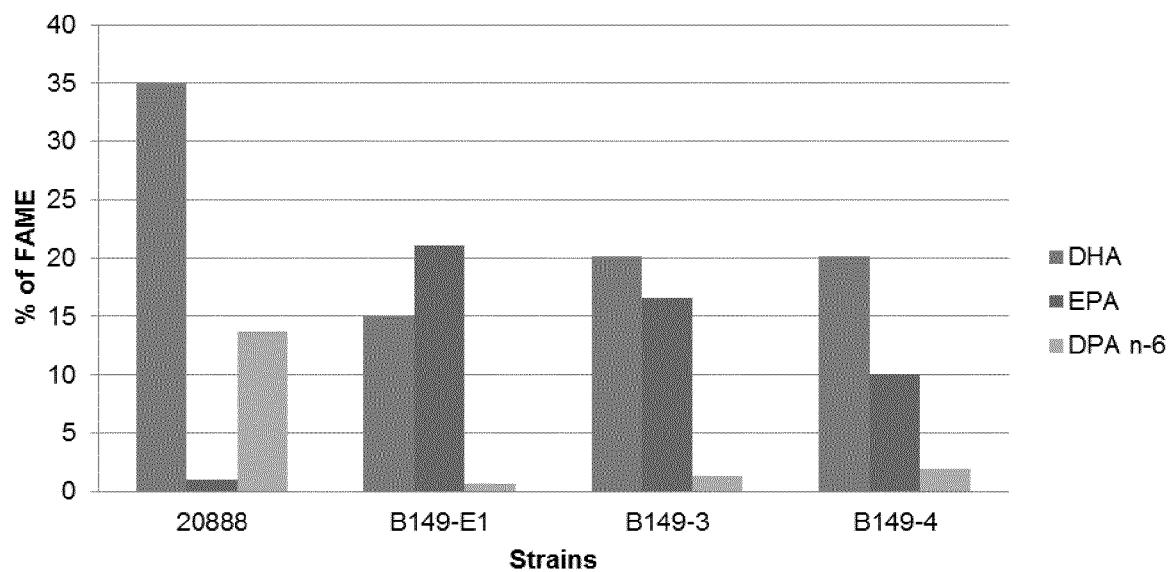
FIG. 5 shows FAME profiles after culture at 30° C. in the native *Schizochytrium* sp. ATCC 20888 containing the endogenous PFA1, PFA2, and PFA3 PUFA synthase genes compared to the recombinant *Schizochytrium* sp. ATCC 20888 in which the endogenous PFA1, PFA2, and PFA3 genes have been removed and the PFA1, PFA2, and PFA3 genes from *Schizochytrium* sp. ATCC PTA-9695 were randomly integrated (strain B149).

The fatty acid profiles of the resulting prototrophic transformants were determined after growth in M2B media at 30° C. and several of the resulting strains were identified that had enhanced production of EPA. As shown in FIG. 5, the Schizochytrium sp. ATCC 20888 strain containing its native PFA1, PFA2, and PFA3 genes produced 0.98% EPA (% of total FAME produced), 13.75% DPA n-6, and 34.95% DHA after culture at 30° C. Three recombinant B149 strains [B149-E1 (also referred to as "B9"), B149-3 and B149-4] produced between 10.06 and 21.06% EPA, between 0.70 and 1.98% DPA n-6, and between 15.01 and 20.17% DHA after culture at 30° C.

Figure 6:
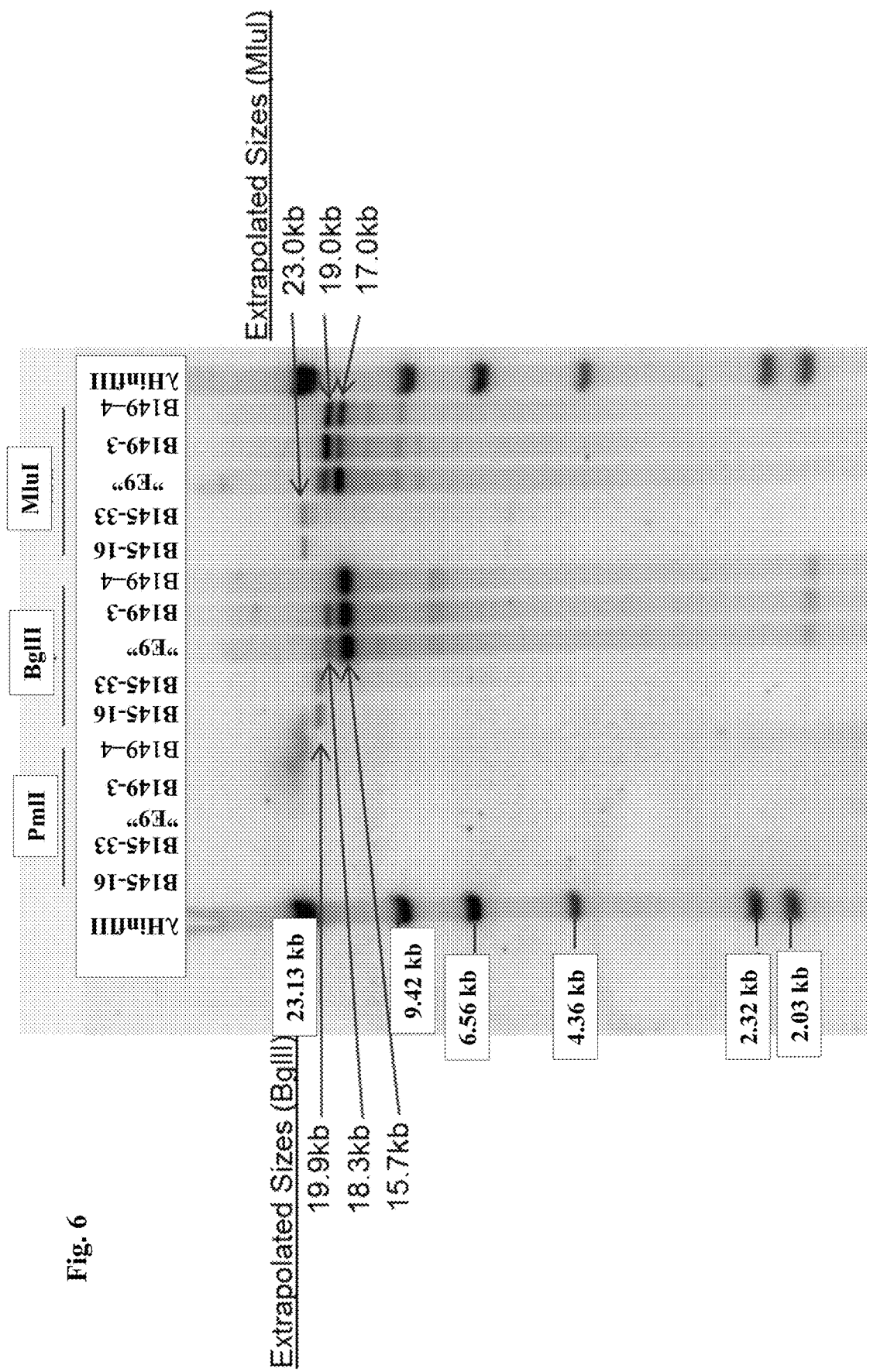
FIG. 6 shows a Southern blot of Schizochytrium strains B145 (B145-16 and B145-33) and B149 (E9, B149-3 and B149-4) probed with a labelled portion of the *Schizochytrium* sp. ATCC PTA-9695 PFA1 gene. Schizochytrium strain B145 was produced by targeted replacement of the native PFA1 PUFA synthase gene in *Schizochytrium* sp. ATCC 20888 with PFA1 from *Schizochytrium* sp. ATCC PTA-9695. Thus, recombinant strain B145 contains one copy of the *Schizochytrium* sp. ATCC PTA-9695 PFA1 gene and was used for comparison to determine the copy number of PFA1 in recombinant strain B149. Densitometric analysis indicated that the average reference band (B145) equaled 7,165 units. In contrast, the band from strain B149 ("E9") was calculated to be 42,747 units (approx. 6 copies of PFA1); the band from strain B149-3 was calculated to be 37,897 units (approx. 5-6 copies of PFA1); and the band from strain B149-4 was calculated to be 33,928 units (approx. 4-5 copies of PFA1).
Figure 7:
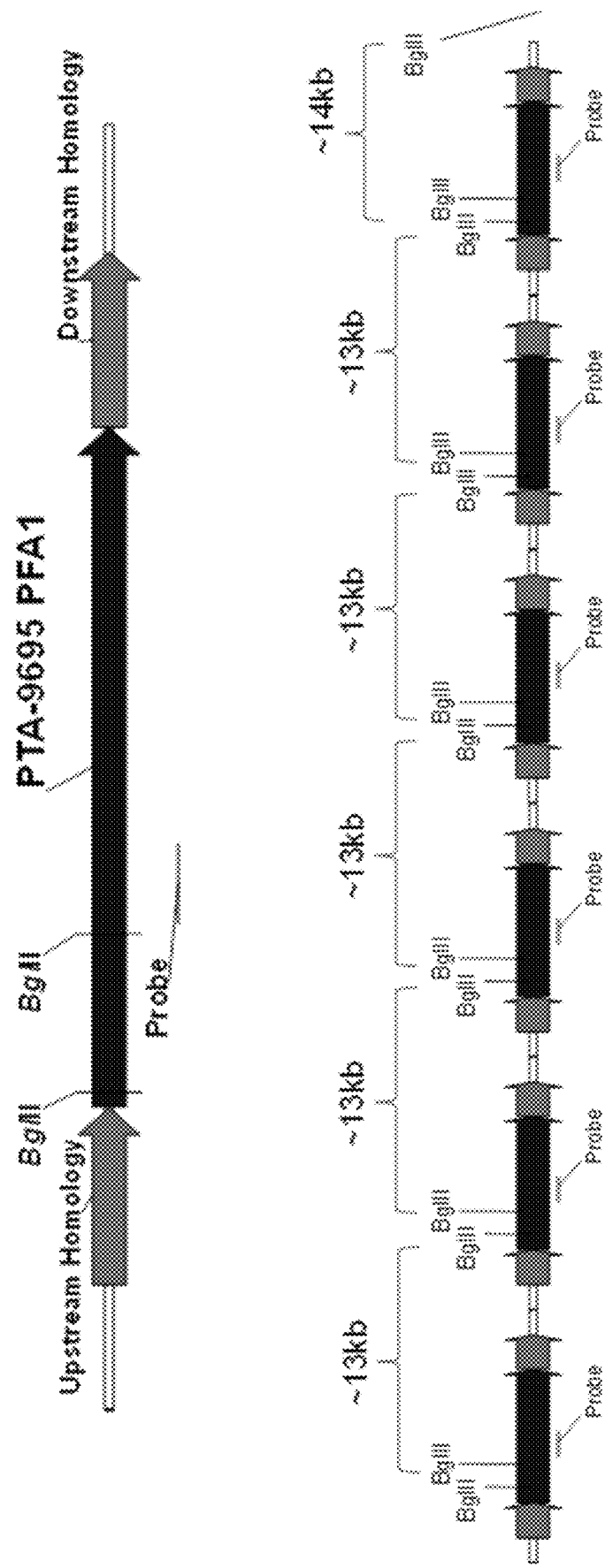
FIG. 7 shows a schematic for the multi-copy insertion of the PFA1 gene from *Schizochytrium* sp. ATCC PTA-9695 in Schizochytrium mutant strains of B149.

Further analysis of the enhanced EPA strains by Southern blot using a PFA1 probe indicated that it contains multiple copies of the PFA1 gene (see FIG. 6). DNA samples from strains in which the native PFA1 gene of Schizochytrium sp. ATCC 20888, was replaced with the PFA1 gene from Schizochytrium sp. ATCC PTA-9695 in a targeted manner are included for reference (i.e., strains B145-16 and B145-33). These strains have a single copy of the PFA1 gene (see Example 1 above). Densitometric calculation of these results suggests that the B149-E1 (B9) strain contains approximately 6 copies of the PFA1 gene and that the B149-3 strain contains approximately 5-6 copies and the B-149-4 contains approximately 4-5 copies of PFA. The data of FIG. 6 suggest that the multiple copies of the PFA1 gene are integrated at one site in the genome. This is shown schematically in FIG. 7.

Example 3

Addition of Extra Copies of PFA1 and/or PFA3 Genes in Transgenic Schizochytrium Strain B156-2

The Schizochytrium strain B156-2, described above in Example 1, lacks functional native PFA1, PFA2, and PFA3 genes and contains Schizochytrium sp. ATCC PTA-9695 PFA1, PFA2, and PFA3 genes inserted into the respective PFA1, PFA2, and PFA3 loci.

This strain was transformed with circular plasmids carrying an expression cassette containing the native strong promoter for elongation factor 1 (EF1) joined in reading frame 5' to the PFA1 gene or the PFA3 gene and the terminator of the native orfC gene (see U.S. Pat. No. 8,637,651). Specifically, the plasmid pTH049 contains the Schizochytrium sp. ATCC PTA-9695 PFA3 gene and the plasmid pTH050 contains the Schizochytrium sp. ATCC PTA-9695 PFA1 gene. pTH049 and pTH050 also contain resistance markers for selection with paromomycin and zeocin respectively. These genes presumably integrated randomly into the genome. The resulting transgenic strains contained one copy of PFA2 and at least 2 copies of PFA1 and/or PFA3 genes.

Figure 8:
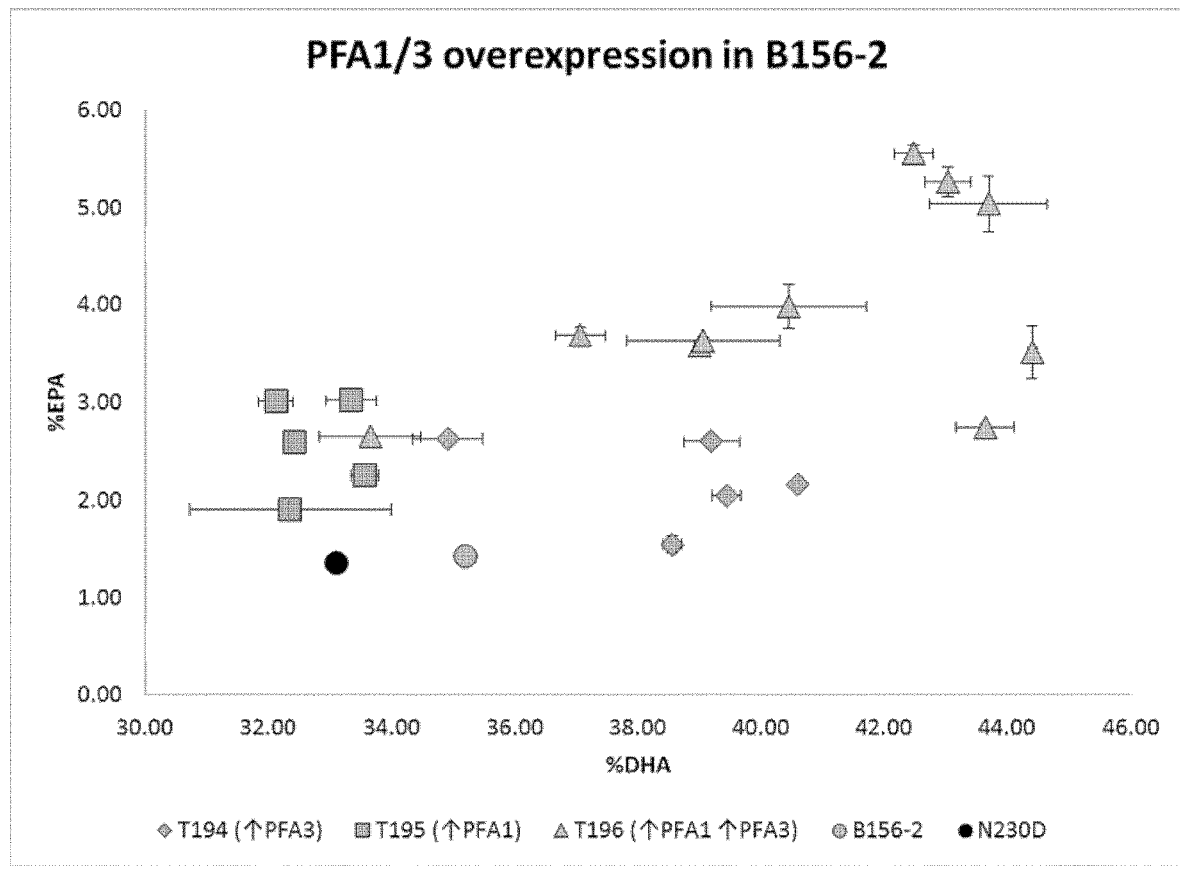
FIG. 8 shows EPA and DHA production in recombinant Schizochytrium strains that overexpress the PFA1 gene, PFA3 gene, and both PFA1 and PFA3 genes from Schizochytrium ATCC PTA-9695 compared to both the parent strain (recombinant strain B156-2) and the daughter strain of *Schizochytrium* sp. ATCC 20888 (*Schizochytrium* sp. N230D).

Screening of the resulting transformants (See FIG. 8) revealed that, compared with either the Schizochytrium sp. strain N230D or Schizochytrium sp. strain B156-2, additional copy(ies) of PFA1 (T195) resulted in enhanced production of EPA (~2-3% of total FAME). In contrast, DHA production was not affected by overexpression of PFA1 alone.

Additional copy(ies) of PFA3 (T194) resulted in slight enhancement of EPA (~1.6-2.6% of total FAME) but significant enhancement of DHA (~35-41% of total FAME).

Additional copies of both PFA1 and PFA3 (T196) resulted in significant enhancement of both EPA and DHA production. EPA production was increased to ~2.6-5.6% of total FAME (vs. ~1.3-1.5% in strains N230D and B156-2) and DHA production was increased to ~33.5-44.5% of total FAME (vs. ~33.0-35.5% in strains N230D and B156.2). Furthermore, depending on the site of insertion within the genome and possibly number of copies inserted, the EPA and DHA content varied slightly among the transgenic Schizochytrium strains.

Example 4

Figure 9:
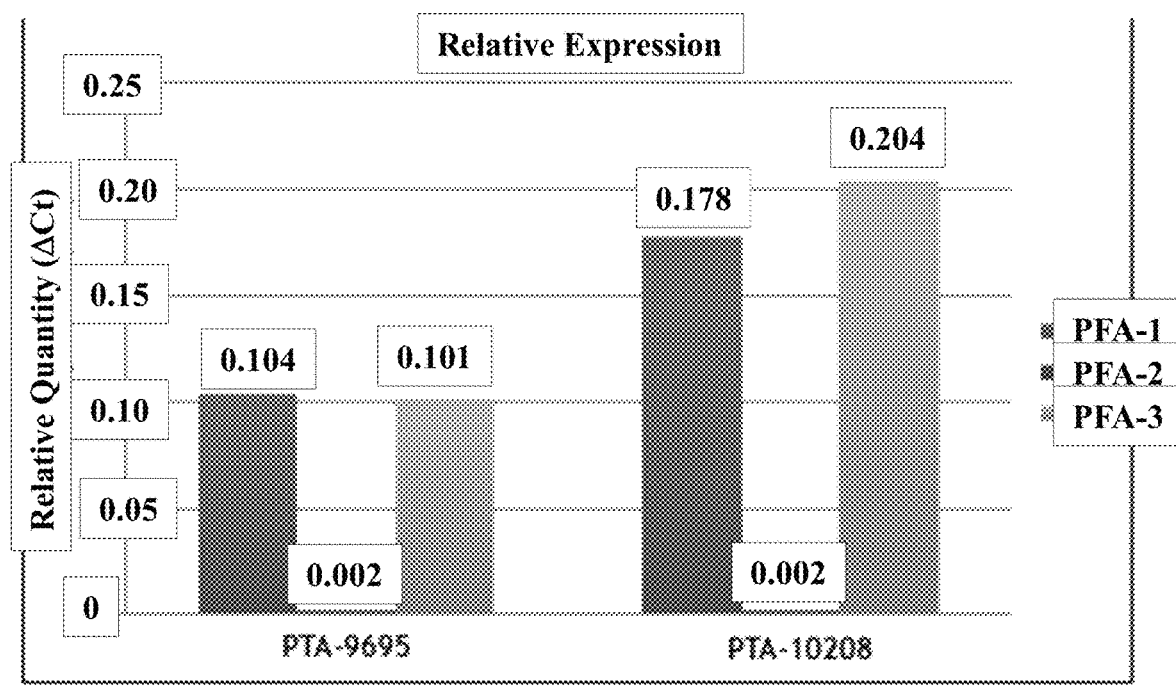
FIG. 9 shows PFA1, PFA2, and PFA3 expression in *Schizochytrium* sp. ATCC PTA-9695 and ATCC PTA-10208 as measured by quantitative PCR (qPCR).

Expression of PUFA synthase subunit genes PFA1, PFA2, and PFA3 in Schizochytrium sp. ATCC PTA-9695 and relative ATCC PTA-10208 strains accumulating different amounts of DHA and EPA Schizochytrium sp. ATCC PTA-9695 strain and related Schizochytrium sp. ATCC PTA-10208 strain both contain identical copies of the same genes PFA1, PFA2 and PFA3. However, despite this fact, they produce different amounts of EPA and DHA. Specifically, Schizochytrium sp. ATCC PTA-10208 contains about 24% EPA of total FAME and about 31% DHA of total FAME after 96 hours of fermentation at the 10 L scale in "standard" conditions. The Schizochytrium sp. ATCC PTA-9695 harbors the same PUFA synthase subunit gene set but contains about 9% EPA of total FAME and about 55% DHA of total FAME after 96 hours of fermentation at the 10 L scale. A qPCR analysis of PFA1, PFA2 and PFA3 was performed on both strains grown in "standard" shake flask conditions. The results indicated that PFA1 and PFA3 were expressed at a higher level in strain PTA-10208 than in strain PTA-9695. See FIG. 9.

Example 5

The PUFA synthase genes and additional copies of the PFA1 and PFA3 genes of Schizochytrium sp. ATCC PTA-9695 are installed in the Canola plant using Agrobacterium-based plasmid vectors for transformation using standard practices in the field. In addition, the HetI gene of Nostoc sp. or another appropriate PPTase are also installed in the plant along with an acyl-CoA synthetase that catalyzes the conversion of long chain polyunsaturated free fatty acids (FFA) to acyl-CoA.

Briefly, binary vectors are constructed that contained plant transcription units (PTUs) comprising the native or codon-optimized PUFA synthase genes (PFA1, PFA2, and PFA3) or other genes of interest (PPTase and ACS genes) operably linked to a promoter and 3'-UTR. Different promoter and 3'-UTR sequence combinations are incorporated in the binary vectors to drive expression of the PUFA synthase genes and other genes. Use of these different regulatory gene elements is incorporated into the design of the PTUs to alter and vary the expression levels of the transgenes. The PTUs are positioned within the binary vector in different orientations to test whether the orientation of the PTUs alters the expression levels of the transgenes. The resulting constructs are transformed into Agrobacterium tumefaciens according to standard protocols and confirmed by restriction enzyme digestion and sequencing.

For transformation of Canola, seeds are first germinated according to standard protocols in the field. Briefly, Canola seeds of interest are surface-sterilized in 10% Clorox for 10 minutes and rinsed three times with sterile distilled water. Seeds are planted for germination on, for example, 12 MS Canola medium (½×MS, 2% sucrose, 0.8% agar) contained in phytatrays, 25 seeds per phytatray and placed in a Percival Growth Chamber™ with growth regime set at 25° C., a photoperiod of 16 hours light, 8 hours dark; and germinated for 5 days.

The germinated seeds are then pre-treated according to standard protocols in the field. Briefly, on day 5, hypocotyl segments of about 3 mm in length are aseptically excised, discarding the root and shoot sections (drying of hypocotyls is prevented by placing hypocotyls segments into 10 ml of sterile ILLIQ® water during excision process). Hypocotyl segments are placed horizontally on sterile filter paper on callus induction medium MSK1D1 (1×MS, 1 mg/L kinetin, 1 mg/L 2,4-D, 3% sucrose, 0.7% PHYTAGAR®) for 3 days pre-treatment in a Percival Growth Chamber™ with a growth regime set at 22-23° C., and a photoperiod of 16 hours light, 8 hours dark.

Co-cultivation with *Agrobacterium* containing constructs of instruct is then started. The day before *Agrobacterium* treatment, flasks of YEP medium containing the appropriate antibiotics are inoculated. Hypocotyl segments are transferred from filter paper to empty 100×25 mm petri dishes containing 10 mL liquid M medium to prevent the hypocotyl segments from drying. A spatula is used at this stage to scoop the segments and transfer. The liquid M medium is removed with a pipette, and 40 mL *Agrobacterium* suspension is added to the petri dish (500 segments with 40 mL *Agrobacterium* solution). The segments are treated for 30 minutes with periodic swirling of the petri dish, so that the hypocotyls can stay immersed in the *Agrobacterium* solution.

At the end of the treatment period, the *Agrobacterium* solution is pipetted into a waste beaker, autoclaved and discarded (the *Agrobacterium* solution is completely removed to prevent *Agrobacterium* overgrowth). The treated hypocotyls are transferred with forceps back to the original plates containing MSK1D1 with filter paper (care is taken to ensure that the segments do not dry). The hypocotyl segments along with control segments are returned to the Percival Growth Chamber™ under reduced light intensity (by covering the plates with aluminum foil), and the treated hypocotyls are co-cultivated with *Agrobacterium* for 3 days.

After 3 days of co-cultivation, a selection medium is used to induce callus formation. The hypocotyl segments are transferred individually with forceps onto callus induction medium MSK1D1H1 (1×MS, 1 mg/L Kinetin, 1 mg/L 2,4-D, 0.5 gm/L MES, 5 mg/L AgNo3, 300 mg/L TIMENTIN®, 200 mg/L Carbenicillin™, 1 mg/L Herbiace™, 3% sucrose, 0.7% PHYTAGAR®). The hypocotyl segments are anchored on the medium, but are not embedded in the medium.

After 7 days on callus induction medium, the callusing hypocotyl segments are transferred to Shoot Regeneration Medium 1 with selection MSB3Z1H1 (1×MS, 3 mg/L BAP, 1 mg/L zeatin, 0.5 gm/L MES, 5 mg/L AgN03, 300 mg/L TIMENTIN®, 200 mg/L Carbenicillin™, 1 mg/L Herbiace™, 3% sucrose, 0.7% PHYTAGAR®). After 14 days, the hypocotyls with shoots are transferred to Regeneration Medium 2 with increased selection MSB3Z1H3 (1×MS, 3 mg/L BAP, 1 mg/L zeatin, 0.5 gm/L MES, 5 mg/L AgN03, 300 mg/L TIMENTIN®, 200 mg/L Carbenicillin™, 3 mg/L Herbiace™, 3% sucrose, 0.7% PHYTAGAR®).

After 14 days, the segments with shoots are transferred to shoot elongation medium MSMESH5 (1×MS, 300 mg/L TIMEN'HN®, 5 mg L Herbiace™, 2% sucrose, 0.7% TC Agar™) Shoots that are already elongated are isolated and transferred to MSMESH5. After 14 days, the remaining shoots which did elongate in the first round are placed on MSMESH5, and transferred to fresh selection medium of the same composition. At this stage, all remaining hypocotyl segments are discarded. Shoots that elongate on MSB3Z1H3 medium after 2 weeks are isolated and transferred to MSMESH5 medium. Remaining shoots that did elongate in the first round on MSMESH5 are isolated and transferred to fresh selection medium of the same composition. At this stage, all remaining hypocotyl segments are discarded.

After another 14 days, the shoots are transferred to MSMEST medium (IX MS, 0.5 g/L MES, 300 mg/L TIMENTIN®, 2% sucrose, 0.7% TC Agar™) for root induction. The shoots that do not root in the first transfer on MSMEST medium are transferred for a second or third cycle on MSMEST medium until rooted plants are obtained.

Samples for PCR are isolated after the shoots are cultured on MSMESH5 medium for at least 14 days. Leaf tissue from the green shoots is tested by PCR for the presence of the selectable marker gene. All chlorotic shoots are discarded and not subjected to the PCR assay. Samples that are positive for the PCR reaction are kept and the shoots are left on the MSMEST medium to elongate and develop roots. The shoots that are negative according to the PCR assay are discarded. Plants that root on MSMESH5 or MSMEST and are PCR-positive are sent for transplanting into soil. After hardening, the transgenic canola plants are further analyzed for events which contain all of the transgene PTU cassettes, and these plants are transferred to the greenhouse, grown to maturity, and the Ti seed are harvested for fatty acid composition analysis. The transgenes presence and copy numbers are also analyzed by quantitative PCR and protein amount by immunoblot analysis.

LC-PUFA production is detected in the Canola seeds, especially EPA and DHA. The presence of additional copies of PFA1 and PFA3 and/or regulatory sequences promoting increased PFA1 and PFA3 expression comparatively to PFA2 result in higher EPA accumulation.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A recombinant microalga that has been modified to express increased levels of polyunsaturated fatty acid synthase, comprising:
   (a) a first gene encoding a polyunsaturated fatty acid synthase subunit 1 (PFA1) which comprises a first amino acid sequence having at least 95% sequence identity to SEQ ID NO: 2, wherein the first amino acid sequence comprises a β-ketoacyl-ACP synthase (KS) domain having at least 95% sequence identity to SEQ ID NO: 8, a malonyl-CoA:ACP acyltransferase (MAT) domain having at least 95% sequence identity to SEQ ID NO: 10, an acyl carrier protein (ACP) domain having at least 95% sequence identity to SEQ ID NO: 12, 14, 16, 18, 20, 22, or 24, a β-ketoacyl-ACP reductase (KR) domain of SEQ ID NO: 26 and a FabA-like β-hydroxyacyl-ACP dehydrase (DH) domain having at least 95% sequence identity to SEQ ID NO: 28;
   (b) a second gene encoding a polyunsaturated fatty acid synthase subunit 2 (PFA2) which comprises a second amino acid sequence having at least 95% sequence identity to SEQ ID NO: 4, wherein the second amino acid sequence comprises a KS domain having at least 95% sequence identity to SEQ ID NO: 30, a chain length factor (CLF) domain having at least 95% sequence identity to SEQ ID NO: 32, an acyltransferase (AT) domain having at least 95% sequence identity to SEQ ID NO: 34 and an enoyl-ACP reductase (ER) domain having at least 95% sequence identity to SEQ ID NO: 36; and
   (c) a third gene encoding a polyunsaturated fatty acid synthase subunit 3 (PFA3) which comprises a third amino acid sequence having at least 95% sequence identity to SEQ ID NO: 6, wherein the third amino acid sequence comprises a DH domain having at least 95% sequence identity to SEQ ID NO: 38 or 40 and an ER domain having at least 95% sequence identity to SEQ ID NO: 42,
   wherein the recombinant microalga is a recombinant Schizochytrium,
   wherein the recombinant microalga comprises multiple copies of the first and/or third gene but only a single copy of the second gene, and
   wherein the recombinant microalga produces lipids with an increased level of eicosapentaenoic acid (EPA) compared to an unmodified microalga.

2. The recombinant microalga of claim 1, wherein the first gene is a heterologous gene.

3. The recombinant microalga of claim 1, wherein the second gene is a heterologous gene.

4. The recombinant microalga of claim 1, wherein the third gene is a heterologous gene.

5. The recombinant microalga of claim 1, wherein the first, second and third genes are heterologous genes.

6. The recombinant microalga of claim 1, wherein the microalga contains between 2 and 10 copies of the first gene.

7. The recombinant microalga of claim 1, wherein the expression of PFA1 and/or PFA3 is increased by at least 1.5 fold relative to the unmodified microalga.

8. The recombinant microalga of claim 1, wherein
   (a) the first amino acid sequence comprises a KS domain of SEQ ID NO: 8, a MAT domain of SEQ ID NO: 10, an ACP domain of SEQ ID NO: 12, a KR domain of SEQ ID NO: 26 and a DH domain of SEQ ID NO: 28;
   (b) the second amino acid sequence comprises a KS domain of SEQ ID NO: 30, a CLF domain of SEQ ID NO: 32, an AT domain of SEQ ID NO: 34 and an ER domain of SEQ ID NO: 36; and
   (c) the third amino acid sequence comprises a DH domain of SEQ ID NO: 38, a DH domain of SEQ ID NO: 40 and an ER domain of SEQ ID NO: 42.

9. The recombinant microalga of claim 1, wherein
   (a) the first amino acid sequence comprises SEQ ID NO: 2;
   (b) the second amino acid sequence comprises SEQ ID NO: 4; and
   (c) the third amino acid sequence comprises SEQ ID NO: 6.

10. A method for producing lipids in a microalga, comprising culturing the recombinant microalga of claim 1.

11. A recombinant plant that has been modified to express increased levels of polyunsaturated fatty acid synthase, comprising:
    (a) a first gene encoding a polyunsaturated fatty acid synthase subunit 1 (PFA1) which comprises a first amino acid sequence having at least 95% sequence identity to SEQ ID NO: 2, wherein the first amino acid sequence comprises a β-ketoacyl-ACP synthase (KS) domain having at least 95% sequence identity to SEQ ID NO: 8, a malonyl-CoA:ACP acyltransferase (MAT) domain having at least 95% sequence identity to SEQ ID NO: 10, an acyl carrier protein (ACP) domain having at least 95% sequence identity to SEQ ID NO: 12, 14, 16, 18, 20, 22, or 24, a β-ketoacyl-ACP reductase (KR) domain having at least 95% sequence identity to SEQ ID NO: 26 and a FabA-like p-hydroxyacyl-ACP dehydrase (DH) domain having at least 95% sequence identity to SEQ ID NO: 28;
    (b) a second gene encoding a polyunsaturated fatty acid synthase subunit 2 (PFA2) which comprises a second amino acid sequence having at least 95% sequence identity to SEQ ID NO: 4, wherein the second amino acid sequence comprises a KS domain having at least 95% sequence identity to SEQ ID NO: 30, a chain length factor (CLF) domain having at least 95% sequence identity to SEQ ID NO: 32, an acyltransferase (AT) domain having at least 95% sequence identity to SEQ ID NO: 34 and a enoyl-ACP reductase (ER) domain having at least 95% sequence identity to SEQ ID NO: 36; and
    (c) a third gene encoding a polyunsaturated fatty acid synthase subunit 3 (PFA3) which comprises a third amino acid sequence having at least 95% sequence identity to SEQ ID NO: 6, wherein the third amino acid sequence comprises a DH domain having at least 95% sequence identity to SEQ ID NO: 38 or 40 and an ER domain having at least 95% sequence identity to SEQ ID NO: 42,
    wherein the recombinant plant further comprises a polynucleotide encoding at least one phosphopantetheinyl transferase (PPTase),
    wherein the recombinant plant comprises multiple copies of the first and/or third transgene but only a single copy of the second transgene, and
    wherein the recombinant plant produces lipids with an increased level of eicosapentaenoic acid (EPA) compared to an unmodified plant.

12. The recombinant plant of claim 11, wherein
    (a) the first amino acid sequence comprises a KS domain of SEQ ID NO: 8, a MAT domain of SEQ ID NO: 10, an ACP domain of SEQ ID NO: 12, a KR domain of SEQ ID NO: 26 and a DH domain of SEQ ID NO: 28;

(b) the second amino acid sequence comprises a KS domain of SEQ ID NO: 30, a CLF domain of SEQ ID NO: 32, an AT domain of SEQ ID NO: 34 and an ER domain of SEQ ID NO: 36; and
(c) the third amino acid sequence comprises a DH domain of SEQ ID NO: 38, a DH domain of SEQ ID NO: 40 and an ER domain of SEQ ID NO: 42.

13. The recombinant plant of claim 11, wherein
(a) the first amino acid sequence comprises SEQ ID NO: 2;
(b) the second amino acid sequence comprises SEQ ID NO: 4; and
(c) the third amino acid sequence comprises SEQ ID NO: 6.

* * * * *